US006001804A

United States Patent [19]
Rabin

[11] Patent Number: 6,001,804
[45] Date of Patent: Dec. 14, 1999

[54] PANCREATIC ISLET CELL ANTIGENS OBTAINED BY MOLECULAR CLONING

[75] Inventor: Daniel U. Rabin, Branford, Conn.

[73] Assignee: Bayer Corporation, Tarrytown, N.Y.

[21] Appl. No.: 08/468,577

[22] Filed: Jun. 6, 1995

Related U.S. Application Data

[62] Division of application No. 08/239,276, May 5, 1994, Pat. No. 5,840,836, which is a continuation of application No. 07/872,646, Jun. 8, 1992, abandoned, which is a continuation of application No. 07/715,181, Jun. 14, 1991, abandoned, which is a continuation-in-part of application No. 07/441,703, Dec. 4, 1989, abandoned, which is a continuation-in-part of application No. 07/312,543, Feb. 17, 1989, abandoned.

[51] Int. Cl.⁶ .............. A61K 67/00; C12Q 1/00; C07H 17/00; C07K 14/00
[52] U.S. Cl. .............. 514/12; 435/7.1; 435/252.3; 435/320.1; 536/23.1; 530/350; 530/300
[58] Field of Search ............... 435/7.1, 7.21, 435/69.1, 69.3, 240.1, 252.3, 320.1; 530/350; 536/22.1, 23.4, 23.5; 514/12

[56] References Cited

U.S. PATENT DOCUMENTS

| | | | |
|---|---|---|---|
| 4,983,729 | 1/1991 | Sikora | 435/172.3 |
| 5,041,536 | 8/1991 | Brideau et al. | 530/350 |
| 5,171,568 | 12/1992 | Burke et al. | 424/186.1 |
| 5,200,318 | 4/1993 | Rabin et al. | 435/7.21 |
| 5,219,990 | 6/1993 | Androphy et al. | 530/350 |
| 5,229,274 | 7/1993 | Crawford et al. | 435/69.1 |
| 5,279,938 | 1/1994 | Rosa | 435/6 |
| 5,288,607 | 2/1994 | Emorine et al. | 435/6 |
| 5,366,883 | 11/1994 | Asada et al. | 435/202 |
| 5,420,019 | 5/1995 | Theofan et al. | 435/69.1 |
| 5,476,926 | 12/1995 | Spiegelman et al. | 536/24.1 |
| 5,489,432 | 2/1996 | Payne et al. | 424/405 |
| 5,489,513 | 2/1996 | Springer et al. | 435/6 |
| 5,492,809 | 2/1996 | Miller et al. | 435/6 |
| 5,505,943 | 4/1996 | Fortney et al. | 424/94.63 |
| 5,508,165 | 4/1996 | Halverson et al. | 435/6 |
| 5,512,460 | 4/1996 | Nauro et al. | 435/69.1 |
| 5,527,682 | 6/1996 | Owens et al. | 435/6 |
| 5,527,775 | 6/1996 | Shorr et al. | 514/12 |
| 5,532,127 | 7/1996 | Gallatin et al. | 435/6 |
| 5,534,223 | 7/1996 | Boquet et al. | 422/61 |
| 5,538,892 | 7/1996 | Donahoe et al. | 435/240.2 |

OTHER PUBLICATIONS

*Joslin's Diabetes Mellitus*, 13th Edition, C. Kahn et al., editors, Lea & Febiger, Philadelphia, 1994, pp. 18–19.
*Diabetes*, Abstract Book, 56th Annual Meeting, Jun. 1996, Abstract Nos. 290, 291, 293–296, 879, 882, 893, 1128,1129 and 1137.
C. Verge et al., *Diabetes*, 45: 926 (1996).
I. Durinovic–Bellò et al., *Diabetes*, 45: 795 (1996).
U. Roll et al., *Diabetes*, 45: 967 (1996).
R. Gianani et al., *Diabetes*, 44: 1340 (1995).
M. Myers et al., *Diabetes*, 44: 1290 (1995).
D. Rabin et al., *J. Immunology*, 152: 3183 (1994).
D. Rabin et al., *Diabetes*, 41: 183 (1992).
M. Lan et al., *DNA and Cell Biol.*, 13: 505 (1994).
D. Rabin et al., *J. Immunol. Methods*, 156: 101 (1992).
Abstracts of Medline Search conducted on Jul. 22, 1996.
K. Krisch et al., *Lab. Invest.*, 58: 411 (1988).
M. Solimena et al., *EMBO Journal*, 15: 2102 (1996).
D. Karounos et al., *Diabetes*, 39: 1085 (1990).
D. Karounos et al., *Autoimmunity*, 6: 79 (1990).
C. Goodnow, *Proc.Natl.Acad.Sci. USA*, 93: 2264 (1996).
A. Tarkowski et al., *Arthritis and Rheumatism*, 32: 1087 (1989).
N. Seki, *J. Immunology*, 140: 1477 (1988).
D. Trentham, *Science*, 261: 1727 (1993).
J. Courtenay et al., *Nature*, 283: p. 666 only (1980).
S. Khare, *J. Immunmology*, 155: p. 3653 only (1995).
B. Driscoll et al., *J. Immunology*, 112: p. 392 only (1974).
M. Samson et al., *J. Immunology*, 155: p. 2737 only (1995).
P. Matsiota et al., *Ann.Inst.Pasteur Immunol.*, 139: 99 (1988), abstract only.
A. Wajgt et al., *Acta Neurol. Scand.*, 68: 337 (1983), abstract only.
D. Daniel et al., *Eur. J. Immunol.*, 25: 1056 (1995), abstract only.
D. Kaufman et al., *Nature*, 366: 69 (1993), abstract only.
R. Tisch et al., *Nature*: 366: 72 (1993), abstract only.
N. Schloot et al., *Immunology Today*, 16: 289 (1995).
*Official Gazette* for Jul. 30, 1996, p. 3679, abstract of U.S. Patent No. 5,541,095, issued to Hirschberg et al.
Srikanta et al. (1986) Mol. Biol. Med 3:113–127.
Karounos et al. (1988) Diabetes 37(5):30 A.
Moncayo et al (1988) Diabelologia 31(7):523 A.

*Primary Examiner*—Karen Cochrane Carlson
*Attorney, Agent, or Firm*—Sprung Kramer Schaefer & Briscoe

[57] ABSTRACT

Pancreatic islet cell antigens (ICA) that bind with antibodies found in the sera of patients afflicted with insulin-dependent (Type I) diabetes mellitus (IDDM). ICA proteins are expressed by recombinant cloning vehicles comprising DNA inserts isolated from islet cells. Full sequence native ICA proteins, or protein or peptide fragments thereof, can be used in the diagnosis of IDDM and in detecting or blocking human immunoglobulin, T-cells, or B-cells involved in IDDM.

26 Claims, 14 Drawing Sheets

DIABETIC

NORMAL

DIABETIC

NORMAL

DIABETIC

NORMAL

DIABETIC

NORMAL

DIABETIC

NORMAL

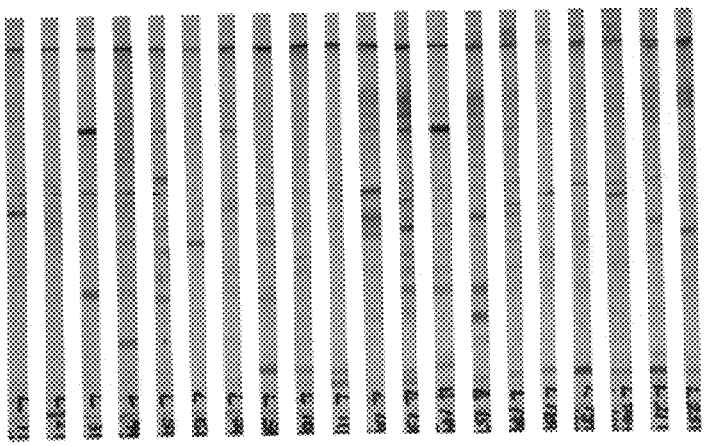 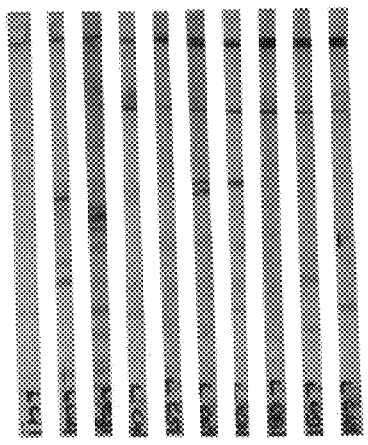
FIG. 6a
DIABETIC
FIG. 6b
NORMAL

ICA CLONES 2/89

| SERUM | | 12 | 13 | 208 | 302 | 313 |
|---|---|---|---|---|---|---|
| 1 | 1 | 3 | 1 | | | 1 |
| 2 | 2 | | | | | |
| 3 | 3 | | | | ? | |
| 4 | 4 | | | | | |
| 5 | 5 | 2 | | 2 | | |
| 6 | 6 | 4 | 2 | 2 | | 3 |
| 7 | 7 | 3 | | 3 | 2 | |
| 8 | 9 | | | 4 | | |
| 9 | 10 | | | | | |
| 10 | 11 | | | | | |
| 11 | 12 | 3 | 2 | | | |
| 12 | 13 | | | | | |
| 13 | 14 | | | 4 | ? | |
| 14 | 15 | | | 3 | | |
| 15 | 17 | 3 | 2 | | | 2 |
| 16 | 18 | 3 | 2 | 1 | | 1 |
| 17 | 19 | ? | | | | |
| 18 | 20 | ? | | | 2 | |
| 19 | 21 | | 1 | 1 | 4 | |
| 20 | 23 | | | | 1 | |
| 21 | c1 | | | | | |
| 22 | c2 | | | | | |
| 23 | c3 | | | | | |
| 24 | c4 | | | | | |
| 25 | c5 | | | | | |
| 26 | c6 | | | | | |
| 27 | c7 | | | | | |
| 28 | c8 | | | 2 | | |
| 29 | c9 | | | | | |
| 30 | c10 | | | | | |

FIG. 7

DIABETIC

NORMAL

DIABETIC

NORMAL

PROFILES

| SERUM | | 505 | 525 |
|---|---|---|---|
| 1 | 7601 | | 4 |
| 2 | 7645 | | |
| 3 | 7668 | | |
| 4 | 7677 | | |
| 5 | 13782 | | 4 |
| 6 | 13860 | 1 | 4 |
| 7 | 13916 | | |
| 8 | P5 | | 2 |
| 9 | P6 | 1 | |
| 10 | P7 | | 4 |
| 11 | P8 | | 3 |
| 12 | P21 | | 3 |
| 13 | P26 | 3 | |
| 14 | P28 | 2 | |
| 15 | MRC41 | | |
| 16 | MRC42 | | 1 |
| 17 | MRC43 | 1 | |
| 18 | MRC44 | | |
| 19 | MRC45 | | |
| 20 | MRC46 | | |

FIG. 10

SEQUENCE LISTING (1) GENERAL INFORMATION:

(iii) NUMBER OF SEQUENCES: 19

(2) INFORMATION FOR SEQ ID NO: 1:

(i) SEQUENCE CHARACTERISTICS:
      (A) LENGTH: 1397 nucleotides
      (B) TYPE: nucleic acid
      (C) STRANDEDNESS: single
      (D) TOPOLOGY: linear (xi) SEQUENCE DESCRIPTION: SEQ ID NO: 1:

```
GG  CCC ATG AAC GCC TTC ATG GTG TGG GCC AAG                             32
    Pro Met Asn Ala Phe Met Val Trp Ala Lys
                  5                      10

GAT GAG CGG AGG AAG ATC CTG CAA GCC TTC                                 62
Asp Glu Arg Arg Lys Ile Leu Gln Ala Phe
              15                      20

CCA GAC ATG CAC AAC TCC AGC ATC AGC AAG                                 92
Pro Asp Met His Asn Ser Ser Ile Ser Lys
              25                      30

ATC CTT GGA TCT CGC TGG AAG TCC ATG ACC                                122
Ile Leu Gly Ser Arg Trp Lys Ser Met Thr
              35                      40

AAC CAG GAG AAN CAG CCC TAC TAT GAG GAA                                152
Asn Gln Glu Xaa Gln Pro Tyr Tyr Glu Glu
              45                      50

CAG GCT CTG CTG ATC GTC ATC ACC TGG AGA                                182
Gln Ala Leu Leu Ile Val Ile Thr Trp Arg
              55                      60

AGT ATC CTG ACT ACA AGT ACA AGC CGC GGC                                212
Ser Ile Leu Thr Thr Ser Thr Ser Arg Gly
              65                      70

CAA GCG CAC CTG CAT CGT GGA GGG CAA GCG                                242
Gln Ala His Leu His Arg Gly Gly Gln Ala
              75                      80
```

| | |
|---|---|
| GCT GCG CGT GGG AGA GTA CAA GGC CCT GAT<br>Ala Ala Arg Gly Arg Val Gln Gly Pro Asp<br>                   85                         90 | 272 |
| GAG GAC CCG GCG TCA GGA TGC CCG CCA GAG<br>Glu Asp Pro Ala Ser Gly Cys Pro Pro Glu<br>                   95                       100 | 302 |
| CTA CGT GAT CCC CCC GCA GGC TGG CCA GGT<br>Leu Arg Asp Pro Pro Ala Gly Trp Pro Gly<br>                  105                   110 | 332 |
| GCA GAT GAG CTC CTC AGA TGT CCT GTA CCC<br>Ala Asp Glu Leu Leu Arg Cys Pro Val Pro<br>                  115                   120 | 362 |
| TCG GGC AGC AGG CAT GCC GCT GCA CAG CCA<br>Ser Gly Ser Arg His Ala Ala Ala Gln Pro<br>                  125                   130 | 392 |
| CTG GTG GAG CAC TAT GTC CCT CGT AGC CTG<br>Leu Val Glu His Tyr Val Pro Arg Ser Leu<br>                  135                   140 | 422 |
| GAC CCC AAC ATG CCT GTG ATC GTC AAC ACC<br>Asp Pro Asn Met Pro Val Ile Val Asn Thr<br>                  145                   150 | 452 |
| TGC AGC CTC AGA GAG GAG GGT GAG GGC ACA<br>Cys Ser Leu Arg Glu Glu Gly Glu Gly Thr<br>                  155                   160 | 482 |
| GAT GAC AGG CAC TCG GTG GCT GAT GGC GAG<br>Asp Asp Arg His Ser Val Ala Asp Gly Glu<br>                  165                   170 | 512 |
| ATG TAC CGG TAC AGC GAG GAC GAG GAC TCG<br>Met Tyr Arg Tyr Ser Glu Asp Glu Asp Ser<br>                  175                   180 | 542 |
| GAG GGT GAA GAG AAG AGC GAT GGG GAG TTG<br>Glu Gly Glu Glu Lys Ser Asp Gly Glu Leu<br>                  185                   190 | 572 |
| GTG GTG CTC ACA GAC TGATCCCGGC TGGGTGGCCT<br>Val Val Leu Thr Asp<br>                  195 | 607 |
| GGCCCCTTCT CCTCTGGGGA AGACCTTGTC CCAACTCGAT | 647 |
| GGGCACAGCC AGCCAACCTA AGACTATGTT GGTACTTGGA | 687 |
| CTTGTTCGTG CCCCAGAGAT GGGCAAAGCT GTGCACTTGC | 727 |
| AGATACATTC ATGAGGGGAG AGGCTCTCTC CCTTCCTGAG | 767 |
| GAGCTGTTGG CCTGGGTGGG CAGGAACTGC AGTATGGCCA | 807 |
| TGGGCTGAGC AGGCTGAGCA CCTCAGCCTT TAGGGCTTAT | 847 |
| GGCCAGGGGA CACTGTATGA CTCTCCTCTC CTGCAGGTGT | 887 |
| CTATCCACCT GGGGTATGGC ATCTACCGAC CTGTCTCCCT | 927 |
| GGGGTCACAT GCTTTGTTTC CAGGCTTGTC CTGGCTGGAC | 967 |
| CAGCCACTGT GGGACCAACA CCCCTCCCAC ACTCCCCCAG | 1007 |
| ACTGCTCGTC TATCACCAGG ATCGCTTTGT ACTTTGTGCA | 1047 |
| AAAGGGTCTG GCTGTCCCTT GCTGTTTTCA TCTCTGCCAA | 1087 |
| GCCTATTGTG CCTCTGGCTG CTGTATGTGT GCGCGTGCAC | 1127 |
| GTGTGTGTGT TTCATCTGTT CATTCACTGC ACAGAGTATT | 1167 |
| TATTGTGTGC CCACTACGTG CCAGGCACTG TTGCTGAGTT | 1207 |
| CCTGTGGGTG TGTCTCTCGA TGCCACTCCT GCTTCTCTGG | 1247 |

```
GGGCCTCTTT CTGTGCTTCT CTTTGTCCCC AAATTGCTAC                    1287

CTCTTTGTCA GTCTGGGTGT CTCAGGTTCT GTGTGTCCTT                    1327

GTGTGCATTT CTGTCTCTCT CTGTCCTCGT CTCTCTGCAA                    1367

GGCCCTCTAT TTCTCTCTTT CTTGGTGTCT                               1397

(2) INFORMATION FOR SEQ ID NO: 2:

(i) SEQUENCE CHARACTERISTICS:
        (A) LENGTH: 5051 nucleotides
        (B) TYPE:   nucleic acid
        (C) STRANDEDNESS: single
        (D) TOPOLOGY:   linear (xi) SEQUENCE DESCRIPTION: SEQ ID NO: 2:

GGCAGAGCTT GAAGA ATG TCT TCC AAG CAA                            30
               Met Ser Ser Lys Gln
                              5

GCC ACC TCT CCA TTT GCC TGT GCA GCT GAT                         60
Ala Thr Ser Pro Phe Ala Cys Ala Ala Asp
             10                  15

GGA GAG GAT GCA ATG ACC CAG GAT TTA ACC                         90
Gly gln Asp Ala Met Thr Gln Asp Leu Thr
             20                  25

TCA AGG GAA AAG GAA GAG GGC AGT GAT CAA                        120
Ser Arg Glu Lys Glu Glu Gly Ser Asp Gln
             30                  35

CAT GTG GCC TCC CAT CTG CCT CTG CAC CCC                        150
His Val Ala Ser His Leu Pro Leu His Pro
             40                  45

ATA ATG CAC AAC AAA CCT CAC TCT GAG GAG                        180
Ile Met His Asn Lys Pro His Ser Glu Glu
             50                  55

CTA CCA ACA CTT GTC AGT ACC ATT CAA CAA                        210
Leu Pro Thr Leu Val Ser Thr Ile Gln Gln
             60                  65

GAT GCT GAC TGG GAC AGC GTT CTG TCA TCT                        240
Asp Ala Asp Trp Asp Ser Val Leu Ser Ser
             70                  75

CAG CAA AGA ATG GAA TCA GAG AAT AAT AAG                        270
Gln Gln Arg Met Glu Ser Gln Asn Asn Lys
             80                  85

TTA TGT TCC CTA TAT TCC TTC CGA AAT ACC                        300
Leu Cys Ser Leu Tyr Ser Phe Arg Asn Thr
             90                  95

TCT ACC TCA CCA CAT AAG CCT GAC GAA GGG                        330
Ser Thr Ser Pro His Lys Pro Asp Glu Gly
            100                 105

AGT CGG GAC CGT GAG ATA ATG ACC AGT GTT                        360
Ser Arg Asp Arg Glu Ile Met Thr Ser Val
            110                 115

ACT TTT GGA ACC CCA GAG CGC CGC AAA GGG                        390
Thr Phe Gly Thr Pro Glu Arg Arg Lys Gly
            120                 125

AGT CTT GCC GAT GTG GTG GAC ACA CTG AAA                        420
Ser Leu Ala Asp Val Val Asp Thr Leu Lys
            130                 135

CAG AAG AAG CTT GAG GAA ATG ACT CGG ACT                        450
Gln Lys Lys Leu Glu Glu Met Thr Arg Thr
            140                 145
```

| | |
|---|---|
| GAA CAA GAG GAT TCC TCC TGC AGT GAA AAA<br>Glu Gln Glu Asp Ser Ser Cys Met Glu Lys<br>150                               155 | 480 |
| CTA CTT TCA AAA GAT TGG AAG GAA AAA ATG<br>Leu Leu Ser Lys Asp Trp Lys Glu Lys Met<br>160                               165 | 510 |
| GAA AGA CTA AAT ACC AGT GAA CTT CTT GGA<br>Glu Arg Leu Asn Thr Ser Glu Leu Leu Gly<br>170                               175 | 540 |
| GAA ATT AAA GGT ACA CCT GAG AGC CTG GCA<br>Glu Ile Lys Gly Thr Pro Glu Ser Leu Ala<br>180                               185 | 570 |
| GAA AAA GAA CGG CAG CTC TCC ACC ATG ATT<br>Glu Lys Glu Arg Gln Leu Ser Thr Met Ile<br>190                               195 | 600 |
| ACC CAG CTG ATC AGT TTA CGG GAG CAG CTA<br>Thr Gln Leu Ile Ser Leu Arg Glu Gln Leu<br>200                               205 | 630 |
| CTG GCA GCG CAT GAT GAA AGA AAA AAA CTG<br>Leu Ala Ala His Asp Glu Gln Lys Lys Leu<br>210                               215 | 660 |
| GCA GCG TCA CAA ATT GAG AAA CAA CGG CAG<br>Ala Ala Ser Gln Ile Glu Lys Gln Arg Gln<br>220                               225 | 690 |
| CAA ATG GAC CTT GCT CGC CAA CAG CAA GAA<br>Gln Met Asp Leu Ala Arg Gln Gln Gln Glu<br>230                               235 | 720 |
| CAG ATT GCG AGA CAA CAG CAG CAA CTT CTG<br>Gln Ile Ala Arg Gln Gln Gln Gln Leu Leu<br>240                               245 | 750 |
| CAA CAG CAG CAC AAA ATT AAT CTC CTG CAG<br>Gln Gln Gln His Lys Ile Asn Leu Leu Gln<br>250                               255 | 780 |
| CAA CAG ATC CAG GTT CAG GGT CAC ATG CCT<br>Gln Gln Ile Gln Val Gln Gly His Met Pro<br>260                               265 | 810 |
| CCG CTC ATG ATC CCA ATT TTT CCA CAT GAC<br>Pro Leu Met Ile Pro Ile Phe Pro His Asp<br>270                               275 | 840 |
| CAG CGG ACT CTG GCA GCA GCT GCT GCT GCC<br>Gln Arg Thr Leu Ala Ala Ala Ala Ala Ala<br>280                               285 | 870 |
| CAA CAG GGA TTC CTC TTC CCC CCT GGA ATA<br>Gln Gln Gly Phe Leu Phe Pro Pro Gly Ile<br>290                               295 | 900 |
| ACA TAC AAA CCA GGT GAT AAC TAC CCC GTA<br>Thr Tyr Lys Pro Gly Asp Asn Tyr Pro Val<br>300                               305 | 930 |
| CAG TTC ATT CCA TCA ACA ATG GCA GCT GCT<br>Gln Phe Ile Pro Ser Thr Met Ala Ala Ala<br>310                               315 | 960 |
| GCT GCT TCT GGA CTC AGC CCT TTA CAG CTC<br>Ala Ala Ser Gly Leu Ser Pro Leu Gln Leu<br>320                               325 | 990 |
| CAG AAG GGT CAT GTC TCC CAC CCA CAA ATT<br>Gln Lys Gly His Val Ser His Pro Gln Ile<br>330                               335 | 1020 |
| AAC CAA AGG CTA AAG GGC CTA AGT GAC CGT<br>Asn Gln Arg Leu Lys Gly Leu Ser Asp Arg<br>340                               345 | 1050 |

| | |
|---|---|
| TTT GGC AGG AAT TTG GAC ACC TTT GAA CAT<br>Phe Gly Arg Asn Leu Asp Thr Phe Glu His<br>350                          355 | 1080 |
| GGT GGT GGC CAC TCT TAC AAC CAC AAA CAG<br>Gly Gly Gly His Ser Tyr Asn His Lys Gln<br>360                          365 | 1110 |
| ATT GAG CAG CTC TAT GCC GCT CAG CTG GCC<br>Ile Glu Gln Leu Tyr Ala Ala Gln Leu Ala<br>370                          375 | 1140 |
| AGC ATG CAG GTG TCA CCT GGA GCA AAG ATG<br>Ser Met Gln Val Ser Pro Gly Ala Lys Met<br>380                          385 | 1170 |
| CCA TCA ACT CCA CAG CCA CCA AAC ACA GCA<br>Pro Ser Thr Pro Gln Pro Pro Asn Thr Ala<br>390                          395 | 1200 |
| GGG ACG GTC TCA CCT ACT GGG ATA AAA AAT<br>Gly Thr Val Ser Pro Thr Gly Ile Lys Asn<br>400                          405 | 1230 |
| GAA AAG AGA GGG ACC AGC CCT GTA ACT CAA<br>Glu Lys Arg Gly Thr Ser Pro Val Thr Gln<br>410                          415 | 1260 |
| GTT AAG GAT GAA GCA GCA GCA CAG CCT CTG<br>Val Lys Asp Glu Ala Ala Ala Gln Pro Leu<br>420                          425 | 1290 |
| AAT CTC TCA TCC CGA CCC AAG ACA GCA GAG<br>Asn Leu Ser Ser Arg Pro Lys Thr Ala Glu<br>430                          435 | 1320 |
| CCT GTA AAG TCC CCA ACG TCT CCC ACC CAG<br>Pro Val Lys Ser Pro Thr Ser Pro Thr Gln<br>440                          445 | 1350 |
| AAC CTC TTC CCA GCC AGC AAA ACC AGC CCT<br>Asn Leu Phe Pro Ala Ser Lys Thr Ser Pro<br>450                          455 | 1380 |
| GTC AAT CTG CCA AAC AAA AGC AGC ATC CCT<br>Val Asn Leu Pro Asn Lys Ser Ser Ile Pro<br>460                          465 | 1410 |
| AGC CCC ATT GGA GGA AGC CTG GGA AGA GGA<br>Ser Pro Ile Gly Gly Ser Leu Gly Arg Gly<br>470                          475 | 1440 |
| TCC TCT TTA GAT ATC CTA TCT AGT CTC AAC<br>Ser Ser Leu Asp Ile Leu Ser Ser Leu Asn<br>480                          485 | 1470 |
| TCC CCT GCC CTT TTT GGG GAT CAG GAT ACA<br>Ser Pro Ala Leu Phe Gly Asp Gln Asp Thr<br>490                          495 | 1500 |
| GTG ATG AAA GCC ATT CAG GAG GCG CGG AAG<br>Val Met Lys Ala Ile Gln Glu Ala Arg Lys<br>500                          505 | 1530 |
| ATG CGA GAG CAG ATC CAG CGG GAG CAA CAG<br>Met Arg Glu Gln Ile Gln Arg Glu Gln Gln<br>510                          515 | 1560 |
| CAG CAA CAG CCA CAT GGT GTT GAC GGG AAA<br>Gln Gln Gln Pro His Gly Val Asp Gly Lys<br>520                          525 | 1590 |
| CTG TCC TCC ATA AAT AAT ATG GGG CTG AAT<br>Lys Ser Ser Ile Asn Asn Met Gly Leu Asn<br>530                          535 | 1620 |
| AGC TGC AGG AAT GAA AAG GAA AGA ACG CGC<br>Ser Cys Arg Asn Glu Lys Glu Arg Thr Arg<br>540                          545 | 1650 |

| | |
|---|---|
| TTT GAG AAT TTG GNN CCC CAG TTA ACG GGA<br>Phe Glu Asn Leu Xaa Pro Gln Leu Thr Gly<br>550                        555 | 1680 |
| AAG TCA AAT GAA GAT GGA AAA CTG GGC CCA<br>Lys Ser Asn Glu Asp Gly Lys Leu Gly Pro<br>560                        565 | 1710 |
| GGT GTC ATC GAC CTT ACT CGG CCA GAA GAT<br>Gly Val Ile Asp Leu Thr Arg Pro Glu Asp<br>570                        575 | 1740 |
| GCA GAG GGA GGT GCC ACT GTG GCT GAA GCA<br>Ala Glu Gly Gly Ala Thr Val Ala Glu Ala<br>580                        585 | 1770 |
| CGA GTC TAC AGG GAC GCC CGC GGC CTG CCA<br>Arg Val Tyr Arg Asp Ala Arg Gly Leu Pro<br>590                        595 | 1800 |
| GCA GCG AGC CAC ACA TTA AGC GAC CAA<br>Ala Ala Ser His Thr Leu Ser Asp Gln<br>600 | 1827 |
| TGAATGCATT CATGGTTTGG GCAAAGGATG AGAGGAGAAA | 1867 |
| AATCCTTCAG GCCTTCCCCG ACATGCATAA CTCCAACATT | 1907 |
| AGCAAAATCT TAGGATCTCG CTGGAAATCA ATGTCCAACC | 1947 |
| AGGAGAAGCA ACCTTATTAT GAAGAGCAGG CCCGGCTAAG | 1987 |
| CAAGATCCAC TTAGAGAAGT ACCCAAACTA TAAATACAAA | 2027 |
| CCCCGACCGA AACNCACCTG CATTGTTGAT GGCAAAAAGC | 2067 |
| TTCGGATTGG GGAGTATAAG CAACTGATGA GGTCTCGGAG | 2107 |
| ACAGGAGATG AGGCAGTTCT TTACTGTGGG GCAACAGCCT | 2147 |
| CAGATTCCAA TCACCACAGG AACAGGTGTT GTGTATCCTG | 2187 |
| GTGCTATCAC TATGGCAACT ACCACACCAT CGCCTCAGAT | 2227 |
| GACATCTGAC TGCTCTAGCA CCTCGGCCAG CGCGGAGCCC | 2267 |
| AGCCTCCCGG TCATCCAGAG CACTTATGGT ATGAAGACAG | 2307 |
| ATGGCGGAAG CTAGCTGGAA ATGAAATGAT CAATGGAGAG | 2347 |
| GATGAAATGG AAATGTATGA TGACTATGAA GATGACCCCA | 2387 |
| AATCAGACTA TAGCAGTGAA AATGAAGCCC CGGAGGCTGT | 2427 |
| CAGAGCCAAC TGAGGAGTTT TTGTTTGCTG AATTAAAGTA | 2467 |
| CTCTGACATT TCACCCCCCT CCCCAACAAA GAGTTATCCA | 2507 |
| AGAGCCCGCA TGCATTTGTG GCTCCACAAT TACATCAGCA | 2547 |
| GAATGGTCTT AATTGTTTCG TAAAGTGTGA CACAGATTAA | 2587 |
| GTTTTCCCTG ATTTTTCATG AACTTGAGTT TTTTGTTGTT | 2627 |
| ATTGTTATTG TTGTTGTTGT TGTTTTTTTT TTTTGTTGTT | 2667 |
| ATTGTTATTG TTGTTGTTGT TGTTTTTTTA ATTTAGGTGA | 2707 |
| AGACATATTA AATATGAGAC ACCAGGACTT GAAACTTATC | 2747 |
| TCAACCCGTA GATGTCTTAC AAGTCTTATA TTTTTGTCTT | 2787 |
| ACTTTTTTTT TCTTTTGGAT GTTGATAAAG GTTAAGTTA | 2827 |
| CTGTTTTAGA TGGGGTTAAA CATTCTCACT CAGGTATGCT | 2867 |
| GTGCCGGCCT ACAGGTTGTG AATGTGTTTT TTATTCTGAA | 2907 |
| TTATTTTAGA AAACAACTGA GGATTTCATA TTGTGAAACA | 2947 |

-continued

| | |
|---|---|
| GGACAAGTCC ACGGCGTGTG CAGCTGCATG TAGAGCATAT | 2987 |
| TCAAAAGGCC TCGGAATTCC AATTTTCCAT TTGTAGAGTT | 3027 |
| AAACTTTGAA TGTGCCAAAC TTTTTCGTAA CTTTTGAATC | 3067 |
| TTAATATTTT GAAAGTCTTA AAGGAGACAC TGCAAAGTCT | 3107 |
| TAGACAATCT TTGGCATCTT AAAATAAAAT AGCAAACCAA | 3147 |
| CATTTTTTTT TCCAGAAAAT GGTAAGGTAC TCAGGAATCT | 3187 |
| GGAGACAAGA TATTGTAAGG AATGAACAAG GTTGCCACAG | 3227 |
| TGCATGGACC CAATTGTGTT TGCCTGTTGA CGTGCCATCA | 3267 |
| GTGCGTGATG TGGTATGACA TACACACACC AGAGCAACCG | 3307 |
| CCACACCAGA TATCGACAGA GTGGTCTTCT CTGCCTGAGA | 3347 |
| CCACCTCTCA CTACATCCAT TATCCCTTTG CCTTTAACCC | 3387 |
| TGACATTCAG TCTTAACACA TTTTATCTTA AATAATTTAT | 3427 |
| TCATTCCAGA ATGTCAAGGG TCCACTTGCT ATTTATTTTT | 3467 |
| TTTCAATTGT TGGTGCATTA ATTTAATAAT TCTTGTTTTT | 3507 |
| CACCTTCCTT CCCCGAAGAA CTTTTCCGTC CTTTTCACCT | 3547 |
| CCTTCTCCTG TGTACATAGT GATTTTATGT CCCCAGAACG | 3587 |
| CCTGGAAGCA TTTCTGAAAC CAAGATATTA TTAAAAACCT | 3627 |
| ATTATTGTTT TTAATCATGA GTATGTATCT GGCTGCAGGG | 3667 |
| CTGTGTATTG GGATATAGGT ATATAGTCTT ACACTTAAAC | 3707 |
| AGGTATGCCC CTGAGGTTCA CTGTGACCTC AAGTCTTTTG | 3747 |
| CCAGAATTTT CCCCTAATTC AGTTCACAAG TGGTAGGGTC | 3787 |
| TGCATCAGTG GCATTTCCCC CTGAATTCCA TTCAGCAGCA | 3827 |
| AGGTTCAACA GTGGTGACTG CCAGGCAGGA GAGTCCTGCG | 3867 |
| GCCAAACCTG AAGCCCAAGG CTCGTGGGCC ATGCAGGAAT | 3907 |
| CTCAGTGAAG CTGTCATGGG CTGGCACCTT TACACTGAGT | 3947 |
| TGCCTTGTCC CAGCTGGCAC ATCTAGGGAG TTCATTGCAA | 3987 |
| AATCCCCAGG ATGCAAAAAG CCACATGACA GCCTCAGAGC | 4027 |
| AAAGATGGTG GCAAATAGTC ATGATACATC TAGAGAATGA | 4067 |
| AAGAAAACTG TAAGGGAGGA GAAGGAGGGG AATACATTCC | 4107 |
| CTATATGGGA TGTTCCTACT GTTAACCTGT GGGAACAGAT | 4147 |
| AGCTCCGGGG GCAGCAGATG AGTTCCTCTG GCTGACTCTA | 4187 |
| TCTGTAGCCA CATGGGGACC TGCCTACGTG TGAACAAAAT | 4227 |
| GAACTGCACT TATCACACAA GGATTTCTTT GAAGACATGC | 4267 |
| TACTGGGGTG GGAAGCAGTG AGGTTTTATT CCCCATCTCC | 4307 |
| TAACTACAGG GAGCTCTGCC ATGTCATTTT GGCCTTCCTG | 4347 |
| AAACTAGGAC AGGTTGTCTA TCGGGGGGCT TCCCCCAGAG | 4387 |
| AGGTTTAGTG GGAGAATGTC AGTGAATGGG ATAGTTCACC | 4427 |
| TCATGGGACA ACCCAGAATC TGATCACCAG GACATAGGAA | 4467 |
| TGGCCCCATC AGATTTCCTG AGCCATTTTG TCACTTGGAA | 4507 |
| GAAAATAGTG TACCTTTGTA TTTATTTAAG AGTGCTCAAG | 4547 |

```
GCCTAATAGC AATAAACAGG TCTAGCCAAG AAATTACAAG                    4587

CTATTCTGTT AGCTGGGAGT GCTCTCTATA AGCTGATTAA                    4627

GGTACTGATA GGAACTCTTT GTTATTCATG TTGGTTGGGG                    4667

ATTAGAAATT TGTTTTTGTA CATTTATTTC AAATGAGGAG                    4707

GAGGTCATTT TTTCTCTCAA AAAATGAGTA TTTATTATTG                    4747

TCTTACTGAT TTCTTTGATT ATATACCTCT CCTCCTCAGT                    4787

TCACTCTTGT TTTTTTTCTT TCTCTTTGGC TTTTGCTTTT                    4827

GCTCTCTCTC ACTTCTTTCT TATTTTGTTG CATTGGTAGA                    4867

GTGTTGTATG GCTAGCATTG TATTGTATGT AATTAATTTT                    4907

GCACAAAAGC AAACATTTAG CATAGTAGGT TAATTTTGTT                    4947

TGTTTTTATG ACCATGCCAA AATAATATTC TGGGCTGGTG                    4987

GAGAACAAAG GACTATTCTT TAGGACTGAA ACTTGATTTT                    5027

GCTCATAGTA AGTAAAAAAA AAAA                                    5051

(2) INFORMATION FOR SEQ ID NO: 3:

(i) SEQUENCE CHARACTERISTICS:
        (A) LENGTH: 575 nucleotides
        (B) TYPE: nucleic acid
        (C) STRANDEDNESS: single
        (D) TOPOLOGY: linear (xi) SEQUENCE DESCRIPTION: SEQ ID NO: 3:

AA ATT GAG AAG CTC AAA CTT GAG ATT GAG AAA                     32
   Ile Glu Lys Leu Lys Leu Glu Ile Glu Lys
                 5                  10

CTG AAA GCT GAA TCT GGG AAT CCA TCT ATT                        62
Leu Lys Ala Glu Ser Gly Asn Pro Ser Ile
            15                  20

CGG CAG AAG ATA CGC TTA AAA GAT AAA GCA                        92
Arg Gln Lys Ile Arg Leu Lys Asp Lys Ala
            25                  30

GCA GAT GCC AAA AAA ATT CAG GAT CTG GAG                       122
Ala Asp Ala Lys Lys Ile Gln Asp Leu Glu
            35                  40

CGA CAA GTT AAG GAA ATG GAA GGG ATT CTG                       152
Arg Gln Val Lys Glu Met Glu Gly Ile Leu
            45                  50

AAG AGA AGA TAT CCC AAT TCT TTA CCT GCT                       182
Lys Arg Arg Tyr Pro Asn Ser Leu Pro Ala
            55                  60

TTA ATA TTG GCT GCA TCA GCA GCT GGT GAT                       212
Leu Ile Leu Ala Ala Ser Ala Ala Gly Asp
            65                  70

ACA GTG GAT AAA AAT ACA GTG GAA TTT ATG                       242
Thr Val Asp Lys Asn Thr Val Glu Phe Met
            75                  80

GAG AAA AGG ATA AAA AAG CTA GAA GCT GAT                       272
Glu Lys Arg Ile Lys Lys Leu Glu Ala Asp
            85                  90

CTG GAG GGC AAA GAT GAA GAT GCA AAG AAA                       302
Leu Glu Gly Lys Asp Glu Asp Ala Lys Lys
            95                 100

AGC CTT CGT ACC ATG GAA CAA CAG TTT CAG                       332
Ser Leu Arg Thr Met Glu Gln Gln Phe Gln
            105                110
```

```
AAA ATG AAG ATT CAG TAT GAA CAA AGA CTA                              362
Lys Met Lys Ile Gln Tyr Glu Gln Arg Leu
            115                 120

GAG CAG CAG GAG CAG CTA CTT GCC TGC AAA                              392
Glu Gln Gln Glu Gln Leu Leu Ala Cys Lys
            125                 130

TTG AAT CAA CAT GAC TCT CCC AGA ATT AAA                              422
Leu Asn Gln His Asp Ser Pro Arg Ile Lys
            135                 140

GCC CTA GAG AAG GAA CTT GAT GAC ATC AAG                              452
Ala Leu Glu Lys Glu Leu Asp Asp Ile Lys
            145                 150

GAA GCC CAT CAG ATC ACT GTA AGA AAC CTT                              482
Glu Ala His Gln Ile Thr Val Arg Asn Leu
            155                 160

GAA GCC GAA ATA GAC GTT CTT AAA CAT CAG                              512
Glu Ala Glu Ile Asp Val Leu Lys His Gln
            165                 170

AAT GCT GAA TTA GAC GTC AAG AAA AAT GAT                              542
Asn Ala Glu Leu Asp Val Lys Lys Asn Asp
            175                 180

AAA GAT GAT GAA GAT TTT CAG TCT ATA GAA                              572
Lys Asp Asp Glu Asp Phe Gln Ser Ile Glu
            185                 190

TTC                                                                  575
Phe (2) INFORMATION FOR SEQ ID NO: 4:

(i) SEQUENCE CHARACTERISTICS:
          (A) LENGTH: 794 nucleotides
          (B) TYPE: nucleic acid
          (C) STRANDEDNESS: single
          (D) TOPOLOGY: linear (xi) SEQUENCE DESCRIPTION: SEQ ID NO: 4:

GC GAT ACA CCG GGC GTT AAA GTG GGT GAT GAA                            32
   Asp Thr Pro Cys Val Lys Val Gly Asp Glu
            5                   10

GTG GAG GTA ATG GTT GTT GAA AAA GAA GAC                               62
Val Glu Val Met Val Val Glu Lys Glu Asp
            15                  20

CGT AAC GGC AAT TTA AAC CTA AGC CGT AAA                               92
Arg Asn Gly Asn Leu Asn Leu Ser Arg Lys
            25                  30

AGT GCC CGC ATT TTC CGT GCT TGG GAA AGA                              122
Ser Ala Arg Ile Phe Arg Ala Trp Glu Arg
            35                  40

ATT ATG GAA GTG CAT AAA ACA GGT GAA GTG                              152
Ile Met Glu Val His Lys Thr Gly Glu Val
            45                  50

GTT ACA GGT TTG GTT ACC AGC AAA ACA AAA                              182
Val Thr Gly Leu Val Thr Ser Lys Thr Lys
            55                  60

GGT GGC TTG ATT GTA GAT GTT TTC GGT ATG                              212
Gly Gly Leu Ile Val Asp Val Phe Gly Met
            65                  70

GAA ACT TTC TTA CCG GGT TCT CAA ATT GAT                              242
Glu Thr Phe Leu Pro Gly Ser Gln Ile Asp
            75                  80

GTT AAA CCC GTT ACA GAT TAC GAC CAG TTT                              272
```

```
                                          -continued

Val Lys Pro Val Thr Asp Tyr Asp Gln Phe
            85                  90

GTT GGT AAA ACA ATG GAG TTT AAA GTT GTT                    302
Val Gly Lys Thr Met Glu Phe Lys Val Val
            95                 100

AAG ATT AAC GAA ACA ATT AAG AAT GCT GTT                    332
Lys Ile Asn Glu Thr Ile Lys Asn Ala Val
           105                 110

GTA TCT CAC AAA GCA TTA ATT GAA AGC GAT                    362
Val Ser His Lys Ala Leu Ile Glu Ser Asp
           115                 120

ATT GAA GCA CAA CGT GCT GAA ATA ATG AGC                    392
Ile Glu Ala Gln Arg Ala Glu Ile Met Ser
           125                 130

AAA TTA GAA AAA GGT CAG GTG TTA GAA GGT                    422
Lys Leu Glu Lys Gly Gln Val Leu Glu Gly
           135                 140

ACT GTT AAG AAC ATT ACA GAC TTC GGT GCA                    452
Thr Val Lys Asn Ile Thr Asp Phe Gly Ala
           145                 150

TTT ATG GAC CTT GGT GGC TTA GAC GGC TTA                    482
Phe Met Asp Leu Gly Gly Leu Asp Gly Leu
           155                 160

TTA TAC ATT ACA GAT ATT TCA TGG GGC AGA                    512
Leu Tyr Ile Thr Asp Ile Ser Trp Gly Arg
           165                 170

ATT TCT CAC CCA AGC GAA GTA TTG AAA ATG                    542
Ile Ser His Pro Ser Glu Val Leu Lys Met
           175                 180

GAT CAG AAA TTA AAT GTG GTT GTA TTA GAC                    572
Asp Gln Lys Leu Asn Val Val Val Leu Asp
           185                 190

TTT GAT GAT GAT AAA AAA CGT ATC AGC CTT                    602
Phe Asp Asp Asp Lys Lys Arg Ile Ser Leu
           195                 200

GGT TTA AAA CAA TTA ACA CCG CAT CCT TGG                    632
Gly Leu Lys Gln Leu Thr Pro His Pro Trp
           205                 210

GAA GTA TTA CCT GAA GGT TTG GCT GAA GGT                    662
Glu Val Leu Pro Glu Gly Leu Ala Glu Gly
           215                 220

GCT ATT GTA AAA GGT AAA GTG GTA AAT ATT                    692
Ala Ile Val Lys Gly Lys Val Val Asn Ile
           225                 230

GAA GAT TAC GGT GCA TTC TTA GAA ATT CAA                    722
Glu Asp Tyr Gly Ala Phe Leu Glu Ile Gln
           235                 240

CCG GGG GTT GAA GGT TTG GTT CAC GTA AGT                    752
Pro Gly Val Glu Gly Leu Val His Val Ser
           245                 250

GAA ATT ACC TGG GAA AAT ACA CCA ATC AAC                    782
Glu Ile Thr Trp Glu Asn Thr Pro Ile Asn
           255                 260

GCT AAA GAA TTC                                            794
Ala Lys Glu Phe (2) INFORMATION FOR SEQ ID NO: 5:

(i) SEQUENCE CHARACTERISTICS:
        (A) LENGTH: 1570 nucleotides
        (B) TYPE: nucleic acid
```

(C) STRANDEDNESS: single
(D) TOPOLOGY: linear (xi) SEQUENCE DESCRIPTION: SEQ ID NO: 5:

```
  G GAT GGC TCC CCC AAC ACC CCC TTC CGT AAG                     31
    Asp Gly Ser Pro Asn Thr Pro Phe Arg Lys
                  5                      10

GAC CTC ATC AGC CTG GAC TCA TCC CCA GCC                         61
Asp Leu Ile Ser Leu Asp Ser Ser Pro Ala
             15                      20

AAG GAG CGG CTG GAG GAC GGC TGT GTG CAC                         91
Lys Glu Arg Leu Glu Asp Gly Cys Val His
             25                      30

CCA CTG GAG GAA GCC ATG CTG AGC TGC GAC                        121
Pro Leu Glu Glu Ala Met Leu Ser Cys Asp
             35                      40

ATG GAT GGC TCC CGC CAC TTC CCC GAG TCC                        151
Met Asp Gly Ser Arg His Phe Pro Glu Ser
             45                      50

CGA AAC AGC AGC CAC ATC AAG AGG CCC ATG                        181
Arg Asn Ser Ser His Ile Lys Arg Pro Met
             55                      60

AAC GCC TTC ATG GTG TGG GCC AAG GAT GAG                        211
Asn Ala Phe Met Val Trp Ala Lys Asp Glu
             65                      70

CGG AGG AAG ATC CTG CAA GCC TTC CCA GAC                        241
Arg Arg Lys Ile Leu Gln Ala Phe Pro Asp
             75                      80

ATG CAC AAC TCC AGC ATC AGC AAG ATC CTT                        271
Met His Asn Ser Ser Ile Ser Lys Ile Leu
             85                      90

GGA TCT CGC TGG AAG TCC ATG ACC AAC CAG                        301
Gly Ser Arg Trp Lys Ser Met Thr Asn Gln
             95                     100

GAG AAG CAG CCC TAC TAT GAG GAA CAG GCT                        331
Glu Lys Gln Pro Tyr Tyr Glu Glu Gln Ala
            105                     110

CTG CTG ATC GTC ATC ACC TGG AGA AGT ATC                        361
Leu Leu Ile Val Ile Thr Trp Arg Ser Ile
            115                     120

CTG ACT ACA AGT ACA AGC CGC GGC CAA GCG                        391
Leu Thr Thr Ser Thr Ser Arg Gly Gln Ala
            125                     130

CAC CTG CAT CGT GGA GGG CAA GCG GCT GCG                        421
His Leu His Arg Gly Gly Gln Ala Ala Ala
            135                     140

CGT GGG AGA GTA CAA GGC CCT GAT GAG GAC                        451
Arg Gly Arg Val Gln Gly Pro Asp Glu Asp
            145                     150

CCG GCG TCA GGA TGC CCG CCA GAG CTA CGT                        481
Pro Ala Ser Gly Cys Pro Pro Glu Leu Arg
            155                     160

GAT CCC CCC GCA GGC TGG CCA GGT GCA GAT                        511
Asp Pro Pro Ala Gly Trp Pro Gly Ala Asp
            165                     170

GAG CTC CTC AGA TGT CCT GTA CCC TCG GGC                        541
Glu Leu Leu Arg Cys Pro Val Pro Ser Gly
            175                     180

AGC AGG CAT GCC GCT GCA CAG CCA CTG GTG                        571
Ser Arg His Ala Ala Ala Gln Pro Leu Val
            185                     190
```

```
GAG CAC TAT GTC CCT CGT AGC CTG GAC CCC                                    601
Glu His Tyr Val Pro Arg Ser Leu Asp Pro
            195                 200

AAC ATG CCT GTG ATC GTC AAC ACC TGC AGC                                    631
Asn Met Pro Val Ile Val Asn Thr Cys Ser
            205                 210

CTC AGA GAG GAG GGT GAG GGC ACA GAT GAC                                    661
Leu Arg Glu Glu Gly Glu Gly Thr Asp Asp
            215                 220

AGG CAC TCG GTG GCT GAT GGC GAG ATG TAC                                    691
Arg His Ser Val Ala Asp Gly Glu Met Tyr
            225                 230

CGG TAC AGC GAG GAC GAG GAC TCG GAG GGT                                    721
Arg Tyr Ser Glu Asp Glu Asp Ser Glu Gly
            235                 240

GAA GAG AAG AGC GAT GGG GAG TTG GTG GTG                                    751
Glu Glu Lys Ser Asp Gly Glu Leu Val Val
            245                 250

CTC ACA GAC TGATCCCGGC TGGGTGGCCT                                          780
Leu Thr Asp

GGCCCCTTCT CCTCTGGGGA AGACCTTGTC CCAACTCGAT                                820

GGGCAAAGCT AGCCAACCTA AGACTATGTT GGTACTTGGA                                860

CTTGTTCGTG CCCCAGAGAT GGGCAAAGCT GTGCACTTGC                                900

AGATACATTC ATGAGGGGAG AGGCTCTCTC CCTTCCTGAG                                940

GAGCTGTTGG CCTGGGTGGG CAGGAACTGC AGTATGGCCA                                980

TGGGCTGAGC AGGCTGAGCA CCTCAGCCTT TAGGGCTTAT                               1020

GGCCAGGGGA CACTGTATGA CTCTCCTCTC CTGCAGGTGT                               1060

CTATCCACCT GGGGTATGGC ATCTACCGAC CTGTCTCCCT                               1100

GGGGTCACAT GCTTTGTTTC CATTCTTGTC CTGGCTGGAC                               1140

CAGCCACTGT GGGACCAACA CCCCTCCCAC ACTCCCCCAG                               1180

ACTGCTCGTC TATCACCAGG ATCGCTTTGT ACTTTGTGCA                               1220

AAAGGGTCTG GCTGTCCCTT GCTGTTTTCA TCTCTGCCAA                               1260

GCCTATTGTG CCTCTGGCTG CTGTATGTGT GCGCGTGCAC                               1300

GTGTGTGTGT TTCATCTGTT CATTCACTGC ACAAGATATT                               1340

TATTGAGTGC CCACTACGTG CCAGGCACTG TTGCTGAGTT                               1380

CCTGTGGGTG TGTCTCTCGA TGCCACTCCT GCTTCTCTGG                               1420

GGGCCTCTTT CTGTGCTTCT CTTTGTCCCC AAATTGCTAC                               1460

CTCTTTGTCA GTCTGGGTGT CTCAGGTTCT GTGTGTCCTT                               1500

GTGTGCATTT CTGTCTCTCT CTGTCCTCGT CTCTCTGCAA                               1540

GGCCCTCTAT TTCTCTCTTT CTTGGTGTCT                                          1570

(2) INFORMATION FOR SEQ ID NO: 6:

(i) SEQUENCE CHARACTERISTICS:
        (A) LENGTH: 3243 nucleotides
        (B) TYPE:  nucleic acid
        (C) STRANDEDNESS: single
        (D) TOPOLOGY: linear (xi) SEQUENCE DESCRIPTION:  SEQ ID NO: 6:

CCAGAACCCA AGAGACCAGG AGTGTCGGAG GCTGCCTCTG                                 40
```

```
GAAGCCAGGA GAAGCTGGAC TTCAACCGAA ATTTGAAAGA                    80

AGTGGTGCCA GCCATAGAGA AGCTGTTGTC CAGTGACTGG                   120

AAGGAGAGGT TTCTAGGAAG GAACTCTATG GAAGCCAAAG                   160

ATGTCAAAGG GACCCAAGAG AGCCTAGCAG AGAAGGAGCT                   200

CCAGCTTCTG GTCATGATTC ACCAGCTGTC CACCCTGCGG                   240

GACCAGCTCC TGACAGCCCA CTCGGAGCAG AAGAACATGG                   280

CTGCCATGCT GTTTGAGAAG CAGCAGCAGC AGATGGAGCT                   320

TGCCCGGCAG CAGCAGGAGC AGATTGCAAA GCAGCAGCAG                   360

CAGCTGATTC AGCAGCAGCA TAAGATCAAC CTCCTTCAGC                   400

AGCAGATCCA GCAGGTTAAC ATGCCTTATG TCATGATCCC                   440

AGCCTTCCCC CCAAGCCACC AACCTCTGCC TGTCACCCCT                   480

GACTCCCAGC TGGCCTTACC CATTCAGCCC ATTCCCTGCA                   520

AACCAGTGGA GTATCCGCTG CAGCTGCTGC ACAGCCCCCC                   560

TGCCCCAGTG GTGAAGAGGC CTGGGGCATG GCACCCACCA                   600

CCCCCTGCAG GAGCCCTCCC AGCCCCTGAA CCTCACAGCC                   640

AAGCCCAAGG CCCCCGAGCT GCCCAACACC TCCAGCTCCC                   680

CAAGCCTGAA G ATG AGC AGC TGT GTG CCC CGC CCC                  715
             Met Ser Ser Cys Val Pro Arg Pro
                              5

CCC AGC CAT GGA GGC CCC ACG CGG GAC CTG                       745
Pro Ser His Gly Gly Pro Thr Arg Asp Leu
 10                  15

CAG TCC AGC CCC CCG AGC CTG CCT CTG GGC                       775
Gln Ser Ser Pro Pro Ser Leu Pro Leu Gly
 20                  25

TTC CTT GGT GAA GGG GAC GCT GTC ACC AAA                       805
Phe Leu Gly Glu Gly Asp Ala Val Thr Lys
 30                  35

GCC ATC CAG GAT GCT CGG CAG CTG CTG CAC                       835
Ala Ile Gln Asp Ala Arg Gln Leu Leu His
 40                  45

AGC CAC AGT GGG GCC TTG GAT GGC TCC CCC                       865
Ser His Ser Gly Ala Leu Asp Gly Ser Pro
 50                  55

AAC ACC CCC TTC CGT AAG GAC CTC ATC AGC                       895
Asn Thr Pro Phe Arg Lys Asp Leu Ile Ser
 60                  65

CTG GAC TCA TCC CCA GCC AAG GAG CGG CTG                       925
Leu Asp Ser Ser Pro Ala Lys Glu Arg Leu
 70                  75

GAG GAC GGC TGT GTG CAC CCA CTG GAG GAA                       955
Glu Asp Gly Cys Val His Pro Leu Glu Glu
 80                  85

GCC ATG CTG AGC TGC GAC ATG GAT GGC TCC                       985
Ala Met Leu Ser Cys Asp Met Asp Gly Ser
 90                  95

CGC CAC TTC CCC GAG TCC CGA AAC AGC AGC                      1015
Arg His Phe Pro Glu Ser Arg Asn Ser Ser
100                  105

CAC ATC AAG AGG CCC ATG AAC GCC TTC ATG                      1045
His Ile Lys Arg Pro Met Asn Ala Phe Met
110                  115
```

```
GTG TGG GCC AAG GAT GAG CGG AGG AAG ATC                    1075
Val Trp Ala Lys Asp Glu Arg Arg Lys Ile
120                 125

CTG CAA GCC TTC CCA GAC ATG CAC AAC TCC                    1105
Leu Gln Ala Phe Pro Asp Met His Asn Ser
130                 135

AGC ATC AGC AAG ATC CTT GGA TCT CGC TGG                    1135
Ser Ile Ser Lys Ile Leu Gly Ser Arg Trp
140                 145

AAG TCC ATG ACC AAC CAG GAG AAG CAG CCC                    1165
Lys Ser Met Thr Asn Gln Glu Lys Gln Pro
150                 155

TAC TAT GAG GAA CAG GCG CGG CTG AGC CGG                    1195
Tyr Tyr Glu Glu Gln Ala Arg Leu Ser Lys
160                 165

CAG CAC CTG GAG AAG TAT CCT GAC TAC AAG                    1225
Gln His Leu Glu Lys Tyr Pro Asp Tyr Lys
170                 175

TAC AAG CCG CGG CCC AAG CGC ACC TGC ATC                    1255
Tyr Lys Pro Arg Pro Lys Arg Thr Cys Ile
180                 185

GTG GAG GGC AAG CGG CTG CGC GTG GGA GAG                    1285
Val Glu Gly Lys Arg Leu Arg Val Gly Glu
190                 195

TAC AAG GCC CTG ATG AGG ACC CGG CGT CAG                    1315
Tyr Lys Ala Leu Met Arg Thr Arg Arg Gln
200                 205

GAT GCC CGC CAG AGC TAC GTG ATC CCC CCG                    1345
Asp Ala Arg Gln Ser Tyr Val Ile Pro Pro
210                 215

CAG GCT GGC CAG GTG CAG ATG AGC TCC TCA                    1375
Gln Ala Gly Gln Val Gln Met Ser Ser Ser
220                 225

GAT GTC CTG TAC CCT CGG GCA GCA GGC ATG                    1405
Asp Val Leu Tyr Pro Arg Ala Ala Gly Met
230                 235

CCG CTG GCA CAG CCA CTG GTG GAG CAC TAT                    1435
Pro Leu Ala Gln Pro Leu Val Glu His Tyr
240                 245

GTC CCT CGT AGC CTG GAC CCC AAC ATG CCT                    1465
Val Pro Arg Ser Leu Asp Pro Asn Met Pro
250                 255

GTG ATC GTC AAC ACC TGC AGC CTC AGA GAG                    1495
Val Ile Val Asn Thr Cys Ser Leu Arg Glu
260                 265

GAG GGT GAG GGC ACA GAT GAC AGG CAC TCG                    1525
Glu Gly Glu Gly Thr Asp Asp Arg His Ser
270                 275

GTG GCT GAT GGC GAG ATG TAC CGG TAC AGC                    1555
Val Ala Asp Gly Glu Met Tyr Arg Tyr Ser
280                 285

GAG GAC GAG GAC TCG GAG GGT GAA GAG AAG                    1585
Glu Asp Glu Asp Ser Glu Gly Glu Glu Lys
290                 295

AGC GAT GGG GAG TTG GTG GTG CTC ACA GAC                    1615
Ser Asp Gly Glu Leu Val Val Leu Thr Asp
300                 305

TGATCCCGGC TGGGTGGGCC TGGCCCCTTC TCCTCTGGGG                 1655

AAGACCTTGT CCCAACTCGA TGGGCACAGC CAGCCAACCT                 1695
```

| | |
|---|---|
| AAGACTATGT TGGTACTTGG ACTTGTTCGT GCCCCAGAGA | 1735 |
| TGGGCAAAGC TGTGCACTTG CAGATACATT CATGAGGGGA | 1775 |
| GAGGCGCCCT CCCTTCCTGA GGAGCTGTTG GCCTGGGTGG | 1815 |
| GCAGGAACTG CAGTATGGCC ATGGGCTGAG CAGGCTGAGC | 1855 |
| ACCTCAGCCT TTAGGGCTTA TGGCCAGGGG ACACTGTATG | 1895 |
| ACTCTCCTCT CCTGCAGGTG TCTATCCACC TGGGGTATGG | 1935 |
| CATCTACCGA CCTGTCTCCC TGGGGTCACA TGCTTTGTTT | 1975 |
| CCATTCTTGT CCTGGCTGGA CCAGCCACTG TGGGACCAAC | 2015 |
| ACCCCTCCCA CACTCCCCCA GACTGCTCGT CTATCACCAG | 2055 |
| GATCGCTTTG TACTTTGTGC AAAAGGGTCT GGCTGTCCCT | 2095 |
| TGCTGTTTTC ATCTCTGCCA AGCCTATTGT GCCTCTGGCT | 2135 |
| GCTGTATGTG TGCGCGTGCA CGTGTGTGTG TTTCATCTGT | 2175 |
| TCATTCACTG CACAAGATAT TTATTGAGTG CCCACTACGT | 2215 |
| GCCAGGCACT GTTGCTGAGT TCCTGTGGGT GTGTCTCTCG | 2255 |
| ATGCCACTCC TGCTTCTCTG GGGGCCTCTT TCTGTGCTTC | 2295 |
| TCTTTGTCCC CAAATTGCTA CCTCTTTGTC AGTCTGGGTG | 2335 |
| TCTCAGGTTC TGTGTGTCCT TGTGTGCATT TCTGTCTCTC | 2375 |
| TCTGTCCTCG TCTCTCTGCA AGGCCCTCTA TTTCTCTCTT | 2415 |
| TCTTGGTGTC TGTCCTTTGC CCCCTGTGCC CTCTGGATTC | 2455 |
| TCTGGGTCTA TGTAGGCCCC TGGTCTGCCC TGGGCTCATC | 2495 |
| AGCCTTCCTG ACCTCCTCCT GCCCTCCCCT TCACTCCCTC | 2535 |
| CCTGGCTCTG CCAGTCGGTT CCCACGGAGC CATTTTTAGC | 2575 |
| TCTGATCAGC ATGGGAATGT GCCTCGGCCT CCAAGGGGCT | 2615 |
| TTGTCCTGGT GCCCCCGCCC CTGGTCCCAA CCTGATCCCA | 2655 |
| CGAGGGAGTT GGGACAGGAG GATTGATGGT GCTCCCCTTC | 2695 |
| CTGCCAGCGT CAGAGGCCCT GGAGAGGGGC TGTCCATGGC | 2735 |
| AGCTGGTCTT TATTCCTCCC TCATGAGCAC AGGGTCGGGG | 2775 |
| GGGTCCCCAT TCTTGGAAGA GGTTGAGAAG ACTCCTGGGC | 2815 |
| TTCAGCCTCT CCCACCCAGC CCTGCCCCCT CACCTGCCTG | 2855 |
| CCCTCCCCTC CCCCCACTCT ATACTAGGGA CTGGATCTCA | 2895 |
| GCTCTGATCA GTTTCACAAA GTTTGTTCCC TAAGGAAATC | 2935 |
| AAATCCCATT GTCACCTAAC TCTGAAGATC TAAATAGCCC | 2975 |
| TTGGATCAGT ACGGGAACCC CAAATCCCAC AGGGCCAGAT | 3015 |
| GTGGAGTCTG TGTCTGCCCC CGTCTTCTCT CCATCCTCAA | 3055 |
| AGCCCCCACT TCTCTCCAGG CTGTTTCTTT TTTTATGACT | 3095 |
| GTAAACATAG ATAGTGCTTT ATTTGTTAA TAATAAGATA | 3135 |
| ATGATGAGTA ACTTAACCAG CACATTTCTC CTGTTTACAC | 3175 |
| TCGGGGATT TTTTTGTTTT CTGATGACAT AATAAAGACA | 3215 |
| GATCATTTCA GAAAAAAAAA AAAAAAAA | 3243 |

-continued (2) INFORMATION FOR SEQ ID NO: 7:

(i) SEQUENCE CHARACTERISTICS:
        (A) LENGTH: 2599 nucleotides
        (B) TYPE: nucleic acid
        (C) STRANDEDNESS: single
        (D) TOPOLOGY: linear (xi) SEQUENCE DESCRIPTION: SEQ ID NO: 7:

```
GCTGCCTTCA GTCCCTAGTG TCTGGGTCCC CGCCCTCCAG                          40

CCGCCTTTGA GTCGTGCCTG GGTCCTCGCC CTTGCCTCAG                          80

AACCGCGAAG AAAGGAAGCT CGCGTGTTTG CTAGAAAACC                         120

TAGTTGGGAG TGCGAGGCAG AGAACGTTCA GCACCTTTGT                         160

TCCTCCCGAA CCCTCGGGAC AGAGGCAGGG TTCTGAGGGC                         200

AGGGATTCCC CCTCGTCTTG GCCCCACCGC CCGGGCTGGG                         240

CACTAAACTC GGGCCGCGGC GGGGCGAGCG AGGCGGGCTC                         280

CGGAGGGAGC TGACGCCTG ATG ATG GCG CAG TCC                            314
                     Met Met Ala Gln Ser
                                     5

AAC ATG TTT ACC GTG GCT GAT GTG TTG AGT                             344
Asn Met Phe Thr Val Ala Asp Val Leu Ser
         10                  15

CAA GAT GAA CTG CGC AAA AAG CTA TAC CAG                             374
Gln Asp Glu Leu Arg Lys Lys Leu Tyr Gln
             20                  25

ACG TTT AAG GAT CGG GGT ATA CTG GAT ACA                             404
Thr Phe Lys Asp Arg Gly Ile Leu Asp Thr
         30                      35

CTC AAG ACA CAA CTT CGA AAC CAG CTA ATT                             434
Leu Lys Thr Gln Leu Arg Asn Gln Leu Ile
             40                  45

CAT GAG TTG ATG CAC CCT GTA TTG AGT GGA                             464
His Glu Leu Met His Pro Val Leu Ser Gly
             50                  55

GAA CTG CAG CCT CGG TCC ATT TCA GTA GAA                             494
Glu Leu Gln Pro Arg Ser Ile Ser Val Glu
             60                  65

GGG AGC TCC CTC TTA ATA GGC GCC TCT AAC                             524
Gly Ser Ser Leu Leu Ile Gly Ala Ser Asn
             70                  75

TCT TTA GTG GCA GAT CAC TTA CAA AGA TGT                             554
Ser Leu Val Ala Asp His Leu Gln Arg Cys
             80                  85

GGC TAT GAA TAT TCA CTT TCT GTT TTC TTT                             584
Gly Tyr Glu Tyr Ser Leu Ser Val Phe Phe
             90                  95

CCA GAA AGT GGT TTG GCA AAA GAA AAG GTA                             614
Pro Glu Ser Gly Leu Ala Lys Glu Lys Val
             100                 105

TTT ACT ATG CAG GAT CTA TTA CAA CTC ATT                             644
Phe Thr Met Gln Asp Leu Leu Gln Leu Ile
             110                 115

AAA ATC AAC CCT ACT TCC AGT CTC TAC AAA                             674
Lys Ile Asn Pro Thr Ser Ser Leu Tyr Lys
             120                 125

TCA CTG GTT TCA GGA TCT GAT AAA GAA AAT                             704
Ser Leu Val Ser Gly Ser Asp Lys Glu Asn
             130                 135
```

-continued

| | |
|---|---|
| CAA AAA GGT TTT CTT ATG CAT TTT TTA AAA<br>Gln Lys Gly Phe Leu Met His Phe Leu Lys<br>              140                   145 | 734 |
| GAA TTG GCA GAA TAT CAT CAA GCT AAA GAG<br>Glu Leu Ala Glu Tyr His Gln Ala Lys Glu<br>              150                   155 | 764 |
| AGT TGT AAT ATG GAA ACT CAG ACA AGT TCG<br>Ser Cys Asn Met Glu Thr Gln Thr Ser Ser<br>              160                   165 | 794 |
| ACA TTT AAC AGA GAT TCT CTG GCT GAG AAG<br>Thr Phe Asn Arg Asp Ser Leu Ala Glu Lys<br>              170                   175 | 824 |
| CTT CAG CTT ATT GAT GAT CAG TTT GCA GAT<br>Leu Gln Leu Ile Asp Asp Gln Phe Ala Asp<br>              180                   185 | 854 |
| GCT TAC CCT CAG CGT ATC AAG TTC GAA TCT<br>Ala Tyr Pro Gln Arg Ile Lys Phe Glu Ser<br>              190                   195 | 884 |
| TTA GAA ATA AAG CTA AAT GTG TAT AAG AGA<br>Leu Glu Ile Lys Leu Asn Val Tyr Lys Arg<br>              200                   205 | 914 |
| GAA ATA GAA GAG CAA CTT CGG GCA GAA ATG<br>Glu Ile Glu Glu Gln Leu Arg Ala Glu Met<br>              210                   215 | 944 |
| TGT CAA AAG TTG AAG TTT TTT AAA GAT ACC<br>Cys Gln Lys Leu Lys Phe Phe Lys Asp Thr<br>              220                   225 | 974 |
| GAG ATA GCA AAA ATT AAA ATG GAA GCA AAA<br>Glu Ile Ala Lys Ile Lys Met Glu Ala Lys<br>              230                   235 | 1004 |
| AAA AAG TAT GAA AAG GAG TTA ACC ATG TTC<br>Lys Lys Tyr Glu Lys Glu Leu Thr Met Phe<br>              240                   245 | 1034 |
| CAG AAT GAT TTT GAA AAA GCT TGT CAA GCA<br>Gln Asn Asp Phe Glu Lys Ala Cys Gln Ala<br>              250                   255 | 1064 |
| AAA TCT GAA GCT CTC GTT CTT CGG GAA AAG<br>Lys Ser Glu Ala Leu Val Leu Arg Glu Lys<br>              260                   265 | 1094 |
| AGT ACC CTT GAA AGA ATT CAC AAG CAC CAA<br>Ser Thr Leu Glu Arg Ile His Lys His Gln<br>              270                   275 | 1124 |
| GAG ATT GAA ACA AAA GAA ATT TAT GCT CAA<br>Glu Ile Glu Thr Lys Glu Ile Tyr Ala Gln<br>              280                   285 | 1154 |
| AGG CAA CTT TTA CTA AAA GAT ATG GAT TTG<br>Arg Gln Leu Leu Leu Lys Asp Met Asp Leu<br>              290                   295 | 1184 |
| CTA AGA GGA AGA GAA GCA GAG CTG AAG CAA<br>Leu Arg Gly Arg Glu Ala Glu Leu Lys Gln<br>              300                   305 | 1214 |
| AGA GTT GAA GCT TTT GAA TTG AAC CAG AAG<br>Arg Val Glu Ala Phe Glu Leu Asn Gln Lys<br>              310                   315 | 1244 |
| CTC CAG GAA GAA AAA CAT AAA AGC ATA ACT<br>Leu Gln Glu Glu Lys Met Lys Ser Ile Thr<br>              320                   325 | 1274 |
| GAG GCA CTT AGG AGA CAG GAG CAG AAT ATA<br>Glu Ala Leu Arg Arg Gln Glu Gln Asn Ile<br>              330                   335 | 1304 |

-continued

| | |
|---|---|
| AAG AGT TTT GAG GAG ACC TAT GAC CGA AAG<br>Lys Ser Phe Glu Glu Thr Tyr Asp Arg Lys<br>340                            345 | 1334 |
| CTC AAG AAT GAA CTT CTA AAG TAT CAA CTT<br>Leu Lys Asn Glu Leu Leu Lys Tyr Gln Leu<br>350                            355 | 1364 |
| GAA CTG AAG GAT GAC TAC ATC ATT AGA ACT<br>Glu Leu Lys Asp Asp Tyr Ile Ile Arg Thr<br>360                            365 | 1394 |
| AAT CGA CTG ATT GAA GAT GAA AGG AAG AAT<br>Asn Arg Leu Ile Glu Asp Glu Arg Lys Asn<br>370                            375 | 1424 |
| AAA GAA AAA GCT GTT CAT TTG CAA GAG GAG<br>Lys Glu Lys Ala Val His Leu Gln Glu Glu<br>380                            385 | 1454 |
| CTC ATA GCT ATT AAT TCA AAA AAG GAG GAA<br>Leu Ile Ala Ile Asn Ser Lys Lys Glu Glu<br>390                            395 | 1484 |
| CTC AAT CAA TCT GTA AAT CGT GTG AAA GAA<br>Leu Asn Gln Ser Val Asn Arg Val Lys Glu<br>400                            405 | 1514 |
| CTT GAG CTT GAA TTA GAG TCT GTC AAA GCC<br>Leu Glu Leu Glu Leu Glu Ser Val Lys Ala<br>410                            415 | 1544 |
| CAG TCT TTG GCA ATA ACA AAA CAA AAC CAT<br>Gln Ser Leu Ala Ile Thr Lys Gln Asn His<br>420                            425 | 1574 |
| ATG CTG AAT GAA AAG GTT AAA GAG ATG AGT<br>Met Leu Asn Glu Lys Val Lys Glu Met Ser<br>430                            435 | 1604 |
| GAT TAT TCA CTA CTA AAA GAA GAG AAA CTG<br>Asp Tyr Ser Leu Leu Lys Glu Glu Lys Leu<br>440                            445 | 1634 |
| GAG CTT CTG GCA CAA AAT AAA TTA CTT AAA<br>Glu Leu Leu Ala Gln Asn Lys Leu Leu Lys<br>450                            455 | 1664 |
| CAA CAA CTG GAA GAG AGT AGA AAT GAA AAC<br>Gln Gln Leu Glu Glu Ser Arg Asn Glu Asn<br>460                            465 | 1694 |
| CTG CGT CTC CTA AAC CGC CTA GCT CAG CCG<br>Leu Arg Leu Leu Asn Arg Leu Ala Gln Pro<br>470                            475 | 1724 |
| GCT CCT GAA CTT GCA GTC TTT CAG AAA GAA<br>Ala Pro Glu Leu Ala Val Phe Gln Lys Glu<br>480                            485 | 1754 |
| CTA CGG AAA GCC GAA AAG GCT ATA GTG GTT<br>Leu Arg Lys Ala Glu Lys Ala Ile Val Val<br>490                            495 | 1784 |
| GAG CAT GAG GAG TTC GAA AGC TGC AGG CAA<br>Glu His Glu Glu Phe Glu Ser Cys Arg Gln<br>500                            505 | 1814 |
| GCT CTG CAC AAA CAA CTG CAA GAC GAA ATT<br>Ala Leu His Lys Gln Leu Gln Asp Glu Ile<br>510                            515 | 1844 |
| GAG CAT TCT GCA CAG CTG AAG GCC CAG ATT<br>Glu His Ser Ala Gln Leu Lys Ala Gln Ile<br>520                            525 | 1874 |
| CTA GGT TAC AAA GCT TCT GTA AAG AGT TTA<br>Leu Gly Tyr Lys Ala Ser Val Lys Ser Leu<br>530                            535 | 1904 |

```
ACT ACT CAG GTT GCC GAT TTA AAA TTG CAA                         1934
Thr Thr Gln Val Ala Asp Leu Lys Leu Gln
            540                 545

CTG AAG CAA ACT CAG ACA GCC CTA GAG AAT                         1964
Leu Lys Gln Thr Gln Thr Ala Leu Glu Asn
            550                 555

GAA GTG TAC TGC AAT CCA AAG CAG TCT GTG                         1994
Glu Val Tyr Cys Asn Pro Lys Gln Ser Val
            560                 565

ATC GAT CGT TCT GTC AAT GGA TTA ATA AAT                         2024
Ile Asp Arg Ser Val Asn Gly Leu Ile Asn
            570                 575

GGC AAT GTG GTG CCT TGC AAT GGT GAG ATA                         2054
Gly Asn Val Val Pro Cys Asn Gly Glu Ile
            580                 585

AGT GGG GAT TTC TTG AAC AAT CCT TTT AAA                         2084
Ser Gly Asp Phe Leu Asn Asn Pro Phe Lys
            590                 595

CAG GAA AAC GTT CTA GCA CGT ATG GTT GCA                         2114
Gln Glu Asn Val Leu Ala Arg Met Val Ala
            600                 605

TCA AGG ATC ACA AAT TAT CCA ACT GCA TGG                         2144
Ser Arg Ile Thr Asn Tyr Pro Thr Ala Trp
            610                 615

GTG GAG GGT AGT TCC CCT GAT TCT GAC CTT                         2174
Val Glu Gly Ser Ser Pro Asp Ser Asp Leu
            620                 625

AAT ACT AAG GCA AGG GTC AAA GAG CTT CAG                         2204
Asn Thr Lys Ala Arg Val Lys Glu Leu Gln
            630                 635

CAA GAG GCC GAA CGC TTG GAA AAG GCT TTC                         2234
Gln Glu Ala Glu Arg Leu Glu Lys Ala Phe
            640                 645

AGA AGT TAC CAT CGG AGA GTC ATT AAA AAC                         2264
Arg Ser Tyr His Arg Arg Val Ile Lys Asn
            650                 655

TCT GCC AAA AGC CCA CTA GCA GCA AAG AGC                         2294
Ser Ala Lys Ser Pro Lys Ala Ala Lys Ser
            660                 665

CCA CCT CTC TGC ACT TGC TGG AAG CCT TCA                         2324
Pro Pro Leu Cys Thr Cys Trp Lys Pro Ser
            670                 675

AAA ACA TTA CTT CCA GTT CCC CGG AAA GAC                         2354
Lys Thr Leu Leu Pro Val Pro Arg Lys Asp
            680                 685

ATA TTT TTG GAG AGG ACA GAG TTG TCT CTG                         2384
Ile Phe Leu Glu Arg Thr Glu Leu Ser Leu
            690                 695

AGC AGC CTC AAG TGG GCA CAC TTG AAG AAA                         2414
Ser Ser Leu Lys Trp Ala His Leu Lys Lys
            700                 705

GGA ATG ACG TCG TGG AAG CAC TGACAGGCAG                          2445
Gly Met Thr Ser Trp Lys His
            710

TGCAGCCTCG AGGCTCCGCG GGGGCACTTC CTCCAGACGC                     2485

CTCTCTTCCA CACCCCTTCC AAAAGCAAAA AGAAGCCTCG                     2525

AAAGTGAAAT GTATCTGGAA GGTCTGGGCA GATCACACAT                     2565

TGCTTCCCCC AGTCCTTGTC CTGACAGAAT GCCC                           2599
```

(2) INFORMATION FOR SEQ ID NO: 8:

(i) SEQUENCE CHARACTERISTICS:
        (A) LENGTH: 346 nucleotides
        (B) TYPE: nucleic acid
        (C) STRANDEDNESS: single
        (D) TOPOLOGY: linear (xi) SEQUENCE DESCRIPTION: SEQ ID NO: 8:

```
TCGACCTTCG CCTTCAATGG GCTGGCCAGT GGGGGAGAAC                40

CGGGGAGGTC GGGGAAGAAT CGCTTCCACT CGGAGTGGGG                80

GGGCGGCTCA CTCCAGGCGA TACAGGCACA GGCAAAGGAG               120

GGAAGCAAAC AAGGACATAC ATCCTGTGCT CATACAGCCA               160

TGCACCATGT ATGGGGTTTG TCACATCACT CGTACGCCCC               200

CACAAGCCTG GAGATAGAAC ATACCTGACT CTAAACCCAA               240

GACCTCTAAC CACCTTATGG CGCTTTCCTG GGAGACCCAA               280

TGAGGGAATG ACATTTAAAG CCCTCCCTAG ACCAGAGTTC               320

TCAGGGTACT TTTCTATTAA AAAAAA                              346
```

(2) INFORMATION FOR SEQ ID NO: 9:

(i) SEQUENCE CHARACTERISTICS:
        (A) LENGTH: 1413 nucleotides
        (B) TYPE: nucleic acid
        (C) STRANDEDNESS: single
        (D) TOPOLOGY: linear (xi) SEQUENCE DESCRIPTION: SEQ ID NO: 9:

```
TC AAC CGG GCA GAG GGT CCA CCG GAG CCT TCA                 32
   Asn Arg Ala Glu Gly Pro Pro Glu Pro Ser
                 5                      10

CGG GTG AGC AGT GTG TCC TCC CAG TTC AGC                    62
Arg Val Ser Ser Val Ser Ser Gln Phe Ser
             15                      20

GAC GCA GCC CAG GCC AGC CCC AGC TCC CAC                    92
Asp Ala Ala Gln Ala Ser Pro Ser Ser His
             25                      30

AGC AGC ACC CCG TCC TGG TGC GAG GAG CCG                   122
Ser Ser Thr Pro Ser Trp Cys Glu Glu Pro
             35                      40

GCC CAA GCC AAC ATG GAC ATC TCC ACG GGA                   152
Ala Gln Ala Asn Met Asp Ile Ser Thr Gly
             45                      50

CAC ATG ATT CTG GCA TAC ATG GAG GAT CAC                   182
His Met Ile Leu Ala Tyr Met Glu Asp His
             55                      60

CTG CGG AAC CGG GAC CGC CTT GCC AAG GAG                   212
Leu Arg Asn Arg Asp Arg Leu Ala Lys Glu
             65                      70

TGG CAG GCC CTC TGT GCC TAC CAA GCA GAG                   242
Trp Gln Ala Leu Cys Ala Tyr Gln Ala Glu
             75                      80

CCA AAC ACC TGT GCC ACC GCG CAG GGG GAG                   272
Pro Asn Thr Cys Ala Thr Ala Gln Gly Glu
             85                      90

GGC AAC ATC AAA AAG AAC CGG CAT CCT GAC                   302
Gly Asn Ile Lys Lys Asn Arg His Pro Asp
             95                     100
```

-continued

| | |
|---|---|
| TTC CTG CCC TAT GAC CAT GCC CGC ATA AAA<br>Phe Leu Pro Tyr Asp His Ala Arg Ile Lys<br>              105                    110 | 332 |
| CTG AAG GTG GAG AGC AGC CCT TCT CGG AGC<br>Leu Lys Val Glu Ser Ser Pro Ser Arg Ser<br>              115                    120 | 362 |
| GAT TAC ATC AAC GCC AGC CCC ATT ATT GAG<br>Asp Tyr Ile Asn Ala Ser Pro Ile Ile Glu<br>              125                    130 | 392 |
| CAT GAC CCT CGG ATG CCA GCC TAC ATA GCC<br>His Asp Pro Arg Met Pro Ala Tyr Ile Ala<br>              135                    140 | 422 |
| ACG CAG GGC CCG CTG TCC CAT ACC ATC GCA<br>Thr Gln Gly Pro Leu Ser His Thr Ile Ala<br>              145                    150 | 452 |
| GAC TTC TGG CAG ATG GTG TGG GAG AGC GGC<br>Asp Phe Trp Gln Met Val Trp Glu Ser Gly<br>              155                    160 | 482 |
| TGC ACC GTC ATC GTC ATG CTG ACC CCG CTG<br>Cys Thr Val Ile Val Met Leu Thr Pro Leu<br>              165                    170 | 512 |
| GTG GAG GAT GGT GTC AAG CAG TGT GAC CGC<br>Val Glu Asp Gly Val Lys Gln Cys Asp Arg<br>              175                    180 | 542 |
| TAC TGG CCA GAT GAG GGT GCC TCC CTC TAC<br>Tyr Trp Pro Asp Glu Gly Ala Ser Leu Tyr<br>              185                    190 | 572 |
| CAC GTA TAT GAG GTG AAC CTG GTG TCG GAG<br>His Val Tyr Glu Val Asn Leu Val Ser Glu<br>              195                    200 | 602 |
| CAC ATC TGG TGC GAG GAC TTT CTG GTG CGG<br>His Ile Trp Cys Glu Asp Phe Leu Val Arg<br>              205                    210 | 632 |
| AGC TTC TAC CTG AAG AAC GTG CAG ACC CAG<br>Ser Phe Tyr Leu Lys Asn Val Gln Thr Gln<br>              215                    220 | 662 |
| GAG ACG CGC ACG CTC ACG CAG TTC CAC TTC<br>Glu Thr Arg Thr Leu Thr Gln Phe His Phe<br>              225                    230 | 692 |
| CTC AGC TGG CCG GCA GAG GGC ACA CCG GCC<br>Leu Ser Trp Pro Ala Glu Gly Thr Pro Ala<br>              235                    240 | 722 |
| TCC ACG CGG CCC CTG CTG GAC TTC CGC AGG<br>Ser Thr Arg Pro Leu Leu Asp Phe Arg Arg<br>              245                    250 | 752 |
| AAG GTG AAC AAG TGC TAC CGG GGC CGC TCC<br>Lys Val Asn Lys Cys Tyr Arg Gly Arg Ser<br>              255                    260 | 782 |
| TGC CCC ATC ATC GTG CAC TGC AGT GAT GGT<br>Cys Pro Ile Ile Val His Cys Ser Asp Gly<br>              265                    270 | 812 |
| GCG GGG AGG ACC GGC ACC TAC ATC CTC ATC<br>Ala Gly Arg Thr Gly Thr Tyr Ile Leu Ile<br>              275                    280 | 842 |
| GAC ATG GTC CTG AAC CGC ATG GCA AAA GGA<br>Asp Met Val Leu Asn Arg Met Ala Lys Gly<br>              285                    290 | 872 |
| GTG AAG GAG ATT GACATCGCT GCCACCCTGGA<br>Val Lys Glu Ile | 904 |
| GCATGTCCGT GACCAGCGGC CTGGCCTTGT CCGCTCTAAG | 944 |

```
GACCAGTTTG AATTTGCCCT GACAGCCGTG GCGGAGGAAG                    984

TGAATGCCAT CCTCAAGGCC CTGCCCCAGT GAGACCCTGG                   1024

GGCCCCTTGG CGGGCAGCCC AGCCTCTGTC CCTCTTTGCC                   1064

TGTGTGAGCA TCTCTGTGTA CCCACTCCTC ACTGCCCCAC                   1104

CAGCCACCTC TTGGGCATGC TCAGCCCTTC CTAGAAGAGT                   1144

CAGGAAGGGA AAGCCAGAAG GGGCACGCCT GCCCAGCCTC                   1184

GCATGCCAGA GCCTGGGGCA TCCCAGAGCC CAGAGCATCC                   1224

CATGGGGGTG CTGCAGCCAG GAGGAGAGGA AAGGACATGG                   1264

GTAGCAATTC TACCCAGAGC CTTCTCCTGC CTACATTCCC                   1304

TGGCCTGGCT CTCCTGTAGC TCTCCTGGGG TTCTGGGAGT                   1344

TCCCTGAACA TCTGTGTGTG TCCCCCTATG CTCCAGTATG                   1384

GAAGAATGGG GTGGAGGGTC GCCACACCC                              1413

(2) INFORMATION FOR SEQ ID NO: 10:

(i) SEQUENCE CHARACTERISTICS:
        (A) LENGTH: 3311 nucleotides
        (B) TYPE: nucleic acid
        (C) STRANDEDNESS: single
        (D) TOPOLOGY: linear (xi) SEQUENCE DESCRIPTION: SEQ ID NO: 10:

CTCCAACGCT TACAAGGTGT GCTCCGACAA CTCATGTCCC                     40

AAGGATTGTC CTGGCACGAT GACCTCACCC AGTATGTGAT                     80

CTCTCAGGAG ATGGAGCGCA TCCCCAGGCT TCGCCCCCCA                    120

GAGCCCCGTC CAAGGGACAG GTCTGGCTTG GCACCCAAGA                    160

GACCTGGTCC TGCTGGAGAG CTGCTTTTAC AGGACATCCC                    200

CACTGGCTCC GCCCCTGCTG CCCAGCATCG GCTTCCACAA                    240

CCACCAGTGG GCAAAGGTGG AGCTGGGGCC AGCTCCTCTC                    280

TGTCCCCTCT GCAGGCTGAG CTGCTCCCGC CTCTCTTGGA                    320

GCACCTGCTG CTGCCCCCAC AGCCTCCCCA CCCTTCACTG                    360

AGTTACGAAC CTGCCTTGCT GCAGCCCTAC CTGTTCCACC                    400

AGTTTGGCTC CCGTGATGGC TCCAGGGTCT CAGAGGGCTC                    440

CCCAGGGATG GTCAGTGTCG GCCCCCTGCC CAAGGCTGAA                    480

GCCCCTGCCC TCTTCAGCAG AACTGCCTCC AAGGGCATAT                    520

TTGGGGACCA CCCTGGCCAC TCCTACGGGG ACCTTCCAGG                    560

GCCTTCACCT GCCCAGCTTT TTCAAGACTC TGGGCTGCTC                    600

TATCTGGCCC AGGAGTTGCC AGCACCCAGC AGGGCCAGGG                    640

TGCCAAGGCT GCCAGAGCAA GGGAGCAGCA GCCGGGCAGA                    680

GGACTCCCCA GAGGGCTATG AGAAGGAAGG ACTAGGGGAT                    720

CGTGGAGAGA AGCCTGCTTC CCCAGCTGTG CAGCCAGATG                    760

CGGCTCTGCA GAGGCTGGCC GCTGTGCTGG CGGGCTATGG                    800

GGTAGAGCTG CGTCAGCTGA CCCCTGAGCA GCTCTCCACA                    840

CTCCTGACCC TGCTGCAGCT ACTGCCCAAG GGTGCAGGAA                    880
```

```
GAAATCCGGG AGGGGTTGTA AATGTTGGAG CTGATATCAA                                    920

GAAAACA ATG GAG GGG CCG GTG GAG GGC                                            948
        Met Glu Gly Pro Val Glu Gly
        1               5

AGA GAC ACA GCA GAG CTT CCA GCC CGC ACA                                        978
Arg Asp Thr Ala Glu Leu Pro Ala Arg Thr
    10              15

TCC CCC ATG CCT GGA CAC CCC ACT GCC AGC                                       1008
Ser Pro Met Pro Gly His Pro Thr Ala Ser
        20              25

CCT ACC TCC AGT GAA GTC CAG CAG GTG CCA                                       1038
Pro Thr Ser Ser Glu Val Gln Gln Val Pro
        30              35

AGC CCT GTC TCC TCT GAG CCT CCC AAA GCT                                       1068
Ser Pro Val Ser Ser Glu Pro Pro Lys Ala
        40              45

GCC AGA CCC CCT GTG ACA CCT GTC CTG CTA                                       1098
Ala Arg Pro Pro Val Thr Pro Val Leu Leu
        50              55

GAG AAG AAA AGC CCA CTG GGC CAG AGC CAG                                       1128
Glu Lys Lys Ser Pro Leu Gly Gln Ser Gln
        60              65

CCC ACG GTG GCA GGA CAG CCC TCA GCC CGC                                       1158
Pro Thr Val Ala Gly Gln Pro Ser Ala Arg
        70              75

CCA GCA GCA GAG GAA TAT GGC TAC ATC GTC                                       1188
Pro Ala Ala Glu Glu Tyr Gly Tyr Ile Val
        80              85

ACT GAT CAG AAG CCC CTG AGC CTG GCT GCA                                       1218
Thr Asp Gln Lys Pro Leu Ser Leu Ala Ala
        90              95

GGA GTG AAG CTG CTG GAG ATC CTG GCT GAG                                       1248
Gly Val Lys Leu Leu Glu Ile Leu Ala Glu
        100             105

CAT GTG CAC ATG TCC TCA GGC AGC TTC ATC                                       1278
His Val His Met Ser Ser Gly Ser Phe Ile
        110             115

AAC ATC AGT GTG GTG GGA CCA GCC CTC ACC                                       1308
Asn Ile Ser Val Val Gly Pro Ala Leu Thr
        120             125

TTC CGC ATC CGG CAC AAT GAG CAG AAC CTG                                       1338
Phe Arg Ile Arg His Asn Glu Gln asn Leu
        130             135

TCT TTG GCT GAT GTG ACC CAA CAA GCA GGG                                       1368
Ser Leu Ala Asp Val Thr Gln Gln Ala Gly
        140             145

CTG GTG AAG TCT GAA CTG GAA GCA CAG ACA                                       1398
Leu Val Lys Ser Glu Leu Glu Ala Gln Thr
        150             155

GGG CTC CAA ATC TTG CAG ACA GGA GTG GGA                                       1428
Gly Leu Gln Ile Leu Gln Thr Gly Val Gly
        160             165

CAG AGG GAG GAG GCA GCT GCA GTC CTT CCC                                       1458
Gln Arg Glu Glu Ala Ala Ala Val Leu Pro
        170             175

CAA ACT GCG CAC AGC ACC TCA CCC ATG CGC                                       1488
Gln Thr Ala His Ser Thr Ser Pro Met Arg
        180             185

TCA GTG CTG CTC ACT CTG GTG GCC CTG GCA                                       1518
Ser Val Leu Leu Thr Leu Val Ala Leu Ala
```

```
                190                 195
GGT GTG GCT GGG CTG CTG GTG GCT CTG GCT                          1548
Gly Val Ala Gly Leu Leu Val Ala Leu Ala
        200                 205

GTG GCT CTG TGT GTG CGG CAG CAT GCG CGG                          1578
Val Ala Leu Cys Val Arg Gln His Ala Arg
        210                 215

CAG CAA GAC AAG GAG CGC CTG GCA GCC CTG                          1608
Gln Gln Asp Lys Glu Arg Leu Ala Ala Leu
        220                 225

GGG CCT GAG GGG GCC CAT GGT GAC ACT ACC                          1638
Gly Pro Glu Gly Ala His Gly Asp Thr Thr
        230                 235

TTT GAG TAC CAG GAC CTG TGC CGC CAG CAC                          1668
Phe Glu Tyr Gln Asp Leu Cys Arg Gln His
        240                 245

ATG GCC ACG AAG TCC TTG TTC AAC CGG GCA                          1698
Met Ala Thr Lys Ser Leu Phe Asn Arg Ala
        250                 255

GAG GGT CCA CCG GAG CCT TCA CGG GTG AGC                          1728
Glu Gly Pro Pro Glu Pro Ser Arg Val Ser
        260                 265

AGT GTG TCC TCC CAG TTC AGC GAC GCA GCC                          1758
Ser Val Ser Ser Gln Phe Ser Asp Ala Ala
        270                 275

CAG GCC AGC CCC AGC TCC CAC AGC AGC ACC                          1788
Gln Ala Ser Pro Ser Ser His Ser Ser Thr
        280                 285

CCG TCC TGG TGC GAG GAG CCG GCC CAA GCC                          1818
Pro Ser Trp Cys Glu Glu Pro Ala Gln Ala
        290                 295

AAC ATG GAC ATC TCC ACG GGA CAC ATG ATT                          1848
Asn Met Asp Ile Ser Thr Gly His Met Ile
        300                 305

CTG GCA TAC ATG GAG GAT CAC CTG CGG AAC                          1878
Leu Ala Tyr Met Glu Asp His Leu Arg Asn
        310                 315

CGG GAC CGC CTT GCC AAG GAG TGG CAG GCC                          1908
Arg Asp Arg Leu Ala Lys Glu Trp Gln Ala
        320                 325

CTC TGT GCC TAC CAA GCA GAG CCA AAC ACC                          1938
Leu Cys Ala Tyr Gln Ala Glu Pro Asn Thr
        330                 335

TGT GCC ACC GCG CAG GGG GAG GGC AAC ATC                          1968
Cys Ala Thr Ala Gln Gly Glu Gly Asn Ile
        340                 345

AAA AAG AAC CGG CAT CCT GAC TTC CTG CCC                          1998
Lys Lys Asn Arg His Pro Asp Phe Leu Pro
        350                 355

TAT GAC CAT GCC CGC ATA AAA CTG AAG GTG                          2028
Tyr Asp His Ala Arg Ile Lys Leu Lys Val
        360                 365

GAG AGC AGC CCT TCT CGG AGC GAT TAC ATC                          2058
Glu Ser Ser Pro Ser Arg Ser Asp Tyr Ile
        370                 375

AAC GCC AGC CCC ATT ATT GAG CAT GAC CCT                          2088
Asn Ala Ser Pro Ile Ile Glu His Asp Pro
        380                 385

CGG ATG CCA GCC TAC ATA GCC ACG CAG GGC                          2118
Arg Met Pro Ala Tyr Ile Ala Thr Gln Gly
```

-continued

|  |  |
|---|---|
| 390 395 | |
| CCG CTG TCC CAT ACC ATC GCA GAC TTC TGG<br>Pro Leu Ser His Thr Ile Ala Asp Phe Trp<br>400 405 | 2148 |
| CAG ATG GTG TGG GAG AGC GGC TGC ACC GTC<br>Gln Met Val Trp Glu Ser Gly Cys Thr Val<br>410 415 | 2178 |
| ATC GTC ATG CTG ACC CCG CTG GTG GAG GAT<br>Ile Val Met Leu Thr Pro Leu Val Glu Asp<br>420 425 | 2208 |
| GGT GTC AAG CAG TGT GAC CGC TAC TGG CCA<br>Gly Val Lys Gln Cys Asp Arg Tyr Trp Pro<br>430 435 | 2238 |
| GAT GAG GGT GCC TCC CTC TAC CAC GTA TAT<br>Asp Glu Gly Ala Ser Leu Tyr His Val Tyr<br>440 445 | 2268 |
| GAG GTG AAC CTG GTG TCG GAG CAC ATC TGG<br>Glu Val Asn Leu Val Ser Glu His Ile Trp<br>450 455 | 2298 |
| TGC GAG GAC TTT CTG GTG CGG AGC TTC TAC<br>Cys Glu Asp Phe Leu Val Arg Ser Phe Tyr<br>460 465 | 2328 |
| CTG AAG AAC GTG CAG ACC CAG GAG ACG CGC<br>Leu Lys Asn Val Gln Thr Gln Glu Thr Arg<br>470 475 | 2358 |
| ACG CTC ACG CAG TTC CAC TTC CTC AGC TGG<br>Thr Leu Thr Gln Phe His Phe Leu Ser Trp<br>480 485 | 2388 |
| CCG GCA GAG GGC ACA CCG GCC TCC ACG CGG<br>Pro Ala Glu Gly Thr Pro Ala Ser Thr Arg<br>490 495 | 2418 |
| CCC CTG CTG GAC TTC CGC AGG AAG GTG AAC<br>Pro Leu Leu Asp Phe Arg Arg Lys Val Asn<br>500 505 | 2448 |
| AAG TGC TAC CGG GGC CGC TCC TGC CCC ATC<br>Lys Cys Tyr Arg Gly Arg Ser Cys Pro Ile<br>510 515 | 2478 |
| ATC GTG CAC TGC AGT GAT GGT GCG GGG AGG<br>Ile Val His Cys Ser Asp Gly Ala Gly Arg<br>520 525 | 2508 |
| ACC GGC ACC TAC ATC CTC ATC GAC ATG GTC<br>Thr Gly Thr Tyr Ile Leu Ile Asp Met Val<br>530 535 | 2538 |
| CTG AAC CGC ATG GCA AAA GGA GTG AAG GAG<br>Leu Asn Arg Met Ala Lys Gly Val Lys Glu<br>540 545 | 2568 |
| ATT GACATCGCTG CCACCCTGGA GCATGTCCGT<br>Ile | 2601 |
| GACCAGCGGC CTGGCCTTGT CCGCTCTAAG GACCAGTTTG | 2641 |
| AATTTGCCCT GACAGCCGTG GCGGAGGAAG TGAATGCCAT | 2681 |
| CCTCAAGGCC CTGCCCCAGT GAGACCCTGG GGCCCCTTGG | 2721 |
| CGGGCAGCCC AGCCTCTGTC CCTCTTTGCC TGTGTGAGCA | 2761 |
| TCTCTGTGTA CCCACTCCTC ACTGCCCCAC CAGCCACCTC | 2801 |
| TTGGGCATGC TCAGCCCTTC CTAGAAGAGT CAGGAAGGGA | 2841 |
| AAGCCAGAAG GGGCACGCCT GCCCAGCCTC GCATGCCAGA | 2881 |
| GCCTGGGGCA TCCCAGAGCC CAGAGCATCC CATGGGGGTG | 2921 |

| | |
|---|---|
| CTGCAGCCAG GAGGAGAGGA AAGGACATGG GTAGCAATTC | 2961 |
| TACCCAGAGC CTTCTCCTGC CTACATTCCC TGGCCTGGCT | 3001 |
| CTCCTGTAGC TCTCCTGGGG TTCTGGGAGT TCCCTGAACA | 3041 |
| TCTGTGTGTG TCCCCCTATG CTCCAGTATG GAAGAATGGG | 3081 |
| GTGGAGGGTC GCCACACCCG GCTCCCCCTG CTTCTCAGCC | 3121 |
| CCGGGCCTGC CTCTGACTCA CACTTGGGCG CTCTGCCCTC | 3161 |
| CCTGGCCTCA CGCCCAGCCT CCTCCCACCA CCCTCCCACC | 3201 |
| ATGCGCTGCT CAACCTCTCT CCTTCTGGCG CAAGAGAACA | 3241 |
| TTTCTAGAAA AAACTACTTT TGTACCAGTG TGAATAAAGT | 3281 |
| TAGTGTGTTG TCTGTGCAGC TGCAAAAAAA | 3311 |

(2) INFORMATION FOR SEQ ID NO: 11:

(i) SEQUENCE CHARACTERISTICS:
        (A) LENGTH: 195 amino acids
        (B) TYPE: amino acid
        (D) TOPOLOGY: linear (xi) SEQUENCE DESCRIPTION: SEQ ID NO: 11:

```
Pro Met Asn Ala Phe Met Val Trp Ala Lys
 1               5                  10

Asp Glu Arg Arg Lys Ile Leu Gln Ala Phe
                15                  20

Pro Asp Met His Asn Ser Ser Ile Ser Lys
                25                  30

Ile Leu Gly Ser Arg Trp Lys Ser Met Thr
                35                  40

Asn Gln Glu Xaa Gln Pro Tyr Tyr Glu Glu
                45                  50

Gln Ala Leu Leu Ile Val Ile Thr Trp Arg
                55                  60

Ser Ile Leu Thr Thr Ser Thr Ser Arg Gly
                65                  70

Gln Ala His Leu His Arg Gly Gly Gln Ala
                75                  80

Ala Ala Arg Gly Arg Val Gln Gly Pro Asp
                85                  90

Glu Asp Pro Ala Ser Gly Cys Pro Pro Glu
                95                  100

Leu Arg Asp Pro Pro Ala Gly Trp Pro Gly
                105                 110

Ala Asp Glu Leu Leu Arg Cys Pro Val Pro
                115                 120

Ser Gly Ser Arg His Ala Ala Ala Gln Pro
                125                 130

Leu Val Glu His Tyr Val Pro Arg Ser Leu
                135                 140

Asp Pro Asn Met Pro Val Ile Val Asn Thr
                145                 150

Cys Ser Leu Arg Glu Glu Gly Glu Gly Thr
                155                 160

Asp Asp Arg His Ser Val Ala Asp Gly Glu
```

```
                165                 170

Met Tyr Arg Tyr Ser Glu Asp Glu Asp Ser
                175                 180

Glu Gly Glu Glu Lys Ser Asp Gly Glu Leu
                185                 190

Val Val Leu Thr Asp
                195

(2) INFORMATION FOR SEQ ID NO: 12:

(i) SEQUENCE CHARACTERISTICS:
        (A) LENGTH: 604 amino acids
        (B) TYPE: amino acid
        (D) TOPOLOGY:  linear (xi) SEQUENCE DESCRIPTION:  SEQ ID NO: 12:

Met Ser Ser Lys Gln
 1               5

Ala Thr Ser Pro Phe Ala Cys Ala Ala Asp
                 10                  15

Gly gln Asp Ala Met Thr Gln Asp Leu Thr
                 20                  25

Ser Arg Glu Lys Glu Glu Gly Ser Asp Gln
                 30                  35

His Val Ala Ser His Leu Pro Leu His Pro
                 40                  45

Ile Met His Asn Leu Pro His Ser Glu Glu
                 50                  55

Leu Pro Thr Leu Val Ser Thr Ile Gln Gln
                 60                  65

Asp Ala Asp Trp Asp Ser Val Leu Ser Ser
                 70                  75

Gln Gln Arg Met Glu Ser Gln Asn Asn Lys
                 80                  85

Leu Cys Ser Leu Tyr Ser Phe Arg Asn Thr
                 90                  95

Ser Thr Ser Pro His Lys Pro Asp Glu Gly
                 100                 105

Ser Arg Asp Arg Glu Ile Met Thr Ser Val
                 110                 115

Thr Phe Gly Thr Pro Glu Arg Arg Lys Gly
                 120                 125

Ser Leu Ala Asp Val Val Asp Thr Leu Lys
                 130                 135

Gln Lys Lys Leu Glu Glu Met Thr Arg Thr
                 140                 145

Glu Gln Glu Asp Ser Ser Cys Met Glu Lys
                 150                 155

Leu Leu Ser Lys Asp Trp Lys Glu Lys Met
                 160                 165

Glu Arg Leu Asn Thr Ser Glu Leu Leu Gly
                 170                 175

Glu Ile Lys Gly Thr Pro Glu Ser Leu Ala
                 180                 185

Glu Lys Glu Arg Gln Leu Ser Thr Met Ile
                 190                 195
```

```
Thr Gln Leu Ile Ser Leu Arg Glu Gln Leu
            200                 205

Leu Ala Ala His Asp Glu Gln Lys Lys Leu
            210                 215

Ala Ala Ser Gln Ile Glu Lys Gln Arg Gln
            220                 225

Gln Met Asp Leu Ala Arg Gln Gln Gln Glu
            230                 235

Gln Ile Ala Arg Gln Gln Gln Gln Leu Leu
            240                 245

Gln Gln Gln His Lys Ile Asn Leu Leu Gln
            250                 255

Gln Gln Ile Gln Val Gln Gly His Met Pro
            260                 265

Pro Leu Met Ile Pro Ile Phe Pro His Asp
            270                 275

Gln Arg Thr Leu Ala Ala Ala Ala Ala Ala
            280                 285

Gln Gln Gly Phe Leu Phe Pro Pro Gly Ile
            290                 295

Thr Tyr Lys Pro Gly Asp Asn Tyr Pro Val
            300                 305

Gln Phe Ile Pro Ser Thr Met Ala Ala Ala
            310                 315

Ala Ala Ser Gly Leu Ser Pro Leu Gln Leu
            320                 325

Gln Lys Gly His Val Ser His Pro Gln Ile
            330                 335

Asn Gln Arg Leu Lys Gly Leu Ser Asp Arg
            340                 345

Phe Gly Arg Asn Leu Asp Thr Phe Glu His
            350                 355

Gly Gly Gly His Ser Tyr Asn His Lys Gln
            360                 365

Ile Glu Gln Leu Tyr Ala Ala Gln Leu Ala
            370                 375

Ser Met Gln Val Ser Pro Gly Ala Lys Met
            380                 385

Pro Ser Thr Pro Gln Pro Pro Asn Thr Ala
            390                 395

Gly Thr Val Ser Pro Thr Gly Ile Lys Asn
            400                 405

Glu Lys Arg Gly Thr Ser Pro Val Thr Gln
            410                 415

Val Lys Asp Glu Ala Ala Ala Gln Pro Leu
            420                 425

Asn Leu Ser Ser Arg Pro Lys Thr Ala Glu
            430                 435

Pro Val Lys Ser Pro Thr Ser Pro Thr Gln
            440                 445

Asn Leu Phe Pro Ala Ser Lys Thr Ser Pro
            450                 455

Val Asn Leu Pro Asn Lys Ser Ser Ile Pro
```

```
                        460                 465
Ser Pro Ile Gly Gly Ser Leu Gly Arg Gly
                        470                 475
Ser Ser Leu Asp Ile Leu Ser Ser Leu Asn
                        480                 485
Ser Pro Ala Leu Phe Gly Asp Gln Asp Thr
                        490                 495
Val Met Lys Ala Ile Gln Glu Ala Arg Lys
                        500                 505
Met Arg Glu Gln Ile Gln Arg Glu Gln Gln
                        510                 515
Gln Gln Gln Pro His Gly Val Asp Gly Lys
                        520                 525
Lys Ser Ser Ile Asn Asn Met Gly Leu Asn
                        530                 535
Ser Cys Arg Asn Glu Lys Glu Arg Thr Arg
                        540                 545
Phe Glu Asn Leu Xaa Pro Gln Leu Thr Gly
                        550                 555
Lys Ser Asn Glu Asp Gly Lys Leu Gly Pro
                        560                 565
Gly Val Ile Asp Leu Thr Arg Pro Glu Asp
                        570                 575
Ala Glu Gly Gly Ala Thr Val Ala Glu Ala
                        580                 585
Arg Val Tyr Arg Asp Ala Arg Gly Leu Pro
                        590                 595
Ala Ala Ser His Thr Leu Ser Asp Gln
                        600

(2) INFORMATION FOR SEQ ID NO: 13:

(i) SEQUENCE CHARACTERISTICS:
          (A) LENGTH: 191 amino acids
          (B) TYPE: amino acid
          (D) TOPOLOGY:  linear (xi) SEQUENCE DESCRIPTION: SEQ ID NO: 13:

Ile Glu Lys Leu Lys Leu Glu Ile Glu Lys
 1               5                  10

Leu Lys Ala Glu Ser Gly Asn Pro Ser Ile
                15                  20

Arg Gln Lys Ile Arg Leu Lys Asp Lys Ala
                25                  30

Ala Asp Ala Lys Lys Ile Gln Asp Leu Glu
                35                  40

Arg Gln Val Lys Glu Met Glu Gly Ile Leu
                45                  50

Lys Arg Arg Tyr Pro Asn Ser Leu Pro Ala
                55                  60

Leu Ile Leu Ala Ala Ser Ala Ala Gly Asp
                65                  70

Thr Val Asp Lys Asn Thr Val Glu Phe Met
                75                  80

Glu Lys Arg Ile Lys Lys Leu Glu Ala Asp
                85                  90
```

```
Leu Glu Gly Lys Asp Glu Asp Ala Lys Lys
             95                  100

Ser Leu Arg Thr Met Glu Gln Gln Phe Gln
            105                  110

Lys Met Lys Ile Gln Tyr Glu Gln Arg Leu
            115                  120

Glu Gln Gln Glu Gln Leu Leu Ala Cys Lys
            125                  130

Leu Asn Gln His Asp Ser Pro Arg Ile Lys
            135                  140

Ala Leu Glu Lys Glu Leu Asp Asp Ile Lys
            145                  150

Glu Ala His Gln Ile Thr Val Arg Asn Leu
            155                  160

Glu Ala Glu Ile Asp Val Leu Lys His Gln
            165                  170

Asn Ala Glu Leu Asp Val Lys Lys Asn Asp
            175                  180

Lys Asp Asp Glu Asp Phe Gln Ser Ile Glu
            185                  190

Phe
```

(2) INFORMATION FOR SEQ ID NO: 14:

(i) SEQUENCE CHARACTERISTICS:
        (A) LENGTH: 264 amino acids
        (B) TYPE: amino acid
        (D) TOPOLOGY: linear (xi) SEQUENCE DESCRIPTION: SEQ ID NO: 14:

```
Asp Thr Pro Cys Val Lys Val Gly Asp Glu
 1               5                   10

Val Glu Val Met Val Val Glu Lys Glu Asp
            15                   20

Arg Asn Gly Asn Leu Asn Leu Ser Arg Lys
            25                   30

Ser Ala Arg Ile Phe Arg Ala Trp Glu Arg
            35                   40

Ile Met Glu Val His Lys Thr Gly Glu Val
            45                   50

Val Thr Gly Leu Val Thr Ser Lys Thr Lys
            55                   60

Gly Gly Leu Ile Val Asp Val Phe Gly Met
            65                   70

Glu Thr Phe Leu Pro Gly Ser Gln Ile Asp
            75                   80

Val Lys Pro Val Thr Asp Tyr Asp Gln Phe
            85                   90

Val Gly Lys Thr Met Glu Phe Lys Val Val
            95                  100

Lys Ile Asn Glu Thr Ile Lys Asn Ala Val
            105                 110

Val Ser His Lys Ala Leu Ile Glu Ser Asp
            115                 120

Ile Glu Ala Gln Arg Ala Glu Ile Met Ser
```

```
                   125                 130

Lys Leu Glu Lys Gly Gln Val Leu Glu Gly
                135                 140

Thr Val Lys Asn Ile Thr Asp Phe Gly Ala
                145                 150

Phe Met Asp Leu Gly Gly Leu Asp Gly Leu
                155                 160

Leu Tyr Ile Thr Asp Ile Ser Trp Gly Arg
                165                 170

Ile Ser His Pro Ser Glu Val Leu Lys Met
                175                 180

Asp Gln Lys Leu Asn Val Val Leu Asp
                185                 190

Phe Asp Asp Lys Lys Arg Ile Ser Leu
                195                 200

Gly Leu Lys Gln Leu Thr Pro His Pro Trp
                205                 210

Glu Val Leu Pro Glu Gly Leu Ala Glu Gly
                215                 220

Ala Ile Val Lys Gly Lys Val Val Asn Ile
                225                 230

Glu Asp Tyr Gly Ala Phe Leu Glu Ile Gln
                235                 240

Pro Gly Val Glu Gly Leu Val His Val Ser
                245                 250

Glu Ile Thr Trp Glu Asn Thr Pro Ile Asn
                255                 260

Ala Lys Glu Phe (2) INFORMATION FOR SEQ ID NO: 15:

(i) SEQUENCE CHARACTERISTICS:
        (A) LENGTH: 253 amino acids
        (B) TYPE: amino acid
        (D) TOPOLOGY:  linear (xi) SEQUENCE DESCRIPTION:  SEQ ID NO: 15:

Asp Gly Ser Pro Asn Thr Pro Phe Arg Lys
 1               5                  10

Asp Leu Ile Ser Leu Asp Ser Ser Pro Ala
                15                  20

Lys Glu Arg Leu Glu Asp Gly Cys Val His
                25                  30

Pro Leu Glu Glu Ala Met Leu Ser Cys Asp
                35                  40

Met Asp Gly Ser Arg His Phe Pro Glu Ser
                45                  50

Arg Asn Ser Ser His Ile Lys Arg Pro Met
                55                  60

Asn Ala Phe Met Val Trp Ala Lys Asp Glu
                65                  70

Arg Arg Lys Ile Leu Gln Ala Phe Pro Asp
                75                  80

Met His Asn Ser Ser Ile Ser Lys Ile Leu
                85                  90
```

```
Gly Ser Arg Trp Lys Ser Met Thr Asn Gln
                 95              100

Glu Lys Gln Pro Tyr Tyr Glu Glu Gln Ala
                105              110

Leu Leu Ile Val Ile Thr Trp Arg Ser Ile
                115              120

Leu Thr Thr Ser Thr Ser Arg Gly Gln Ala
                125              130

His Leu His Arg Gly Gly Gln Ala Ala Ala
                135              140

Arg Gly Arg Val Gln Gly Pro Asp Glu Asp
                145              150

Pro Ala Ser Gly Cys Pro Pro Glu Leu Arg
                155              160

Asp Pro Pro Ala Gly Trp Pro Gly Ala Asp
                165              170

Glu Leu Leu Arg Cys Pro Val Pro Ser Gly
                175              180

Ser Arg His Ala Ala Ala Gln Pro Leu Val
                185              190

Glu His Tyr Val Pro Arg Ser Leu Asp Pro
                195              200

Asn Met Pro Val Ile Val Asn Thr Cys Ser
                205              210

Leu Arg Glu Glu Gly Glu Gly Thr Asp Asp
                215              220

Arg His Ser Val Ala Asp Gly Glu Met Tyr
                225              230

Arg Tyr Ser Glu Asp Glu Asp Ser Glu Gly
                235              240

Glu Glu Lys Ser Asp Gly Glu Leu Val Val
                245              250

Leu Thr Asp
```

(2) INFORMATION FOR SEQ ID NO: 16:

(i) SEQUENCE CHARACTERISTICS:
        (A) LENGTH: 308 amino acids
        (B) TYPE: amino acid
        (D) TOPOLOGY: linear (xi) SEQUENCE DESCRIPTION: SEQ ID NO: 16:

```
Met Ser Ser Cys Val Pro Arg Pro
 1               5

Pro Ser His Gly Gly Pro Thr Arg Asp Leu
                 10              15

Gln Ser Ser Pro Pro Ser Leu Pro Leu Gly
                 20              25

Phe Leu Gly Glu Gly Asp Ala Val Thr Lys
                 30              35

Ala Ile Gln Asp Ala Arg Gln Leu Leu His
                 40              45

Ser His Ser Gly Ala Leu Asp Gly Ser Pro
                 50              55

Asn Thr Pro Phe Arg Lys Asp Leu Ile Ser
                 60              65
```

Leu Asp Ser Ser Pro Ala Lys Glu Arg Leu
        70                  75

Glu Asp Gly Cys Val His Pro Leu Glu Glu
        80                  85

Ala Met Leu Ser Cys Asp Met Asp Gly Ser
        90                  95

Arg His Phe Pro Glu Ser Arg Asn Ser Ser
       100                 105

His Ile Lys Arg Pro Met Asn Ala Phe Met
       110                 115

Val Trp Ala Lys Asp Glu Arg Arg Lys Ile
       120                 125

Leu Gln Ala Phe Pro Asp Met His Asn Ser
       130                 135

Ser Ile Ser Lys Ile Leu Gly Ser Arg Trp
       140                 145

Lys Ser Met Thr Asn Gln Glu Lys Gln Pro
       150                 155

Tyr Tyr Glu Glu Gln Ala Arg Leu Ser Lys
       160                 165

Gln His Leu Glu Lys Tyr Pro Asp Tyr Lys
       170                 175

Tyr Lys Pro Arg Pro Lys Arg Thr Cys Ile
       180                 185

Val Glu Gly Lys Arg Leu Arg Val Gly Glu
       190                 195

Tyr Lys Ala Leu Met Arg Thr Arg Arg Gln
       200                 205

Asp Ala Arg Gln Ser Tyr Val Ile Pro Pro
       210                 215

Gln Ala Gly Gln Val Gln Met Ser Ser Ser
       220                 225

Asp Val Leu Tyr Pro Arg Ala Ala Gly Met
       230                 235

Pro Leu Ala Gln Pro Leu Val Glu His Tyr
       240                 245

Val Pro Arg Ser Leu Asp Pro Asn Met Pro
       250                 255

Val Ile Val Asn Thr Cys Ser Leu Arg Glu
       260                 265

Glu Gly Glu Gly Thr Asp Asp Arg His Ser
       270                 275

Val Ala Asp Gly Glu Met Tyr Arg Tyr Ser
       280                 285

Glu Asp Glu Asp Ser Glu Gly Glu Glu Lys
       290                 295

Ser Asp Gly Glu Leu Val Val Leu Thr Asp
       300                 305

(2) INFORMATION FOR SEQ ID NO: 17:

(i) SEQUENCE CHARACTERISTICS:
        (A) LENGTH: 712 amino acids
        (B) TYPE: amino acid
        (D) TOPOLOGY: linear (xi) SEQUENCE DESCRIPTION: SEQ ID NO: 17:

```
Met Met Ala Gln Ser
  1               5

Asn Met Phe Thr Val Ala Asp Val Leu Ser
                 10                  15

Gln Asp Glu Leu Arg Lys Lys Leu Tyr Gln
                 20                  25

Thr Phe Lys Asp Arg Gly Ile Leu Asp Thr
                 30                  35

Leu Lys Thr Gln Leu Arg Asn Gln Leu Ile
                 40                  45

His Glu Leu Met His Pro Val Leu Ser Gly
                 50                  55

Glu Leu Gln Pro Arg Ser Ile Ser Val Glu
                 60                  65

Gly Ser Ser Leu Leu Ile Gly Ala Ser Asn
                 70                  75

Ser Leu Val Ala Asp His Leu Gln Arg Cys
                 80                  85

Gly Tyr Glu Tyr Ser Leu Ser Val Phe Phe
                 90                  95

Pro Glu Ser Gly Leu Ala Lys Glu Lys Val
                100                 105

Phe Thr Met Gln Asp Leu Leu Gln Leu Ile
                110                 115

Lys Ile Asn Pro Thr Ser Ser Leu Tyr Lys
                120                 125

Ser Leu Val Ser Gly Ser Asp Lys Glu Asn
                130                 135

Gln Lys Gly Phe Leu Met His Phe Leu Lys
                140                 145

Glu Leu Ala Glu Tyr His Gln Ala Lys Glu
                150                 155

Ser Cys Asn Met Glu Thr Gln Thr Ser Ser
                160                 165

Thr Phe Asn Arg Asp Ser Leu Ala Glu Lys
                170                 175

Leu Gln Leu Ile Asp Asp Gln Phe Ala Asp
                180                 185

Ala Tyr Pro Gln Arg Ile Lys Phe Glu Ser
                190                 195

Leu Glu Ile Lys Leu Asn Val Tyr Lys Arg
                200                 205

Glu Ile Glu Glu Gln Leu Arg Ala Glu Met
                210                 215

Cys Gln Lys Leu Lys Phe Phe Lys Asp Thr
                220                 225

Glu Ile Ala Lys Ile Lys Met Glu Ala Lys
                230                 235

Lys Lys Tyr Glu Lys Glu Leu Thr Met Phe
                240                 245

Gln Asn Asp Phe Glu Lys Ala Cys Gln Ala
                250                 255
```

```
Lys Ser Glu Ala Leu Val Leu Arg Glu Lys
            260                 265

Ser Thr Leu Glu Arg Ile His Lys His Gln
            270                 275

Glu Ile Glu Thr Lys Glu Ile Tyr Ala Gln
            280                 285

Arg Gln Leu Leu Leu Lys Asp Met Asp Leu
            290                 295

Leu Arg Gly Arg Glu Ala Glu Leu Lys Gln
            300                 305

Arg Val Glu Ala Phe Glu Leu Asn Gln Lys
            310                 315

Leu Gln Glu Glu Lys Met Lys Ser Ile Thr
            320                 325

Glu Ala Leu Arg Arg Gln Glu Gln Asn Ile
            330                 335

Lys Ser Phe Glu Glu Thr Tyr Asp Arg Lys
            340                 345

Leu Lys Asn Glu Leu Leu Lys Tyr Gln Leu
            350                 355

Glu Leu Lys Asp Asp Tyr Ile Ile Arg Thr
            360                 365

Asn Arg Leu Ile Glu Asp Glu Arg Lys Asn
            370                 375

Lys Glu Lys Ala Val His Leu Gln Glu Glu
            380                 385

Leu Ile Ala Ile Asn Ser Lys Lys Glu Glu
            390                 395

Leu Asn Gln Ser Val Asn Arg Val Lys Glu
            400                 405

Leu Glu Leu Glu Leu Glu Ser Val Lys Ala
            410                 415

Gln Ser Leu Ala Ile Thr Lys Gln Asn His
            420                 425

Met Leu Asn Glu Lys Val Lys Glu Met Ser
            430                 435

Asp Tyr Ser Leu Leu Lys Glu Glu Lys Leu
            440                 445

Glu Leu Leu Ala Gln Asn Lys Leu Leu Lys
            450                 455

Gln Gln Leu Glu Glu Ser Arg Asn Glu Asn
            460                 465

Leu Arg Leu Leu Asn Arg Leu Ala Gln Pro
            470                 475

Ala Pro Glu Leu Ala Val Phe Gln Lys Glu
            480                 485

Leu Arg Lys Ala Glu Lys Ala Ile Val Val
            490                 495

Glu His Glu Glu Phe Glu Ser Cys Arg Gln
            500                 505

Ala Leu His Lys Gln Leu Gln Asp Glu Ile
            510                 515

Glu His Ser Ala Gln Leu Lys Ala Gln Ile
```

```
                        520                 525
Leu Gly Tyr Lys Ala Ser Val Lys Ser Leu
                530                 535
Thr Thr Gln Val Ala Asp Leu Lys Leu Gln
                540                 545
Leu Lys Gln Thr Gln Thr Ala Leu Glu Asn
                550                 555
Glu Val Tyr Cys Asn Pro Lys Gln Ser Val
                560                 565
Ile Asp Arg Ser Val Asn Gly Leu Ile Asn
                570                 575
Gly Asn Val Val Pro Cys Asn Gly Glu Ile
                580                 585
Ser Gly Asp Phe Leu Asn Asn Pro Phe Lys
                590                 595
Gln Glu Asn Val Leu Ala Arg Met Val Ala
                600                 605
Ser Arg Ile Thr Asn Tyr Pro Thr Ala Trp
                610                 615
Val Glu Gly Ser Ser Pro Asp Ser Asp Leu
                620                 625
Asn Thr Lys Ala Arg Val Lys Glu Leu Gln
                630                 635
Gln Glu Ala Glu Arg Leu Glu Lys Ala Phe
                640                 645
Arg Ser Tyr His Arg Arg Val Ile Lys Asn
                650                 655
Ser Ala Lys Ser Pro Lys Ala Ala Lys Ser
                660                 665
Pro Pro Leu Cys Thr Cys Trp Lys Pro Ser
                670                 675
Lys Thr Leu Leu Pro Val Pro Arg Lys Asp
                680                 685
Ile Phe Leu Glu Arg Thr Glu Leu Ser Leu
                690                 695
Ser Ser Leu Lys Trp Ala His Leu Lys Lys
                700                 705
Gly Met Thr Ser Trp Lys His
                710

(2) INFORMATION FOR SEQ ID NO: 18:

(i) SEQUENCE CHARACTERISTICS:
        (A) LENGTH: 294 amino acids
        (B) TYPE: amino acid
        (D) TOPOLOGY: linear (xi) SEQUENCE DESCRIPTION: SEQ ID NO: 18:

Asn Arg Ala Glu Gly Pro Pro Glu Pro Ser
 1               5                  10
Arg Val Ser Ser Val Ser Ser Gln Phe Ser
                15                  20
Asp Ala Ala Gln Ala Ser Pro Ser Ser His
                25                  30
Ser Ser Thr Pro Ser Trp Cys Glu Glu Pro
                35                  40
```

Ala Gln Ala Asn Met Asp Ile Ser Thr Gly
                45                  50

His Met Ile Leu Ala Tyr Met Glu Asp His
                55                  60

Leu Arg Asn Arg Asp Arg Leu Ala Lys Glu
                65                  70

Trp Gln Ala Leu Cys Ala Tyr Gln Ala Glu
                75                  80

Pro Asn Thr Cys Ala Thr Ala Gln Gly Glu
                85                  90

Gly Asn Ile Lys Lys Asn Arg His Pro Asp
                95                  100

Phe Leu Pro Tyr Asp His Ala Arg Ile Lys
                105                 110

Leu Lys Val Glu Ser Ser Pro Ser Arg Ser
                115                 120

Asp Tyr Ile Asn Ala Ser Pro Ile Ile Glu
                125                 130

His Asp Pro Arg Met Pro Ala Tyr Ile Ala
                135                 140

Thr Gln Gly Pro Leu Ser His Thr Ile Ala
                145                 150

Asp Phe Trp Gln Met Val Trp Glu Ser Gly
                155                 160

Cys Thr Val Ile Val Met Leu Thr Pro Leu
                165                 170

Val Glu Asp Gly Val Lys Gln Cys Asp Arg
                175                 180

Tyr Trp Pro Asp Glu Gly Ala Ser Leu Tyr
                185                 190

His Val Tyr Glu Val Asn Leu Val Ser Glu
                195                 200

His Ile Trp Cys Glu Asp Phe Leu Val Arg
                205                 210

Ser Phe Tyr Leu Lys Asn Val Gln Thr Gln
                215                 220

Glu Thr Arg Thr Leu Thr Gln Phe His Phe
                225                 230

Leu Ser Trp Pro Ala Glu Gly Thr Pro Ala
                235                 240

Ser Thr Arg Pro Leu Leu Asp Phe Arg Arg
                245                 250

Lys Val Asn Lys Cys Tyr Arg Gly Arg Ser
                255                 260

Cys Pro Ile Ile Val His Cys Ser Asp Gly
                265                 270

Ala Gly Arg Thr Gly Thr Tyr Ile Leu Ile
                275                 280

Asp Met Val Leu Asn Arg Met Ala Lys Gly
                285                 290

Val Lys Glu Ile (2) INFORMATION FOR SEQ ID NO: 19:

(i) SEQUENCE CHARACTERISTICS:
    (A) LENGTH: 548 amino acids
    (B) TYPE: amino acid
    (D) TOPOLOGY: linear (xi) SEQUENCE DESCRIPTION: SEQ ID NO: 19:

```
Met Glu Gly Pro Val Glu Gly
 1               5

Arg Asp Thr Ala Glu Leu Pro Ala Arg Thr
        10                  15

Ser Pro Met Pro Gly His Pro Thr Ala Ser
        20                  25

Pro Thr Ser Ser Glu Val Gln Gln Val Pro
        30                  35

Ser Pro Val Ser Ser Glu Pro Pro Lys Ala
        40                  45

Ala Arg Pro Pro Val Thr Pro Val Leu Leu
        50                  55

Glu Lys Lys Ser Pro Leu Gly Gln Ser Gln
        60                  65

Pro Thr Val Ala Gly Gln Pro Ser Ala Arg
        70                  75

Pro Ala Ala Glu Glu Tyr Gly Tyr Ile Val
        80                  85

Thr Asp Gln Lys Pro Leu Ser Leu Ala Ala
        90                  95

Gly Val Lys Leu Leu Glu Ile Leu Ala Glu
       100                 105

His Val His Met Ser Ser Gly Ser Phe Ile
       110                 115

Asn Ile Ser Val Val Gly Pro Ala Leu Thr
       120                 125

Phe Arg Ile Arg His Asn Glu Gln asn Leu
       130                 135

Ser Leu Ala Asp Val Thr Gln Gln Ala Gly
       140                 145

Leu Val Lys Ser Glu Leu Glu Ala Gln Thr
       150                 155

Gly Leu Gln Ile Leu Gln Thr Gly Val Gly
       160                 165

Gln Arg Glu Glu Ala Ala Ala Val Leu Pro
       170                 175

Gln Thr Ala His Ser Thr Ser Pro Met Arg
       180                 185

Ser Val Leu Leu Thr Leu Val Ala Leu Ala
       190                 195

Gly Val Ala Gly Leu Leu Val Ala Leu Ala
       200                 205

Val Ala Leu Cys Val Arg Gln His Ala Arg
       210                 215

Gln Gln Asp Lys Glu Arg Leu Ala Ala Leu
       220                 225

Gly Pro Glu Gly Ala His Gly Asp Thr Thr
       230                 235
```

-continued

```
Phe Glu Tyr Gln Asp Leu Cys Arg Gln His
        240                 245

Met Ala Thr Lys Ser Leu Phe Asn Arg Ala
        250                 255

Glu Gly Pro Pro Glu Pro Ser Arg Val Ser
        260                 265

Ser Val Ser Ser Gln Phe Ser Asp Ala Ala
        270                 275

Gln Ala Ser Pro Ser Ser His Ser Ser Thr
        280                 285

Pro Ser Trp Cys Glu Glu Pro Ala Gln Ala
        290                 295

Asn Met Asp Ile Ser Thr Gly His Met Ile
        300                 305

Leu Ala Tyr Met Glu Asp His Leu Arg Asn
        310                 315

Arg Asp Arg Leu Ala Lys Glu Trp Gln Ala
        320                 325

Leu Cys Ala Tyr Gln Ala Glu Pro Asn Thr
        330                 335

Cys Ala Thr Ala Gln Gly Glu Gly Asn Ile
        340                 345

Lys Lys Asn Arg His Pro Asp Phe Leu Pro
        350                 355

Tyr Asp His Ala Arg Ile Lys Leu Lys Val
        360                 365

Glu Ser Ser Pro Ser Arg Ser Asp Tyr Ile
        370                 375

Asn Ala Ser Pro Ile Ile Glu His Asp Pro
        380                 385

Arg Met Pro Ala Tyr Ile Ala Thr Gln Gly
        390                 395

Pro Leu Ser His Thr Ile Ala Asp Phe Trp
        400                 405

Gln Met Val Trp Glu Ser Gly Cys Thr Val
        410                 415

Ile Val Met Leu Thr Pro Leu Val Glu Asp
        420                 425

Gly Val Lys Gln Cys Asp Arg Tyr Trp Pro
        430                 435

Asp Glu Gly Ala Ser Leu Tyr His Val Tyr
        440                 445

Glu Val Asn Leu Val Ser Glu His Ile Trp
        450                 455

Cys Glu Asp Phe Leu Val Arg Ser Phe Tyr
        460                 465

Leu Lys Asn Val Gln Thr Gln Glu Thr Arg
        470                 475

Thr Leu Thr Gln Phe His Phe Leu Ser Trp
        480                 485

Pro Ala Glu Gly Thr Pro Ala Ser Thr Arg
        490                 495

Pro Leu Leu Asp Phe Arg Arg Lys Val Asn
        500                 505
```

```
Lys Cys Tyr Arg Gly Arg Ser Cys Pro Ile
        510                 515

Ile Val His Cys Ser Asp Gly Ala Gly Arg
        520                 525

Thr Gly Thr Tyr Ile Leu Ile Asp Met Val
        530                 535

Leu Asn Arg Met Ala Lys Gly Val Lys Glu
        540                 545

Ile
```

PANCREATIC ISLET CELL ANTIGENS OBTAINED BY MOLECULAR CLONING

CROSS-REFERENCE TO RELATED APPLICATION

This application is a divisional of application Ser. No. 08/239,276, filed May 5, 1994, now U.S. Pat. No. 584,836 which is, in turn, a continuation of Ser. No. 07/872, filed Jun. 8, 1992, now abandoned, which is, in turn, a continuation of Ser. No. 07/715,181, filed Jun. 14, 1991, now abandoned, which is, in turn, a continuation-in-part of Ser. No. 07/441, 703, filed Dec. 4, 1989, now abandoned, which is, in turn, a continuation-in-part of Ser. No. 07/312,543, filed Feb. 17, 1989, now abandoned.

BACKGROUND OF THE INVENTION

This invention relates to pancreatic islet cell antigens that bind with antibodies found in the sera of patients afflicted with insulin-dependent (Type I) diabetes mellitus (IDDM). More particularly, the invention relates to proteins and peptides that bind with islet cell antibodies (ICA) and that are prepared by recombinant DNA (rDNA) or synthetic methods. The invention also concerns cloned DNA encoding such ICA proteins and peptides. The ICA proteins and peptides of the present invention are useful as immunoassay reagents in the presymptomatic diagnosis of IDDM.

The accumulating evidence of cellular and humoral abnormalities associated with IDDM has led to the hypothesis that the disease is an autoimmune disorder. Serum antibodies directed against the insulin-producing beta cells of the pancreatic islets have been detected by immunofluorescence, [G. F. Bottazzo, A. Florin-Christensen, and D. Doniach: Islet Cell Antibodies in Diabetes Mellitus With Autoimmune Polyendocrine Deficiencies, Lancet ii:1279–1283 (1974), and A. C. MacCuish, J. Jordan, C. J. Campbell, L. J. P. Duncan, and W. J. Irvine: Antibodies to Islet-cell in Insulin-dependent Diabetics With Coexistent Autoimmune Disease, Lancet ii:1529–1533 (1974)]. These autoantibodies are observed in 70–80% of newly diagnosed diabetics (NDD), but only in 0.1–1% of normal control subjects [C. H. Brogren and A. Lernmark: Islet Cell Antibodies in Diabetes. Clin. Endocrinol. Metab. 11:409–430 (1982)], and G. F. Bottazzo, R. Pujol-Borrell, and D. Doniach: Humoral and Cellular Immunity in Diabetes Mellitus. Clin. Immunol. Allergy 1:139–159 (1981)]. ICAs have come to be accepted as one predictive factor for IDDM. A review of current knowledge on ICA is provided by A. Lernmark, Diabetic Medicine 4:285–292 (1987).

The conventional ICA assay consists of exposing pancreas sections to sera, staining with a second antibody bearing either a fluorescent [G. F. Bottazzo et al., supra] or enzyme label [P. G. Colman, M. Tatkus, A. Rabizadeh, C. Cahill, and G. S. Eisenbarth: Assay for Islet Cell Antibodies with Rat Pancreas and Peroxidase Protein A. Diabetes Care 11:367–368 (1988)], and observing under a microscope. Another similar method involves a biotin-avidin sandwich and immunofluorescent detection [T. Kobayashi, T. Sugimoto, T. Itoh, K. Kosaka, T. Tanaka, S. Suwa, K. Sato and K. Tsuju: The Prevalence of Islet Cell Antibodies in Japanese Insulin-dependent and Non-insulin-dependent Diabetic Patients Studied by Indirect Immunofluorescence and by a New Method. Diabetes 35:335–340 (1986)]. These methods are time consuming, laborious, difficult to reproduce, and have limited sensitivity. The development of a more convenient immunoassay for ICA would permit widespread testing for epidemiology and correlation with IDDM, and ultimately prediction of the disease with a screening test.

A major limitation of current ICA tests is the limited knowledge and characterization of the islet cell antigens involved. The ICA's may be of low titer or affinity and approachable only with characterized antigens. ICA antigens that are detected by the immunofluorescence test are of special interest; these antigens may include:

(1) islet cell surface moieties [N. K. MacLaren, S. W. Hugng, and J. Fogh: Antibody to Cultured Human Insulinoma Cells in Insulin-dependent Diabetes. Lancet 1:997–1000 (1975), and A. Lernmark, Z. R. Freedman, C. Hofmann, A. H. Rubenstein, D. F. Steiner, R. L. Jackson, R. J. Winter and H. S. Traisman: Islet-cell-surface Antibodies in Juvenile Diabetes Mellitus. N. Engl. J. Med. 299:375–380 (1978)], (2) insulin [J. P. Palmer, C. M. Asplin, P. Clemons, K. Lyen, O. Tetpati, P. K. Raghu and T. L. Paquette: Insulin Antibodies in Insulin-dependent Diabetics Before Insulin Treatment. Science 222:1337–1339 (1983), and S. Srikanta, A. T. Ricker, D. K. McCulloch, J. S. Soeldner, G. S. Eisenbarth and J. P. Palmer: Autoimmunity to Insulin, Beta Cell Dysfunction, and Development of Insulin-dependent Diabetes Mellitus. Diabetes 35:139–142 (1986)], (3) a 64,000 dalton (64 kd) islet protein of unknown cellular localization [S. Baekkeskov, J. H. Nielsen, B. Marner, T. Bilde, J. Ludvigsson, and A. Lernmark: Autoantibodies in Newly Diagnosed Diabetic Children Immunoprecipitate Human Pancreatic Islet Cell Proteins. Nature 298:167–169 (1982). Recent evidence indicates that the 64kd protein is glutamic acid decarboxylase (GAD). [S. Baekkeskov, J-H. Aanstoot, S. Christgau, A. Reetz, M. Solimena, M. Cascalho, F. Folli, H. Richter-Olesen and P. De-Camilli: Identification of the 64 k autoantigen in insulin-dependent diabetes as the GABA-synthesizing enzyme glutamic acid decarboxylase. Nature 347:151–156 (1990)], (4) cytoplasmic antigens [G. F. Bottazzo, A. Florin-Christensen, and D. Doniach: Islet Cell Antibodies in Diabetes Mellitus With Autoimmune Polyendocrine Deficiencies. Lancet 2:1279–1283 (1974), A. C. MacCuish, J. Jordan, C. J. Campbell, L. J. P. Duncan, and W. J. Irvine: Antibodies to Islet-Cell in Insulin-Dependent Diabetics With Coexistent Autoimmune Disease. Lancet 2:1529–1533 (1974), R. Lendrum, G. Walker, and D. R. Gambli: Islet-Cell Antibodies in Juvenile Diabetes Mellitus of Recent Onset. Lancet 1:880–883 (1975), and W. J. Irvine, C. J. McCallum, R. S. Gray, G. J. Campbell, L. J. P. Duncan, J. W. Farquhar, H. Vaughan, and P. J. Morris: Pancreatic Islet Cell Antibodies in Diabetes Mellitus Correlated With The Duration and Type of Diabetes, Co-existent Autoimmune Disease, and HLA-type. Diabetes 26:138–147 (1977)], (5) glycoconjugates [R. C. Nayak, M. A. K. Omar, A. Rabizadeh, S. Srikanta, and G. S. Eisenbarth, "Cytoplasmic" Islet Cell Antibodies: Evidence That the Target Antigen is a Sialoglycoconjugate. Diabetes 34:617–619 (1985); P. Vardi, E. E. Dibella, T. J. Pasquarello, and S. Srikanta, Islet Cell Autoantibodies: Pathobiology and Clinical Applications. Diabetes Care 10:645–56 (1987); B. K. Gillard, J. W. Thomas, L. J. Nell and D. M. Marcus, Antibodies Against Ganglioside GT3 in the Sera of Patients with Type I Diabetes Mellitus. Journal of Immunology 142:3826–32 (1989)].

Several reports indicate a high prevalence of anti-64 kd antibody in prediabetic sera as well as newly diagnosed diabetic sera [S. Baekkeskov, M. Landin, J. K. Kristensen, S. Srikanta, G. Jan Bruining, R. Mandrup-Poulsen, C. de Beaufort, J. S. Soeldner, G. Eisenbarth, F. Lindgren, G. Sundquist, and A. Lernmark: Antibodies to a 64,000 MW Human Islet Cell Antigen Precede the Clinical Onset of Insulin-dependent Diabetes. J. Clin. Invest. 79:926–934 (1987), M. A. Atkinson, N. K. Maclaren, W. J. Riley, D. W. Sharp and L. Holmes: Mr 64,000 Autoantibodies (64KA) Predict Insulin Dependent Diabetes. American Diabetes Assoc. 48th Annual Meeting (1988) Abstract #391, and M. A. Atkinson, N. K. Maclaren, D. W. Scharp, P. E. Lacy, and W. J. Riley: 64000 Mr autoantibodies as predictors of insulin-dependent diabetes. The Lancet 335:1357–1360 (1990)].

Some other molecular species have been characterized by Western blotting as being "common antigens" recognized by diabetic sera [D. G. Karounos, V. J. Virta, L. J. Nell, and J. W. Thomas: Analysis of Human and RINm5F Islet Cell Antigens. American Diabetes Assoc. Res. Symp. Woods Hole, Ma. October 1987; Abstract #120]. These antigens have molecular weights of 150 kd, 84 kd, 60 kd, 49 kd, and 36 kd. A more recent report from the same laboratory indicates that there is a RIN antigen of Mr 52,000 that reacts with 29% of diabetic sera. [D. G. Karounos and J. W. Thomas: Recognition of Common Islet Antigen by autoantibodies From NOD Mice and Humans With IDDM. Diabetes 39:1085–1090 (1990), D. G. Karounos, L. J. Nell, and J. W. Thomas: Autoantibodies present at onset of type I diabetes recognize multiple islet cell antigens. Autoimmunity 6:79–91 (1990), and D. G. Karounos, J. S. wolinsky, B. K. Gillard, and J. W. Thomas: Molecular Mimicry in Type I Diabetes: An Antigenic Determinant on a Rubella Virus Protein is Shared with a 52 kD Beta Cell autoantigen. Diabetes 39:96A (1990)]. The first and third references indicate that the 52,000 antigen is RIN specific, not found in human islets or other tissue.

SUMMARY OF THE INVENTION

The present invention provides a series of cloned nucleic acids that code for one or more proteins or protein fragments which bind selectively with pancreatic islet cell antibodies (ICA). Such cloned nucleic acids are characterized by the cDNA inserts in deposited recombinant bacteriophages ATCC 40550, 40551, 40552, 40553, 40554, 40703, 40704, 40705, 40706, and ICA-512.3 (ATCC 7503).

The present invention, accordingly, also provides ICA proteins and peptide fragments thereof which are encoded by the cloned nucleic acids and are useful in the diagnosis of insulin-dependent (Type I) diabetes mellitus (IDDM). The ability of such proteins and peptides to bind to the antibody combining site on ICAs also confers utility in the binding or blocking of human immunoglobulin, T-cells or B-cells involved in IDDM, including circulating immunoglobulin, T-cells, and B-cells.

The ICA proteins and peptides of the present invention are obtained by such methods as full or partial expression, optionally with subsequent fragmentation, of the present cloned nucleic acids; and peptide or polypeptide synthesis based on the amino acid sequences determined from the present cloned cDNAs or from the full length ICA antigen genes that can be determined or isolated from islet cell nucleic acid libraries with the aid of the present complementary cloned cDNA sequences. Accordingly, such ICA proteins and peptides include the full length ICA proteins present in or on islet cells and which are expressed by the human gene whose mRNA is at least in part complementary with the complete sequence of the present cloned cDNAs. Also included in the ICA proteins and peptides of the present invention are the proteins expressed by recombinant cloning vehicles comprising the present cDNA inserts and fragments of such proteins obtained by partial expression or by subsequent fragmentation such as with restriction nucleases. The ICA proteins and peptides of the present invention also include peptides obtained by protein synthesis, such as those that are 3 amino acids in length or longer, which represent ICA epitopes or analogues or derivatives thereof.

The present invention offers a number of significant advantages. The molecular cloning of ICA antigens affords the preparation of large and reproducible amounts of material for use in research, diagnosis, and treatment of IDDM, as well as the opportunity to study the biological mechanisms involved in islet cell destruction and the appearance of ICA. The availability of large quantities of pure antigen enables the development of highly sensitive and specific immunoassays which can be used to screen the general population for presymptomatic IDDM or a predisposition to develop IDDM.

BRIEF DESCRIPTION OF THE DRAWINGS AND SEQUENCE LISTING

FIG. 6 is a control profile using the cloning phage with no recombinant insert.

FIGS. 7 and 10 are summaries of the sera profiles of ICA clones showing reactivity values assigned by visual interpretation of the profiles in FIGS. 1–5 and 8 and 9, respectively.

FIG. 11 shows the results of immuno-precipitation of one of the ICA clones with diabetic and normal sera.

Figure 1B:
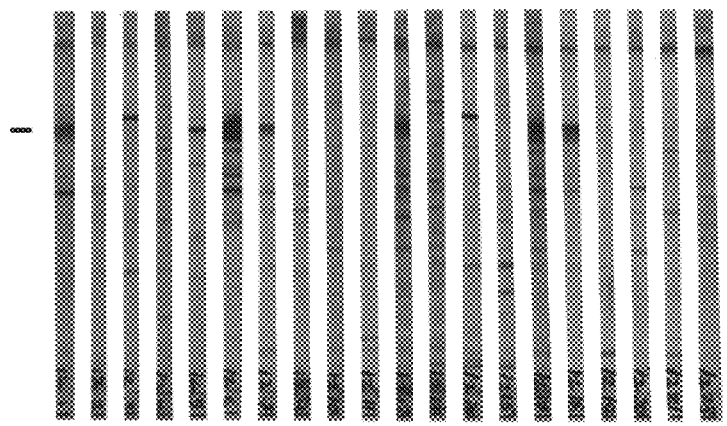
FIGS. 1–5, 8 and 9 are reactivity profiles of ATCC-deposited ICA clones prepared in accordance with the present invention with diabetic and normal sera under conditions described in the Examples.
Figure 1A:
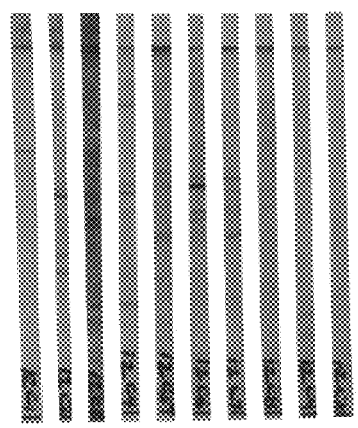
Figure 2A:
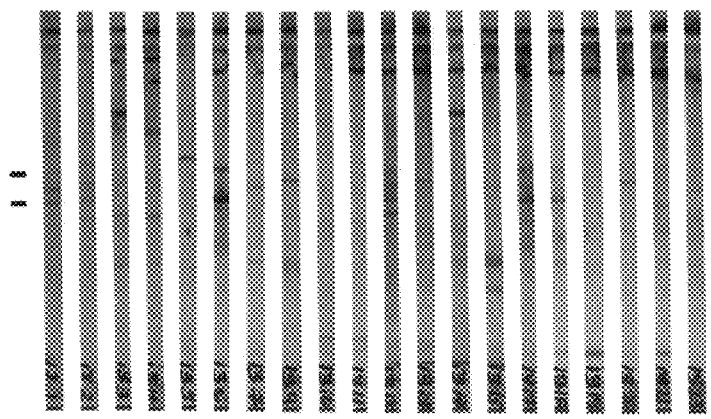
Figure 2B:
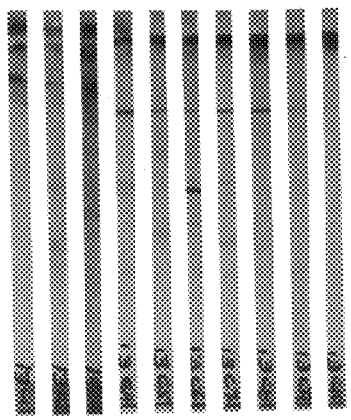
Figure 3A:
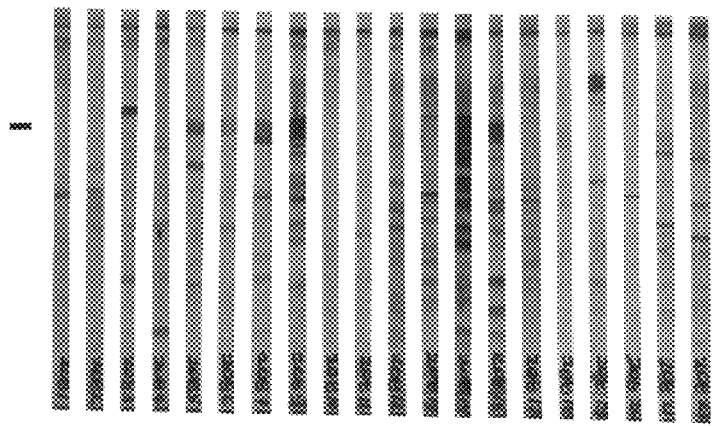
Figure 3B:
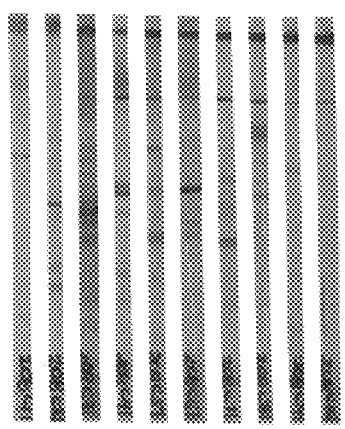
Figure 4A:
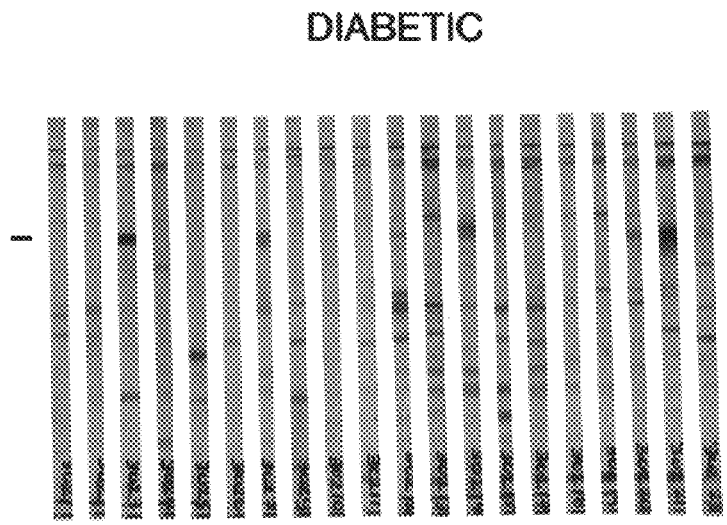
Figure 4B:
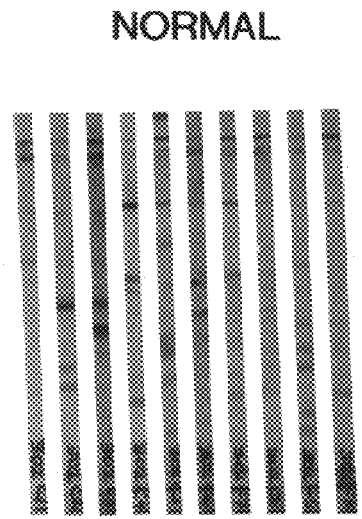
Figure 5A:
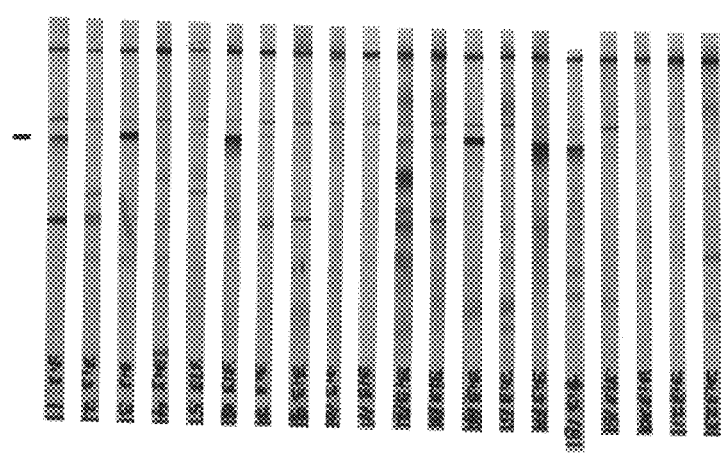
Figure 5B:
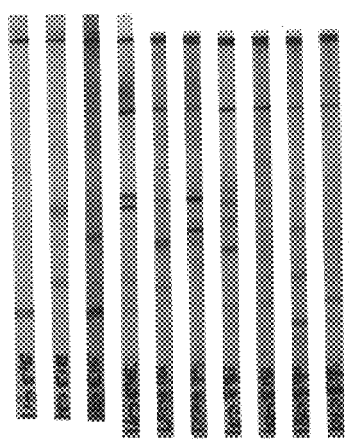
Figure 8A:
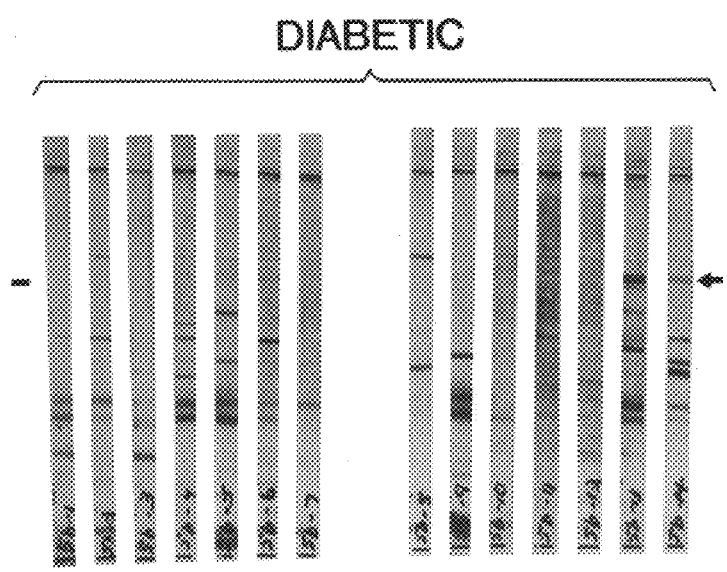
Figure 8B:
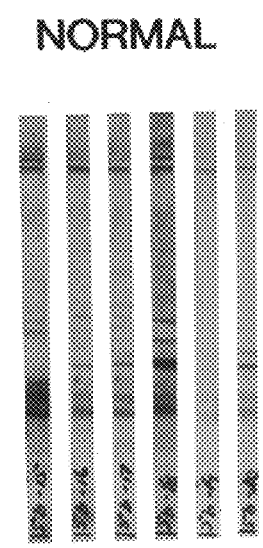
Figure 9A:
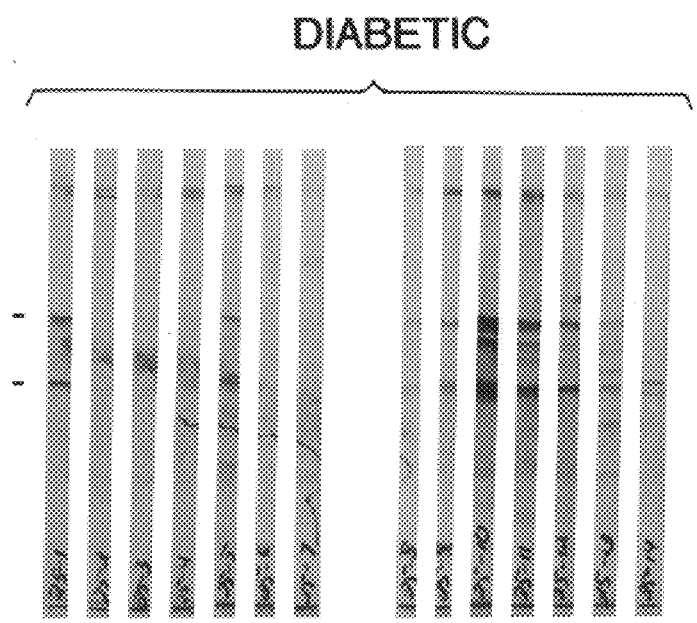
Figure 9B:
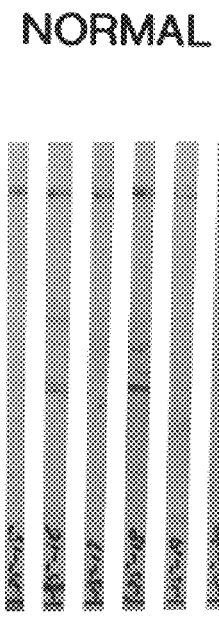
Figure 11A:
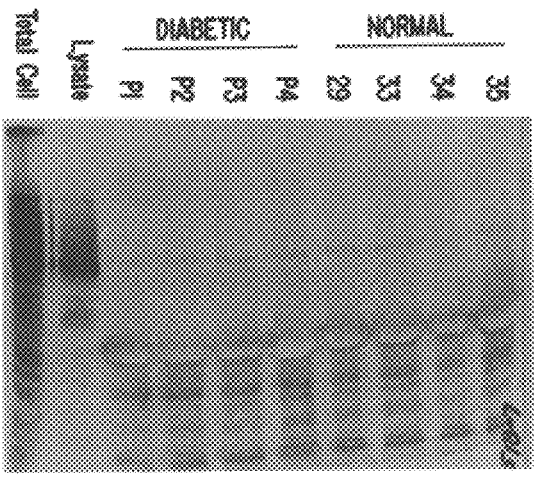
Figure 11B:
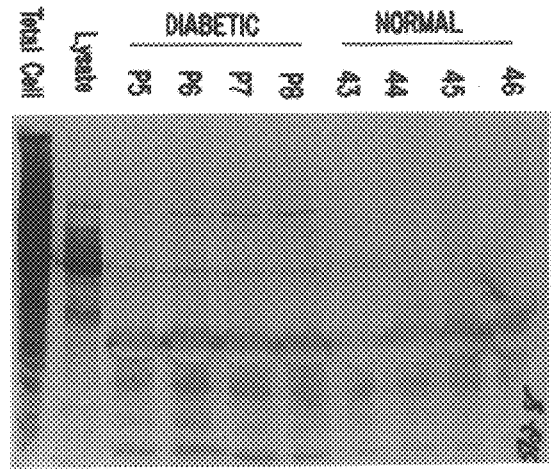
Figure 11C:
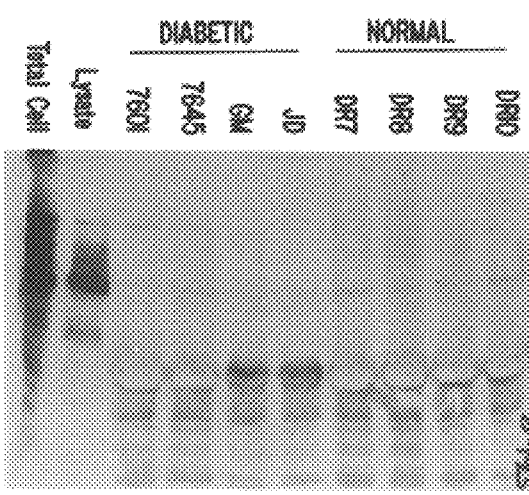
Figure 11D:
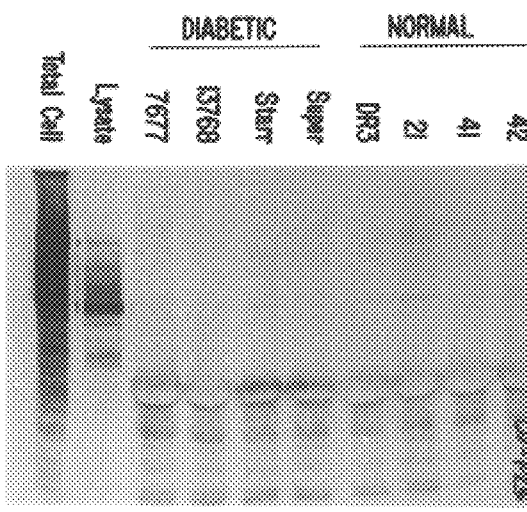
Figure 12:
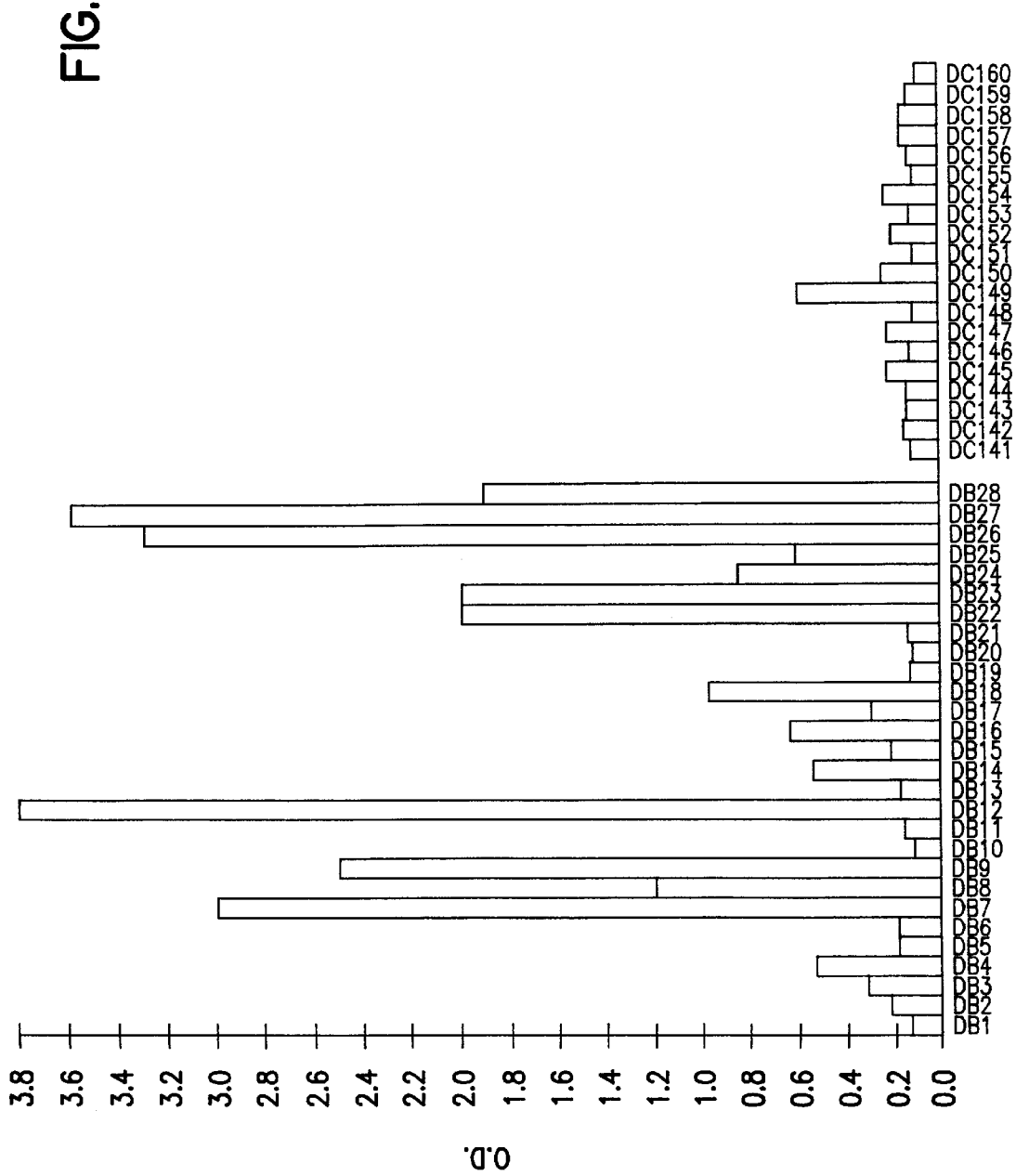
Figure 13A:
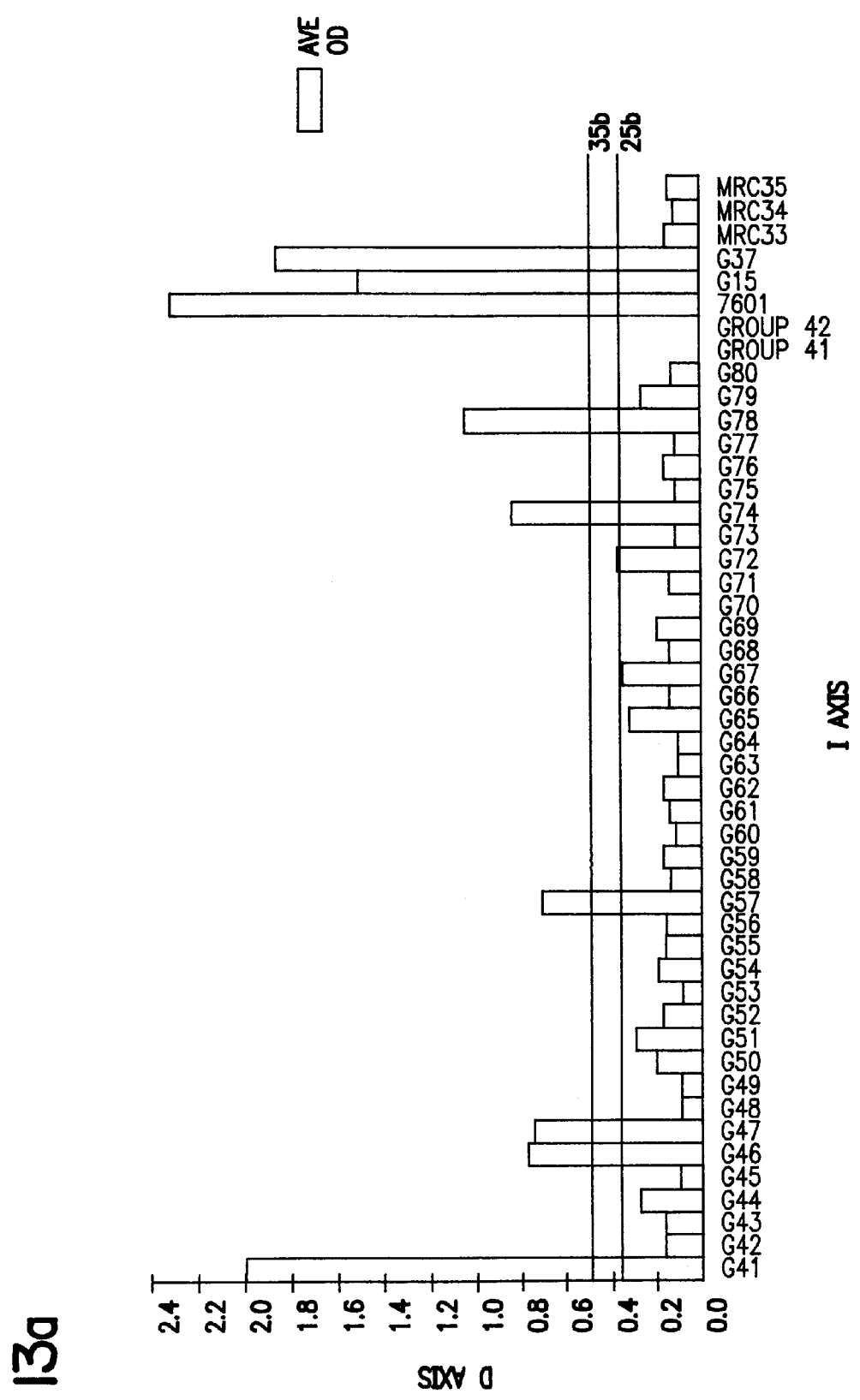
Figure 13B:
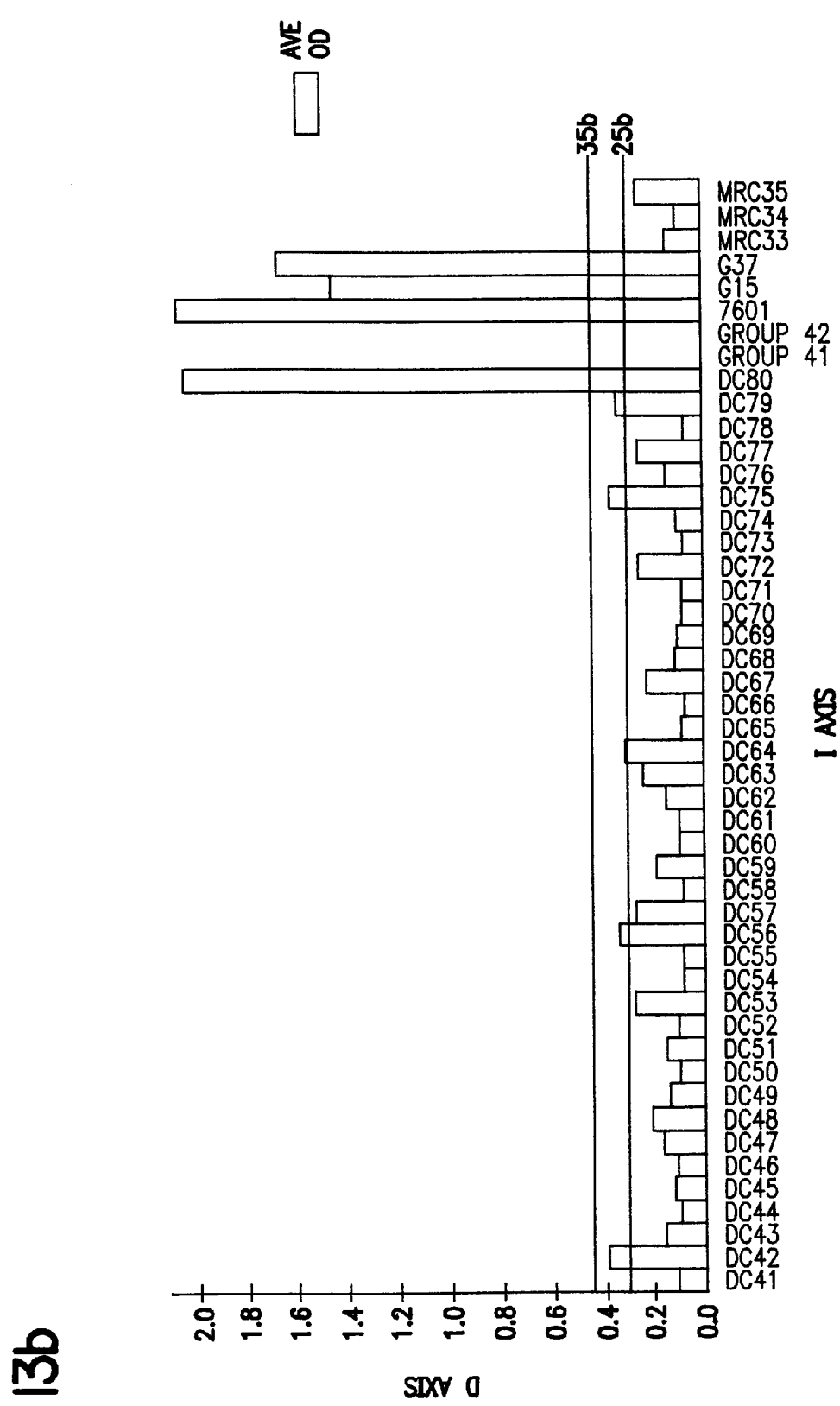

FIGS. 12 and 13 show ELISA profiles illustrating the specificity of reactivity of particular ICA clones (ICA-512 (ATCC 40706) and ICA-12 (ATCC 40550)) with diabetic sera.

The sequence listing provides the DNA and inferred protein sequences for particular ICA clones as following:

| SEQ ID NO. | ICA CLONE |
|---|---|
| 1 | 12 |
| 2 | 13 |
| 3 | 208 |
| 4 | 302 |
| 5 | 313 |
| 6 | 12.3 |
| 7 | 525 |
| 8 | 505 |
| 9 | 512 |
| 10 | 512.3 |

DESCRIPTION OF THE PREFERRED EMBODIMENTS

As used herein, the term "ICA antigens" shall be understood to refer to the proteins and peptides provided by the present invention even though it is recognized that in some cases peptide forms will not to be "antigens" in the strict sense, i.e., they will be haptenic since they will require attachment to a conventional macromolecular carrier in order to stimulate the production of antibodies in a host animal.

Furthermore, the "cloned nucleic acids", "cloned ICA antigen sequences", "cDNA inserts", and like terms shall refer to the inserts in deposited recombination phages ATCC 40550, 40551, 40552, 40553, 40554, 40703, 40704, 40705, 40706, and 75030, and also to other nucleic acid sequences of full length genes, or fragments of such sequences, comprising such deposited sequences. It will be recognized that one or more full length ICA antigens are characterized by homology with the above deposited cDNA inserts, however, it is possible that two or more of such cDNA inserts correspond to a single ICA antigen. For example, the insert in ATCC 40703 appears to encompass the inserts for both ATCC 40550 and ATCC 40554, and thus these three inserts may all correspond to different and/or overlapping portions of a single ICA antigen. Moreover, ATCC 40706 is comprised in ICA-512.3 (ATCC 75030).

Preparation of Cloned ICA Antigen Sequences

In general, the cloned ICA antigen sequences of the present invention are obtained by expressing human genes in a suitable recombinant cloning vehicle, e.g., bacteriophage, and probing the resulting gene library with IDDM serum to select antigens that are recognized by ICA antibodies. Recombinant antigens are then screened with a panel of diabetic and normal sera to determine the disease specificity of the identified clones.

The particular deposited clones were more particularly obtained by the following method (further details can be found in the Examples below). A human cDNA library was generated by extracting RNA from purified human islets. This RNA was fractionated by chromatography to separate poly-A mRNA from other RNA such as ribosomal RNA and fragments of degraded RNA. The separated mRNA was reverse transcribed with a commercially available cDNA kit (Bethesda Research Laboratories), ligated to Eco RI DNA linkers, and ligated into lambda gt-11 arms for in vitro packaging. The ligated lambda was packaged using a commercial kit (Stratagene) and then amplified on a bacterial lawn in a plate format.

The phage library was screened with antibodies from autoimmune patients with Type I diabetes. Agarose plates were spread with bacteria infected with the phage, and recombinant protein expression was induced chemically. The protein was deposited onto filters which were then probed with serum. Plaques that appeared to be positive were isolated from the agarose plates and purified through two rounds of isolation. Subsequent to cloning, the gt-11 phage was infected into a bacterial host for large scale expression. Specificity of the proteins expressed by the cloned cDNA was evaluated by Western blotting of bacterial extracts containing the cloned human protein. Preparative polyacrylamide gels were run and electroblotted onto membranes, the membranes were cut into strips, and then reacted with a series of normal and diabetic sera. The clones that generated proteins that reacted exclusively or predominantly with diabetic sera were selected.

Recombinant Cloning Vehicles and Subcloning

As is conventionally known in the art, the cDNA transcripts of the present invention, such as library cDNA or cDNA inserts excised from a cloning vehicle, can be incorporated into a variety of recombinant cloning vehicles for amplification of sequences of interest and for expression of ICA antigens of interest. A recombinant cloning vehicle will be understood to be a biochemical molecule or structure, e.g., DNA, that allows insertion of polynucleotide sequences and replication of the inserted polynucleotide sequences when the vehicle is appropriately incorporated into a host cell. An expression vehicle additionally includes the property of expressing the protein encoded by the inserted polynucleotide. In an expression vector, the inserted ICA antigen sequence is operably linked to a suitable control sequence capable of effecting the expression of ICA antigen in a suitable host. The control sequence involved will vary according to the host and transformation method selected. These matters are within the ordinary skill of the art.

Suitable recombinant cloning vehicles include plasmids, viruses and bacteriophage, and integratable fragments of DNA (i.e., fragments integratable into the host genome by recombination). Expression vehicles are particularly preferred and are exemplified, without limitation, by bacterial pEMBL, pMMB, pUK, pATH, and pGEX, yeast pAAH5, pYE4, and pAB112, mammalian pRSV, vaccinia derived vectors, baculovirus derived vectors, papilloma derived vectors, retroviral vectors, and shuttle vectors such as pCDM8. For a review, see D. M. Glover, DNA Cloning: A Practical Approach (1985) IRL Press Ltd. Suitable host cells include procaryotes, yeast, and higher eucaryotic cells including mammalian cells.

Subcloning of cDNA inserts can involve excising the insert for ligation into a different cloning vehicle. The insert can be excised using the restriction enzyme corresponding to the linkers used in the original insertion or using restriction enzymes selected from a restriction map of the insert. The excised cDNA can be inserted into another suitable vector for sequencing, amplification, or expression as desired. Should the terminal restriction sites in the original cloning vehicle have been destroyed, other enzymes can be used to recover the insert and resulting flanking regions from the cloning vehicle deleted by conventional means.

Another method of preparing DNA fragments for insertion into a cloning vehicle is the use of polymerase chain reaction (PCR) amplification. This procedure can be used on ligation reaction products to amplify the amount of DNA and introduce desired restriction sites for subcloning. PCR can also be used to replicate a fragment with desired restriction sites for transfer from one vehicle into another vehicle.

Full-Length Gene Cloning

Fragments of the cDNA inserts of the present invention can be used to isolate full-length cDNA or genomic DNA clones from appropriate libraries by standard methods. The target library is spread on plates, allowed to grow, transferred to filters, and reacted with DNA probes. Such DNA probes are generated from restriction fragments of the cDNA inserts by such methods as end labeling, nick translation, random primed transcription, or photochemical means. Oligonucleotides can be synthesized, labeled, and used as hybridization probes. RNA probes can also be generated from subcloned cDNA by transcription from appropriate templates.

Recombinant cloning vehicles, e.g., phage or plasmids, that appear to react with the partial cDNA clones are re-screened and then restriction mapped. Promising clones are then sequenced to confirm the hybridization of the original probes and to obtain extended sequence information on the larger fragment. If full-length clones are not obtained in this procedure, the complete sequence of the nucleic acid coding for the human gene can be pieced together from overlapping sequences of cloned fragments.

An alternative method for obtaining longer fragments, and possibly full-length clones, uses antibodies raised against ICA antigens expressed by partial clones. After identifying an antigen of interest, it can be used as an immunogen to raise monoclonal or polyclonal antibodies of high titer and affinity. Such antibodies will enable the detection of longer cDNA clones and cDNA clones present in lower amounts in the library.

Antigen and Peptide Synthesis

ICA antigens, as defined herein, can be prepared in a number of different ways from the clones and sequence information provided by the present invention. One can simply express the proteins from ICA antigen clones obtained according to the present invention, particularly from the deposited clones. Such expressed proteins, or fragments or digestion products thereof, can be used as antigens for binding to islet cell antibodies. However, direct use of bacterial expression extracts may not be possible in some cases since human sera normally react nonspecifically with E. coli proteins. In such cases, the expressed ICA antigens can be isolated by conventional techniques such as electrophoretic separation followed by immobilization on membranes (Western blotting), or by column chromatography or affinity purification (e.g., anti-beta-galactosidase affinity resin chromatography or other conventional biochemical means, e.g., salt or temperature precipitation).

Alternatively, peptide fragments can be synthesized by well-known methods from the amino acid sequences deduced from experimentally determined DNA sequences of ICA antigen clones. Overlapping peptides can be synthesized and tested for reactivity with ICA sera. As reactive peptides are found, smaller peptides can be prepared in order to map the smallest reacting unit, i.e., the epitope.

Methods

A principal use of the ICA antigens provided by the present invention is in the diagnosis and prediction of IDDM. In such a method, a blood sample, normally a serum sample, is reacted with a selected one or series of ICA antigens and immunoreactivity determined by any conventional technique. It is further contemplated that the immunoreactivity profile with different ICA antigens can provide diagnostically significant information concerning the nature of the disease, e.g., subtypes, the state of the disease, the proximity to onset of the disease, the efficacy of therapy, e.g., immune therapy, and the like.

A further use of the present ICA antigens is in the identification, marking, or specific destruction of autoreactive B-cells. If autoantibodies have a deleterious effect in IDDM, it is contemplated that anti-B-cell therapy can slow or stem the progress of the disease from prediabetes to clinical IDDM.

Another use of the present ICA antigens is in the identification of islet-reactive T-cell populations. ICA antigens can serve as stimulating antigens for T-cell culture, permitting significantly improved T-cell cloning, identification, and growth. It is contemplated that ICA T-cell detection can be significant in the diagnosis of the pre-diabetic state, and that monitoring the level of autoreactive T-cells can give an indication of the progress of the disease and the utility of immune modulating therapies. Further, the generation of ICA T-cell cultures can provide an in vitro model for designing diabetic therapies. Finally, it is contemplated that T-cell immunization can halt or retard autoimmunity by generating a humoral response against self-destructive elements.

The ability of ICA antigens to bind to human ICA immunoglobulin and T-cells can be used to block the binding of ICA to islet cells and islet cell components in vivo, and therefore are contemplated to provide a direct therapeutic effect.

The present invention will now be illustrated, but is not intended to be limited, by the following examples.

EXAMPLES 1. cDNA Library

Islets of Langerhans were purified by Dr.'s Paul Lacy and David Scharp at Washington Univ., St. Louis, Mo., USA, following a published procedure. [C. Ricordi, P. E. Lacy, E. H. Finke, B. J. Olack, and D. W. Scharp: An Automated Method for Isolation of Human Pancreatic Islets. Diabetes 37:413–420 (1988)]. Briefly, human pancreas was perfused with collagenase and then ground up. Ficoll gradient centrifugation was used to isolate the islets, which were then cultured for 1 week at room temperature. The islets were frozen and shipped.

Upon receipt, the islets were thawed, pooled, and washed. RNA was extracted using guanidinium thiocyanate and selectively precipitated with lithium chloride [G. Cathala, J. F. Savouret, B. Mendez, B. L. West, M. Karin, J. A. Martial, and J. D. Baxter: A Method for Isolation of Intact, Transtationally Active Ribonucleic Acid. DNA 2:329–335 (1983)]. About 770 $\mu$g of total RNA was obtained from each ml of centrifuged islets. Messenger RNA was purified using Pharmacia Oligo(dT)-cellulose Type 7 (Pharmacia Fine Chemicals, Piscataway, N.J., USA), following the procedure of Maniatis et al, [T. Maniatis, E. F. Fritsel, and J. Sambrook: Molecular Cloning, A Laboratory Manual (1982) Cold Spring Harbor Laboratory p. 197–198]. About 30 $\mu$g RNA was obtained after chromatography. In vitro translation using a BRL kit #8110 (Bethesda Research Laboratory, Gaithersburg, Md., USA), and $^{35}$S-methionine showed a broad range of molecular weight proteins being produced.

A BRL #8267SA kit was used for cDNA synthesis. Ten (10) $\mu$g of poly-A$^+$ RNA was used in the reaction. The ends were polished with $T_4$-DNA polymerase (Pharmacia), and the cDNA was methylated with Eco RI methylase (New England Biolabs, Beverly, Mass., USA) and S-adenosyl methionine and ligated to Eco RI linkers. The cDNA was digested with Eco RI and run on a Biogel A15M column (BioRad Laboratories, Rockville Center, N.Y., USA) to separate the linkers and fragments.

The cDNA was ligated into lambda gt-11 arms and packaged with a Stratagene Gigapack Plus kit (Stratagene Cloning Systems, LaJolla, Calif., USA). A library of approximately 8.5×10$^5$ insert-containing clones was obtained (measured with 5-bromo-4-chloro-3-indolyl-$\beta$-D-galactopyranoside), and amplified on E. coli Y1090 (Stratagene).

2. Sera

Sera from newly diagnosed diabetics were obtained from Dr. William Riley at the University of Florida, Gainesville, Fla., USA, and Dr. Alan Drash at the Children's Hospital of Pittsburgh, Pittsburgh, Pa., USA. Normal (non-diabetic) sera were collected from individuals in the laboratory. Sera from non-diabetic children were obtained from Dr. Jocelyn Hicks at the Children's National Medical Center in Washington, D.C. Sera were multiply adsorbed with filters that were prepared either by (a) lysing lambda-infected E. coli with chloroform and soaking nitrocellulose filters in this lysate, or (b) preparing filters by overlaying filters soaked with isopropyl-$\beta$-thio-galactopyranoside (IPTG) on lambda-infected *E. coli* in a plate format, essentially in the same manner as screening the library. Sera were diluted 1/20–1/200 in blotto solution (5% Carnation non-fat dry milk, 10 mM Tris pH 8.0, 150 mM NaCl, 0.05% Tween-20, and 0.05% sodium azide) after crude fractionation as noted below. Sera were used for ELISA experiments without preadsorption.

3. Screening

The screening procedure is based on standard protocols (T. V. Huynh, R. A. Young and R. W. Davis: Constructing and Screening cDNA Libraries in Fgt 10 and Gft 11 in DNA Cloning. D. M. Glover ed. (1985) IRL Press p. 490–78). Filters were prepared by plating about 50,000 plaque forming units (pfu) of the library onto each of ten 150 mm agarose plates. After growth at 42° C. for about 3 hours, filters (Nitrocellulose from Schleicher and Schuell, Keene, N.H., USA) containing IPTG were laid onto the plates and growth was continued at 37° C. for either 3–4 hours or overnight. Filters were blocked with a blotto solution and stored at 4° C.

Initially, all antibody reactions with filters were performed at room temperature for 3 hours. In later experiments, sera incubations were done overnight at 4° C. in blotto solution without Tween-20, while secondary antibody reactions were done at room temperature for 1.5 hours. All incubations and washing were done on platform shakers with gentle rotation.

The library was screened with human antibody probes several times. In the first instance, antibody was purified from diabetic sera by HPLC. In the second and third, sera were precipitated with 50% ammonium sulfate and dialyzed. For the first and third screenings, a mixture of two sera were used for all rounds of purification. For the second screening, a mixture of 20 diabetic sera was used for the primary purifications. In a further screening, 22 sera were pooled, precipitated with ammonium sulfate and dialyzed, and the final working dilution of each serum was 1/500 in blotto without Tween 20.

After incubation in the diabetic sera, filters were washed 5–10 minutes each in Tris-buffered saline (TBS), TBS with 0.05% Tween-20, and then in TBS. Human antibody bound to the filters was detected by reaction with rabbit anti-human IgG conjugated to alkaline phosphatase (1/500 in blotto, Dakopatts antibody D-336—DAKO Corp., Santa Barbara, Calif., USA). Filters were washed in TBS/Tween-20, TBS, TBS, and then detection buffer (0.1 M Tris-HCl, pH 9.5, 0.1 M NaCl, 0.05 M $MgCl_2$, recommended by BRL for use in their DNA detection kit No. 8239SA). Chromogenic substrates (nitro-blue tetrazolium and 5-bromo-4-chloro-3-indolyl phosphate) were added and the reaction was protected from light. After color development, the filters were washed in water, then in 10 mM Tris (pH 8.0), 1 mM EDTA (TE) and dried. Best observation of the plaques could be made when the filters were still matte wet.

Positive plaques were located on the original plates by alignment with the filters. For primary screens, a plug containing a positive plaque was removed using the butt end of a sterile Pasteur pipet. For subsequent screenings where individual plaques could be distinguished, the tip of the pipet was used. Plaques were eluted into plaque storage buffer (Maniatis et al., supra) and eluted for at least several hours.

The above screening methods produced the specific deposited ICA clones described herein with the exception of ICA-12.3 (ATCC 40703) and ICA-512.3 (ATCC 75030) which were isolated as follows.

Approximately $10^6$ plaque forming units of the phage library were screened by DNA hybridization for the presence of sequences homologous with the ICA-12 (ATCC 40550) cDNA. The phage plaques distributed over 20 agar plates were replicated onto nylon filters, and the phage DNA was denatured and immobilized for hybridization, by the conventional procedure of Benton and Davis (1977) Science 196:180. The hybridization probe was an agarose gel-purified sample of the cloned ICA-12 (ATCC 40550). cDNA separated from its plasmid vector by Eco RI digestion. The cDNA segment was tagged with $^{32}p$ by the random primer labeling method (Feinberg and Vogelstein (1984) Anal. Biochem. 137:266). Hybridization of the probe to nylon filters was done according to Berent et al. (1985) BioTech. 3:208. Phage plaques identified as containing DNA homologous with the ICA-12 (ATCC 40550) probe were picked from the master plates, and the phage were replicated for a second round of hybridization screening. Individual plaques remaining positive for ICA-12 (ATCC 40550) sequences were then characterized as to properties of cDNA inserts. The clone ICA-12.3 (ATCC 40703) was found by DNA sequence analysis to contain the entire protein coding sequence of the mRNA partially represented in ICA-12 (ATCC 40550).

Monoclonal antibodies (mAb) were raised using GST-ICA-512 (ATCC 40706) (see below) as immunogen. A mixture of culture supernatants from three mAb clones were pooled and used to screen the human islet lambda-gt11 expression library. The screening method was as described above, except that an alkaline phosphatase conjugated rabbit anti-mouse Ig (DAKO) was used as a second antibody. Clone ICA-512.2 was obtained and determined to have 670 bases more than ICA-512 (ATCC 40706) on the 5' end.

Since it appeared that ICA-512.2 did not contain the initiation site for the full length protein, a DNA probe was made by labelling a 230 base Pst I restriction fragment that was derived from the 5' section of ICA-512.2, (bases 201–431, corresponding to bases 1216–1446 of ICA-512.3 (ATCC 75030), shown in SEQ ID NO 10). This fragment was used to screen the library, and clone ICA-512.3 (ATCC 75030) was identified. SEQ ID NO 10 shows the DNA and inferred protein sequence of this clone.

4. Expression

The proteins expressed by individual clones were analyzed by expressing the clones in *E. coli* hosts. Initial expressions with clones identified as ICA-12 (ATCC 40550) and ICA-13 (ATCC 40553) were done with lysogens generated with the clones by standard means (Huynh, et al.). Subsequent expressions were done by infective expression into *E. coli* CAG-456 [M. Snyder, S. Elledge, D. Sweetser, R. A. Young, and R. W. Davis: Fgt-11: Gene Isolation with Antibody Probes and Other Applications, Meth. Enzymology 154:107–128 (1987)]. Cells were harvested and lysed by resuspension in Laemmli sample buffer [U. K. Laemmli, Nature 227:680 (1970)]. Better electrophoresis results were obtained when samples were sonicated to reduce the size of the DNA and reduce viscosity.

Protein gel electrophoresis and semi-dry electrotransfer onto either nitrocellulose (Schleicher and Shuell) or Immobilon (Millipore Company, Bedford, Mass., USA) were performed. Gels were stained with Coomassie Blue and filters were detected by immunoreaction with the same sera used to screen the library as detailed above.

5. Clone Analysis

In order to assess the usefulness of the individual clones for diagnosis of IDDM, each clone was tested for reactivity with a panel of diabetic and normal sera. This was done by reacting each serum with a Western blot strip from each clone. Preparative gel electrophoresis was followed by semi-dry electrotransfer of the proteins to filters. Identical 3 mm strips were cut from the filters and exposed to the various sera. Localization of antigen bands was done by reference to analytical Western blots and strips reacted with anti-beta-galactosidase antibody (1/2000 monoclonal antibody from Promega, Madison, Wis., USA). Antibody incubation and detection with secondary antibody were described above.

The reactivity profiles of the clones identified as ICA-12 (ATCC 40550), ICA-13 (ATCC 40553), ICA-208 (ATCC 40554), ICA-302 (ATCC 40554), ICA-313 (ATCC 40552), ICA-505 (ATCC 40705), and ICA-525 (ATCC 40704) are shown in FIGS. 1–5, 8 and 9 of the drawings. Identical filter strips were cut from preparative electrotransfer and reacted with diabetic and normal sera (for ICA-12 (ATTCC 40550), 13 (ATCC 40553), 208 (ATCC 40554), 302 (ATCC 40551), and 313 (ATCC 40552), the strips were reacted with 20 diabetic and 10 normal sera; while 14 diabetic and 6 normal sera were used for ICA-505 (ATCC 40705) and 525 (ATCC 40704). A control profile using the vector (lambda gt-11) having no DNA insert is shown in FIG. 6.

The filter strips were also rated according to intensity, 1=weak reactivity, 2, 3 and 4=very strong reactivity. Summaries of the reactivity ratings are given in FIGS. 7 and 10 of the drawings. In FIG. 7, sera 21–30 bearing the prefix "c" are the normal control sera, while the diabetic sera are presented with their source identification number. In FIG. 10, sera 15–20 bearing the "MRC" prefix are normal control sera, while again the diabetic sera are presented with their source identification numbers. In both figures, the numbers shown under the clone headings represent the strength of immunoreactivity assigned by visual interpretation.

Some clones identified in the first screening were found to be unreactive in the Western blot format. To test the serum reactivity of these clones, the lambda gt-11 phage were expressed in E. coli CAG456 as above and the antigen was extracted by treating the bacteria with 4 mg/ml lysozyme (Sigma, St. Louis, Mo., USA) in 25 mM Tris, pH 8, 10 mM EDTA, 50 mM glucose and 2 mM phenyl-methyl sulfonyl chloride (PMSF) for 5 minutes at room temperature. Cells were pelleted at 4° C. and resuspended in ice cold buffer (500 mM sodium chloride, 1% NP-40, 50 mM Tris, pH 8, 1 mg/ml aprotinin (Sigma), 2 mM PMSF, 2 µg/ml chymostatin (Sigma), 2 µg/ml Antipain (Sigma) and 2 µg/ml pepstatin. Extraction of antigen proceeded for 30 minutes on ice, during which time the solution was sonicated. Samples were spun in an Eppendorf microfuge for 5 minutes at 4° C. and supernatants were used for immunoprecipitation.

Immune reactions consisted of: 15 µl wash buffer (50 mM Tris, 150 mM sodium chloride, 1% NP-40, 5 mM EDTA, 2 mM PMSF, 2.5 µl human serum, and 10 µl extract. Reactions were left overnight. Antigen-antibody complexes were recovered with 20 µl of a 50% slurry of Protein-A Sepharose CL-4B (Pharmacia) for 1 hour on ice. The resin was washed six times with 500 µl of wash buffer and once with water. Sample buffer for PAGE was added and the samples were boiled for 5 minutes, centrifuged for 5 minutes, and run on 8% gels. Electroblotting was performed and the blots reacted with anti-beta-galactosidase antibody (1/1000 dilution of Sigma #G4644 in blotto solution) followed by anti-mouse Ig coupled to alkaline phosphatase (DAKO #D314) and development in dyes. The results are shown in FIG. 11 for an extract of ICA-512 (ATCC 40706). Arrows indicate the position of the recombinant antigen.

DNA insert size for the various clones was determined by growing them either in a plate lysate or liquid lysate format (Maniatis, et al., supra). Lambda DNA was extracted, and cut with Eco RI, and analyzed for size by agarose gel electrophoresis.

The above identified clones which reacted predominantly with diabetic sera have been is deposited with the American Type Culture Collection, Rockville, Md., USA. The SEQ ID NOs, deposit numbers, deposit dates, and determined insert sizes are shown in Table 1 below. All restrictions upon public access to these deposits will be irrevocably removed upon the grant of a patent and each deposit will be replaced if viable samples cannot be dispensed by the depository.

TABLE 1

| SEQ ID NO | Clone # | ATCC # | Deposit Date | Insert size (kb) |
| --- | --- | --- | --- | --- |
| 1 | ICA-12 | 40550 | Feb. 8, 1989 | 1.400 |
| 2 | ICA-13 | 40553 | Feb. 8, 1989 | 5.043 |
| 3 | ICA-208 | 40554 | Feb. 8, 1989 | 0.575 |
| 4 | ICA-302 | 40551 | Feb. 8, 1989 | 0.794 |
| 5 | ICA-313 | 40552 | Feb. 8, 1989 | 2.391 |
| 6 | ICA-12.3 | 40703 | Nov. 14, 1989 | 3.243 |
| 7 | ICA-525 | 40704 | Nov. 14, 1989 | 3.4 |
| 8 | ICA-505 | 40705 | Nov. 14, 1989 | 0.346 |
| 9 | ICA-512 | 40706 | Nov. 14, 1989 | 1.8 |
| 10 | ICA-512.3 | 75030 | June 13, 1991 | 3.3 |

DNA inserts were transferred to a Stratagene Bluescript vector. Sequencing was done by standard techniques using the T7 Sequencing kit (Pharmacia) in conjunction with the Stratagene Exo III/Mung bean nuclease kit for generating overlapping nested deletion series of plasmids.

The sequence is considered to be complete for ICA-12 (ATCC 40550), 302 (ATCC 40551), 313 (ATCC 40552), 208 (40554), 505 (ATCC 40705), 12.3 (ATCC 40703), 512 (40706), and 512.3 (ATCC 75030), while only partial sequencing is available for ICA-13 (ATCC 40553) and 525 (ATCC 40704). The DNA sequences are those experimentally derived as described above. All three possible reading frames in both orientations were examined for protein coding capability, i.e., long open read frames. The most likely protein sequence for each clone is presented in capital letters below the DNA sequence (except for ICA-505 (ATCC 40705) for which the available information does not permit assignment of the reading frame encoding the protein antigen).

ICA-512 (ATCC 40706) was transferred to a modified version of plasmid pGEX (Pharmacia) for protein expression and purification. This modified plasmid, pGEXc, was adapted for expression of lambda-gt11 products by inserting 2 additional bases between the Bam H1 and EcoRI restriction sites.

A pGEXc clone that was determined to bear the ICA-512 (ATCC 40706) insert in the correct orientation by restriction analysis and DNA sequenceing was expressed following the protocol suggested by the manufacturer (Pharmacia) except that growth after induction with IPTG was at 25° C. Cell lysis, purification of the GST-ICA-512 (ATCC 40706) fusion protein on a glutathione-Sepharose 4B column, cleavage of the fusion protein with thrombin (Sigma T-7009) and purification of the ICA-512 (ATCC 40706) cleaved product with glutathione-Sepharose 4B were performed as described [D. B. Smith and K. S. Johnson: Single-step purification of polypeptides expressed in Escherichia coli as fusions with glutathione S-transferase. Gene 67:31–40 (1988)].

ICA-512 (ATCC 40706) was adapted to an ELISA format to provide quantitative information about a large number of samples. Both the GST-ICA-512 (ATCC 40706) and the cleaved ICA-512 (ATCC 40706) were evaluated, and shown to give similar results with a panel of normal and diabetic sera.

FIG. 12 shows the reactivity of ICA-512 (ATCC 40706) with such a panel. The "DB" sera on the left are newly diagnosed diabetics, and the "DC" sera on the right are normal sera. In this experiment, 30 ng of cleaved and purified ICA-512 (ATCC 40706) was deposited in each well of an Immulon-2 microtiter plate (Dynatech, Chantilly, Va.) in TBS buffer and allowed to stand overnight. Other coating buffers have been tested and shown to be equivalent. All incubations and reactions were done at room temperature with orbital shaking. Unbound antigen was shaken out. The plate was blocked with a blotto solution containing Tween-20 for 1 hour, and then reacted with 1.5 µl of human serum diluted in 50 µl blotto/Tween. Incubation was for 1 hour. After washing 5 times with PBS/Tween, the wells were incubated with 100 µl of a 1/000 dilution of alkaline phosphatase (AP) conjugated anti-human IgG antibody (Sigma A-0287) for 1 hour. After washing 5 times in PBS/Tween and once for 15 minutes with TBS/Tween, the plate was developed with nitrophenyl-phosphate (1 Sigma tablet #104–105 in 10 ml of 1 M diethanolamine, 0.5 mM MgCl$_2$, pH 9.8) for 1–2 hours. Optical density was read at 405 nm.

FIG. 13 shows the reactivity of a panel of diabetic (G) and normal (DC) sera with ICA-12 (ATCC 40550) in an ELISA format. The last 6 sera on the right side of the panel are controls. In this experiment, a capture format was used, in which an Immulon-1 plate (Dynatech) was coated first with a conjugate of glutathione and bovine serum albumin (GT-BSA). This conjugate was formed by reacting 2 mg of reduced glutathione (Sigma G-4251) dissolved in 500 µl PBS with 2 mg maleimide activated BSA (Pierce 77115H) dissolved in 200 µl water for 2 hours at room temperature. The mixture containing the modified BSA was diluted 1/1400 in EIA coating buffer (0.1 M sodium carbonate, pH 9.5), and each well of the 96-well plate was coated with 50 µl overnight at room temperature. The plate was blocked as described above, washed, and each well was exposed to 300 ng GST-ICA-12 (ATCC 40550) fusion protein dissolved in 50 µl blott/Tween for 1 hour at room temperature. Incubation with human sera, washing, and development were done as described above.

The present invention has been particularly described and exemplified above. It is contemplated that many other variations and modifications of the invention can be made without departing from the spirit and scope hereof.

What is claimed is:

1. A method of blocking human islet cell immunoglobulin, T-cells, or B-cells, comprising the steps of contacting such immunoglobulin, T-cells, or B-cells with a polypeptide comprising the sequence of amino acids encoded by a DNA insert of a recombinant cloning vehicle selected from the group consisting of ATCC 40550 (SEQ ID NO: 1), 40551 (SEQ ID NO: 4), 40552 (SEQ ID NO: 5), 40553 (SEQ ID NO: 2), 40554 (SEQ ID NO: 3), 40703 (SEQ ID NO: 6), 40704 (SEQ ID NO: 7), 40705 (SEQ ID NO: 8), 40706 (SEQ ID NO: 9), and 75030 (SEQ ID NO: 10).

2. The method according to claim 1, wherein the polypeptide is obtained by expressing said DNA insert of said recombinant cloning vehicle in a bacterial cell.

3. The method according to claim 1, wherein the polypeptide is obtained by peptide synthesis.

4. The method according to claim 1, wherein said immunoglobulin, T-cells, or B-cells are contacted with a polypeptide comprising the sequence of amino acids encoded by the DNA insert of recombinant cloning vehicle ATCC 40550.

5. The method according to claim 1, wherein said immunoglobulin, T-cells, or B-cells are contacted with a polypeptide comprising the sequence of amino acids encoded by the DNA insert of recombinant cloning vehicle ATCC 40551.

6. The method according to claim 1, wherein said immunoglobulin, T-cells, or B-cells are contacted with a polypeptide comprising the sequence of amino acids encoded by the DNA insert of recombinant cloning vehicle ATCC 40552.

7. The method according to claim 1, wherein said immunoglobulin, T-cells, or B-cells are contacted with a polypeptide comprising the sequence of amino acids encoded by the DNA insert of recombinant cloning vehicle ATCC 40553.

8. The method according to claim 1, wherein said immunoglobulin, T-cells, or B-cells are contacted with a polypeptide comprising the sequence of amino acids encoded by the DNA insert of recombinant cloning vehicle ATCC 40554.

9. The method according to claim 1, wherein said immunoglobulin, T-cells, or B-cells are contacted with a polypeptide comprising the sequence of amino acids encoded by the DNA insert of recombinant cloning vehicle ATCC 40703.

10. The method according to claim 1, wherein said immunoglobulin, T-cells, or B-cells are contacted with a polypeptide comprising the sequence of amino acids encoded by the DNA insert of recombinant cloning vehicle ATCC 40704.

11. The method according to claim 1, wherein said immunoglobulin, T-cells, or B-cells are contacted with a polypeptide comprising the sequence of amino acids encoded by the DNA insert of recombinant cloning vehicle ATCC 40705.

12. The method according to claim 1, wherein said immunoglobulin, T-cells, or B-cells are contacted with a polypeptide comprising the sequence of amino acids encoded by the DNA insert of recombinant cloning vehicle ATCC 40706.

13. The method according to claim 1, wherein said immunoglobulin, T-cells, or B-cells are contacted with a polypeptide comprising the sequence of amino acids encoded by the DNA insert of recombinant cloning vehicle ATCC 75030.

14. A method for blocking human islet cell immunoglobulin, T-cells, or B-cells, comprising the steps of contacting such immoglobulin, T-cells, or B-cells with a fragment of a polypeptide comprising the sequence of amino acids encoded by the DNA insert of recombinant cloning vehicle selected from the group consisting of ATCC 40550 (SEQ ID NO: 1), 40551 (SEQ ID NO: 4), 40552 (SEQ ID NO: 5), 40553 (SEQ ID NO: 2), 40554 (SEQ ID NO: 3), 40703 (SEQ ID NO: 6), 40704 (SEQ ID NO: 7), 40705 (SEQ ID NO: 8), 40706 (SEQ ID NO: 9), and 75030 (SEQ ID NO: 10), said fragment being at least 3 amino acids long and being capable of binding an islet cell autoantibody, B-cell or T-cell.

15. The method according to claim 14, wherein the polypeptide is obtained by a process comprising expressing said DNA insert of said recombinant cloning vehicle in a bacterial cell.

16. The method according to claim 14, wherein the fragment is obtained by peptide synthesis.

17. The method according to claim 14, wherein said immunoglobulin, T-cells, or B-cells are contacted with a fragment of a polypeptide comprising the sequence of amino acids encoded by the DNA insert of recombinant cloning vehicle ATCC 40550.

18. The method according to claim 14, wherein said immunoglobulin, T-cells, or B-cells are contacted with a fragment of a polypeptide comprising the sequence of amino acids encoded by the DNA insert of recombinant cloning vehicle ATCC 40551.

19. The method according to claim 14, wherein said immunoglobulin, T-cells, or B-cells are contacted with a fragment of a polypeptide comprising the sequence of amino acids encoded by the DNA insert of recombinant cloning vehicle ATCC 40552.

20. The method according to claim 14, wherein said immunoglobulin, T-cells, or B-cells are contacted with a fragment of a polypeptide comprising the sequence of amino acids encoded by the DNA insert of recombinant cloning vehicle ATCC 40553.

21. The method according to claim 14, wherein said immunoglobulin, T-cells, or B-cells are contacted with a fragment of a polypeptide comprising the sequence of amino acids encoded by the DNA insert of recombinant cloning vehicle ATCC 40554.

22. The method according to claim 14, wherein said immunoglobulin, T-cells, or B-cells are contacted with a fragment of a polypeptide comprising the sequence of amino acids encoded by the DNA insert of recombinant cloning vehicle ATCC 40703.

23. The method according to claim 14, wherein said immunoglobulin, T-cells, or B-cells are contacted with a fragment of a polypeptide comprising the sequence of amino acids encoded by the DNA insert of recombinant cloning vehicle ATCC 40704.

24. The method according to claim 14, wherein said immunoglobulin, T-cells, or B-cells are contacted with a fragment of a polypeptide comprising the sequence of amino acids encoded by the DNA insert of recombinant cloning vehicle ATCC 40705.

25. The method according to claim 14, wherein said immunoglobulin, T-cells, or B-cells are contacted with a fragment of a polypeptide comprising the sequence of amino acids encoded by the DNA insert of recombinant cloning vehicle ATCC 40706.

26. The method according to claim 14, wherein said immunoglobulin, T-cells, or B-cells are contacted with a fragment of a polypeptide comprising the sequence of amino acids encoded by the DNA insert of recombinant cloning vehicle ATCC 75030.

* * * * *